USO11497133B2

(12) United States Patent
Rogers et al.

(10) Patent No.: US 11,497,133 B2
(45) Date of Patent: Nov. 8, 2022

(54) METHOD OF MAKING A DATA CENTRE

(71) Applicant: Bripco BVBA, Antwerp (BE)

(72) Inventors: Paul Rogers, Stanley Pontlarge (GB); Neil Crow, Cheltenham (GB); Lucian Hicks, Cheltenham (GB); Richard Whiteley, Cheltenham (GB); Aaron Favill, Leamington Spa (GB); Samuel Hanks, Cheltenham (GB); William Thornton, Cheltenham (GB)

(73) Assignee: Bripco BVBA, Antwerp (BE)

( * ) Notice: Subject to any disclaimer, the term of this patent is extended or adjusted under 35 U.S.C. 154(b) by 724 days.

(21) Appl. No.: 16/070,392

(22) PCT Filed: Jan. 17, 2017

(86) PCT No.: PCT/EP2017/050906
§ 371 (c)(1),
(2) Date: Jul. 16, 2018

(87) PCT Pub. No.: WO2017/129448
PCT Pub. Date: Aug. 3, 2017

(65) Prior Publication Data
US 2020/0113081 A1    Apr. 9, 2020

(30) Foreign Application Priority Data

Jan. 29, 2016    (GB) .................................... 1601721

(51) Int. Cl.
H05K 7/14        (2006.01)
H05K 7/20        (2006.01)
(Continued)

(52) U.S. Cl.
CPC ............ H05K 7/1488 (2013.01); B23P 15/26 (2013.01); H04L 67/12 (2013.01); H05K 7/20745 (2013.01); E04H 2005/005 (2013.01)

(58) Field of Classification Search
CPC .. H05K 5/0213; H05K 7/1488; H05K 7/1491; H05K 7/1492; H05K 7/1497;
(Continued)

(56) References Cited

U.S. PATENT DOCUMENTS 8,072,780 B1    12/2011    Roy
8,180,495 B1    5/2012    Roy
(Continued)

FOREIGN PATENT DOCUMENTS

DE    202010011402 U1    11/2010
EP    2309833 A1    4/2011
(Continued)

OTHER PUBLICATIONS

Search and Examination Report under Sections 17 & 18(3), dated Sep. 29, 2016.
(Continued)

Primary Examiner — Peter Dungba Vo
Assistant Examiner — Joshua D Anderson
(74) Attorney, Agent, or Firm — Carlos A. Fisher; Stout, Uxa & Buyan, LLP

(57) ABSTRACT

A method of making a data centre is disclosed, comprising making a data centre in an existing building (3010) having a floor, walls and a roof, an air inlet and an air outlet. The method includes: installing prefabricated data centre elements by (a) connecting to the inlet an air handling module (3001, 3002); and (b) installing cold aisle services modules (3011) each having one or more integrated blanking portions and one or more data centre services extending along its length terminating with a connection to an adjacent module (3011); and installing racks of IT equipment arranged in parallel rows; the method being so performed that the floor, racks, and cold aisle services modules (3011) together define parallel cold aisles for entraining cooling air flows to the IT (Continued)

equipment. Also disclosed are a data centre, a service carrying frame and a cold aisle services module for a data centre and a supporting frame for supporting prefabricated data centre elements.

25 Claims, 22 Drawing Sheets

(51) Int. Cl.
 *B23P 15/26* (2006.01)
 *H04L 67/12* (2022.01)
 *E04H 5/00* (2006.01)
(58) Field of Classification Search
 CPC .......... H05K 7/20181; H05K 7/20709; H05K 7/20718; H05K 7/20745; H05K 7/20836; E04H 2005/005
 See application file for complete search history.

(56) References Cited

U.S. PATENT DOCUMENTS

| | | | |
|---|---|---|---|
| 8,469,782 B1 | 6/2013 | Roy | |
| 8,523,643 B1 | 9/2013 | Roy | |
| 8,627,611 B2 | 1/2014 | Cottuli et al. | |
| 9,332,670 B1* | 5/2016 | Eichelberg | G06F 1/182 |
| 9,622,389 B1 | 4/2017 | Roy | |
| 9,693,486 B1 | 6/2017 | Roy | |
| 9,788,455 B1 | 10/2017 | Roy | |
| 9,823,715 B1 | 11/2017 | Roy | |
| 9,986,652 B1 | 5/2018 | Roy | |
| 9,999,166 B1 | 6/2018 | Roy | |
| 2009/0168345 A1 | 7/2009 | Martini | |
| 2009/0211272 A1* | 8/2009 | Larsen | F28D 5/00 |
| | | | 62/89 |
| 2010/0144265 A1 | 6/2010 | Bednarcik et al. | |
| 2010/0315775 A1* | 12/2010 | Grantham | H05K 7/20745 |
| | | | 361/688 |
| 2011/0100618 A1* | 5/2011 | Carlson | H05K 7/20745 |
| | | | 165/287 |
| 2011/0278998 A1 | 11/2011 | Caveney | |
| 2014/0298734 A1* | 10/2014 | Rogers | H05K 7/1495 |
| | | | 52/79.9 |
| 2017/0086333 A1 | 3/2017 | Roy | |
| 2017/0099747 A1 | 4/2017 | Roy | |
| 2017/0223874 A1 | 8/2017 | Roy | |
| 2017/0273222 A1 | 9/2017 | Roy | |
| 2017/0354065 A1 | 12/2017 | Roy | |
| 2018/0049343 A1 | 2/2018 | Roy | |
| 2018/0107255 A1 | 4/2018 | Roy | |
| 2018/0139869 A1 | 5/2018 | Roy | |
| 2018/0156570 A1 | 5/2018 | Roy | |

FOREIGN PATENT DOCUMENTS

| | | |
|---|---|---|
| EP | 2986094 A1 | 2/2016 |
| GB | 2467808 A | 8/2010 |
| WO | 2011148175 A2 | 12/2011 |
| WO | WO2012/142620 A1 | 10/2012 |
| WO | 2013021182 A1 | 2/2013 |
| WO | 2015051086 A1 | 4/2015 |

OTHER PUBLICATIONS

Search Report under Section 17, dated Jul. 26, 2016.
Further Search Report under Section 17, dated Sep. 28, 2016.
Extended European Search Report dated Feb. 10, 2022 in related European Application No. 21205814.3.

* cited by examiner

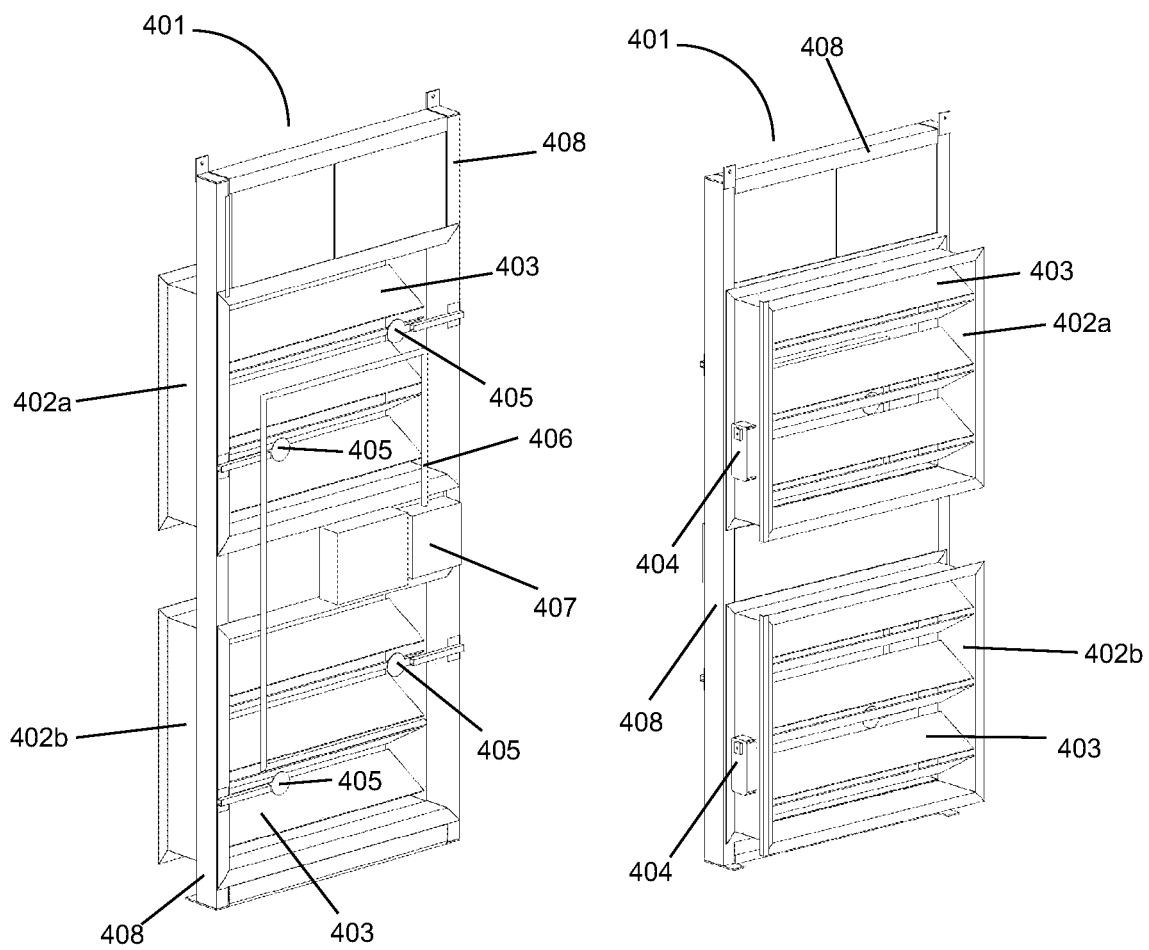

METHOD OF MAKING A DATA CENTRE

FIELD OF THE INVENTION

The present invention concerns data centres and a method of constructing a data centre. More particularly, but not exclusively, this invention concerns data centre buildings, for example provided in the form of a kit of parts. The invention also concerns a kit of parts for converting an existing building to a data centre.

BACKGROUND OF THE INVENTION

A data centre is a late 20th Century development that has grown as a response to the increasing demand for computer processing capability and a recognition of the importance of IT in the place of every business and organisation today. Whereas smaller organisations have sufficient processing power with laptops, PCs and occasionally servers, larger organisations require higher capacity centralised processing to serve a wide range of needs and applications. A few years ago this capacity was supplied by large mainframe computers, but more recently the method used has been to provide data centres comprising many networked computer servers known as blades installed in racks enabling controlled and modular expansion of capacity. The racks also typically house telecommunications equipment such as routers to handle data flow between the computer servers and data flow between the data centre and the outside world.

Data centres can mirror the growth and business activities of successful companies. The growth of a data centre within an expanding company may typically work as follows:

1. Initially the data centre may start as single rack of servers in an air conditioned room—sometimes referred to as a 'data closet'.
2. As the organisation expands and along with it the number of IT racks employed, the closets become 'Server Rooms' or 'IT Rooms'.
3. Eventually the number of racks and size of room expands, often to the point where a dedicated building or part of a building houses the IT. Whilst there is no strict definition of when the size of an IT facility becomes large, or sophisticated, enough to be termed a "data centre", data centres are typically relatively large IT facilities providing robust and resilient IT facilities. Typically, there will be more than 50 servers (often many more) and at least some redundancy in the power supply powering the servers to ensure continuity of service.
4. As the company grows and/or becomes a multi-national organisation additional data centres will be built and sometimes numbers of these will be consolidated into 'Super Data Centres'.

Recently, Data Centre providers have entered the marketplace offering third parties co-location facilities. For example, some large Data Centre providers construct and equip warehouse-sized data centres and sell space in them, such as on a rack-by-rack or hall-by-hall basis. Such providers allow third party organisations to benefit from the advantages of large, specially constructed data centres without having to take on the burden of overseeing construction and maintenance themselves.

Data centre facilities can require a floor space ranging from a few hundred square feet to a million square feet. The most prevalent size for a small data centre is five to ten thousand square feet with fifty to a hundred thousand square feet being the most common floor area requirement for a large data centre.

Data centres will typically have the ability to deliver applications spread across an organisation and/or supply chain and/or customers in differing geographical locations. There will typically be a dedicated mechanical and electrical (M&E) plant to deliver power, cooling and fire suppression with built-in redundancy with the aim of providing near continuous operation.

The IT industry has long recognised the criticality of central computing facilities and the need for energy efficient operations to control cost effectiveness. Current data centre technology is the summation of 30 years of innovation and engineering design thought and has come a long way in recent times. The most advanced new data centre designs commonly fall into one of two different types, each of which has advantages and disadvantages. The first, more traditional, common type of data centre is a huge, custom built warehouse style building which is often located so as to be able to take advantage of local weather conditions to aid cooling of the IT equipment it houses. These data centres can be spacious, ergonomic and highly energy efficient because the structure, layout and cooling systems of each data centre are designed from scratch around its particular location and intended use. Yahoo!'s "Computing Coop" data centre in New York is an example of this type of data centre.

The drawbacks of this type of data centre are the large cost and length of time for construction, which are necessary consequences of the bespoke design model. It is also not easy to add capacity—the data centre must be built large enough in the first place to cope with future increases in the number of servers required by its owner/occupier. These factors also make this style of data centre impractical for companies who need only a small or medium-sized data centre. A further significant drawback is the fact that only a few sites worldwide have a climate suitable for hosting such a large installation without placing undue demands on the cooling systems. The need for a large skilled construction workforce to be available at the site further limits the number of suitable locations.

The second common type of data centre is the modular data centre, which is constructed from several factory-built modules. The modules are typically built and sometimes even fitted out at a central facility and then shipped to the location of the data centre, where they are connected together and to the local utilities. U.S. Pat. No. 7,738,251 (Google), for example, describes a modular data centre in which each module is formed by an ISO shipping container. This second type of data centre addresses some of the problems with the first type, but has several disadvantages of its own. In particular, it is necessary for easy transport of the modules that they conform to the dimensions of ISO shipping containers; however this significantly limits the space available inside each module for IT equipment, cooling systems and human access. If actual shipping containers are used as the basic modules, then this also places severe constraints on how the modules can be linked up into a single data centre. These features also mean that this style of data centre is generally not as energy efficient as the first type.

Some of the disadvantages of containerised data centres are overcome by the modular data centres described in WO 2010/139921 (Bripco) and WO 2011/051655 (Colt Technology Services). The data centres of WO 2010/139921 and WO 2011/051655 both consist of several modules which connect to form a building having internal spaces that span several modules. This allows for many more layout options than is possible with a containerised design.

The data centres of WO 2010/139921 and WO 2011/051655 potentially suffer from a disadvantage in that, because the modules are assembled away from the site of the data centre, each module must be transported as a volumetric unit (where the volume of the unit when operational is the same as the volume of the unit when being transported). This necessarily involves significant costs due to the size of the modules, much of which volume comprises empty space inside the modules. This feature of prior art modular and/or containerised data centres places a limit on how energy efficient and cost-effective they can be, when the entire supply and construction process is taken into account.

Another type of data centre is the "chassis system" disclosed in WO2013021182 (Bripco BVBA). The "chassis system" data centre comprises a plurality of sections, each section including a ceiling portion and a plurality of supporting members, wherein the data centre services are mounted on the ceiling. WO2013021182 discloses a method of building a data centre in which services are mounted on each ceiling portion, the ceiling portions and supporting members are transported to site in a reduced volume configuration, and the ceiling portions and supporting members are assembled together on site, wherein, when assembled, the ceiling portions and supporting members define an assembled volume larger than the reduced volume occupied during transportation. In the data centre disclosed in WO2013021182, the ceiling portion and supporting members are typically structural components of the data centre building. A drawback of that system is that there is little freedom to use alternative materials to steel in the construction of the ceiling portions, and it is often necessary to ensure that the structural ceiling portions and supporting members meet differing local building regulations. Furthermore, while the "chassis system" of WO2013021182 can be assembled inside an existing building, the large size and significant weight of the ceiling portions can make such a task challenging and time-consuming for construction teams.

The present invention seeks to mitigate the above-mentioned problems. Alternatively or additionally, the present invention seeks to provide an improved data centre and an improved method of constructing a data centre.

SUMMARY OF THE INVENTION

In a first aspect, the present invention provides a method of making a data centre. The method may include a step of providing a building having a floor, walls and a roof. The method may for example be performed within a pre-existing building having a floor, walls and a roof. There may be a step of forming one or both of an aperture for forming an air inlet for supply of air into the building and an aperture for forming an air outlet for removal of air from the building. There may be a step of forming the air inlet and the air outlet. The aperture, air inlet and/or air outlet may already be provided in the building before the method of the invention is performed. The method includes a step of installing multiple prefabricated data centre elements in the interior of the building or otherwise associated with the building, preferably after the building has been provided. The multiple prefabricated data centre elements may include an air handling module, for providing cooling capacity for the data centre during use. The installation of the air handling module may for example include connecting it to the air inlet. The air handling module may for example be arranged to assist in the provision of a regulated and/or controlled supply of cooling air for cooling the IT equipment in the data centre, during operation. The air handling module may be provided at least partly within the building. Alternatively, the air handling module may be provided outside the building. In the case where the air handling module is provided outside the building it will for example be the case that (optionally conditioned) cooling air is suppled from the air handling module via the air inlet to the IT equipment. In the case where the air handling module is provided inside the building it may be the case that outside air is suppled via the air inlet to the air handling module. It is preferred that the air handling module is installed only after the building has been provided. In certain embodiments, however, the air handling module may form part of the structure of the building, once the data centre is operational. In such a case, the air handling module may provide the air inlet and air outlet mentioned above. For example, the step of providing in the building an aperture for forming an air inlet and an aperture for forming an air outlet may be satisfied by providing one aperture that accommodates the air handling module.

The cooling air provided in the building may be provided by means of an indirect air cooling regime (for example as mentioned in further detail below). Air will, during at least some times of operation of the data centre, pass into the building via the air inlet (although such air need not necessarily be ambient air from outside the building). Air will, during at least some times of operation of the data centre, pass out of the building via the air outlet (although such air need not necessarily be directly vented to atmosphere). The multiple prefabricated data centre elements may include multiple cold aisle services modules, which are installed in the interior of the building. The multiple prefabricated data centre elements may include one or more damper units for controlling the flow of air to and/or from the exterior of the building. At least some of the damper units may be provided in the air inlet of the building. At least some of the damper units may be provided in the air outlet of the building. In the case of an indirect air cooling regime for example, it may be that one or more damper units are provided elsewhere (other than the air inlet and the air outlet of the building). The one or more damper units may for example be arranged to assist in the provision of a regulated and/or controlled supply of cooling air for cooling the IT equipment in the data centre, and/or in the exhaustion of air flowing from the IT equipment in the data during operation.

In certain embodiments there is provided a method of making a data centre, wherein the method includes the following steps:

providing a building;
installing in the interior of the building multiple prefabricated cold aisle services modules, each cold aisle services module having:
a length and a width,
one or more integrated blanking portions including at least one ceiling member, and
one or more data centre services extending along the length of the cold aisle services module and terminating in a connector that is connected to a corresponding connector of an adjacent data centre services module; and
installing in the interior of the building multiple racks of IT equipment, the racks being arranged in multiple parallel rows;
the method being so performed that multiple parallel spaced apart cold aisles for entraining and encapsulating the flows of cooling air to the IT equipment in the racks are at least partially formed by the racks and the cold aisle services modules including the associated integrated blanking portions.

It will be appreciated that the multiple prefabricated data centre elements may include more than one air handling module. It will be appreciated that the air handling module may itself comprise a number of separate modules that are assembled together to form the air handling module. Each cold aisle services module has a length and a width, one or more integrated blanking portions including at least one ceiling member, and one or more data centre services extending along the length of the cold aisle services module and terminating in a connector that is connected to a corresponding connector of an adjacent data centre services module. The method may include installing in the interior of the building multiple racks of IT equipment, the racks being arranged in multiple parallel rows. The method is so performed that the floor, the racks, and the cold aisle services modules including the associated integrated blanking portions together define multiple parallel spaced apart cold aisles for entraining and encapsulating the flows of cooling air to the IT equipment in the racks.

Preferably, the building so provided meets certain pre-defined criteria, for example criteria relating to thermal conductivity and/or air tightness of the floor, walls and roof of the building. It may be the case that the pre-specified criteria that the building must meet allow some freedom of choice as to materials used for the floor, walls and/or roof of the building of the data centre. It may be the case for example that the building of the data centre can be constructed from any suitable material, such as a preferred, locally available material. For example, it may be that the floor, walls and roof of the building are primarily constructed from metal (such as steel), from concrete, and/or from wood, provided that the pre-specified criteria are met. Using a preferred, locally available material for construction of the building may allow for more efficient construction, for example because local building contractors are familiar with the material. Furthermore, it may be that using different materials for construction in different locations makes it more straightforward to meet local building regulations and/or meet local preferences for building materials. One of the pre-specified criteria preferably includes requiring an aperture for forming an air inlet and an aperture for forming an air outlet. Alternatively, it may be the case that aperture(s) for the air inlet and/or the air outlet is/are provided after one or all of the multiple prefabricated data centre elements are installed.

It will be appreciated that the floor may be any floor of the building. For example, the floor may be the ground floor, a floor lower than the ground level floor (such as a basement floor) or a floor higher than the ground level floor (such as a first or second storey floor).

Preferably, each row of racks of IT equipment comprises at least 10 racks, for example at least 15 racks, such as at least 20 racks. Preferably, each row of racks comprises from 5 to 50 racks, for example from 10 to 40 racks, such as 15 to 30 racks.

It will be appreciated that the method may, for example, comprise providing a building that is an existing structure, such as a building not originally intended for use as a data centre. For example, the step of providing the building may include providing an existing building for conversion to a data centre. It will also be appreciated that the building may be a basement, or a natural space, such as a cavern, for example.

It may be that installing multiple prefabricated data centre elements decreases the time taken to make the data centre. For example, the prefabricated data centre elements may be fabricated while provision or construction of the building is ongoing, or even prior to construction of the building starting. Furthermore, installing multiple prefabricated data centre elements may, for example, allow some or each of the elements to be at least partially commissioned and tested 'off-site'. Off-site commissioning and testing of the elements could be carried out in a controlled environment, such as a factory, for example.

Preferably, at least some, or all, of the prefabricated data centre elements are 'plug-and-play' elements, meaning that they require no specialist tools and/or no specialist knowledge to assemble and connect together. It will be appreciated that at least some, or all, of the prefabricated data centre elements are provided with connectors or connection devices that are not 'plug-and-play' connectors, but which nevertheless allow the elements to be connected together in a convenient and efficient manner. A plug-and-play connector often comprises connection details that are adapted to allow for the quick, secure and simple connection of the plug-and-play connector to a corresponding connector. It may be that local requirements, for example building regulations or the like, specify that a skilled technician (for example a suitably qualified electrician, engineer, or other specialist) certify or otherwise inspect the connection. It may be that at least some, such as substantially all, or all, of the data centre services pre-installed on each cold aisle services module terminates in a connector facilitating connection to a corresponding connector on an adjacent data centre services module. Preferably, the cold aisle services modules can be installed and connected to adjacent data centre services modules by unskilled personnel with basic tools. It may be that providing plug-and-play connectors on the cold aisle services module lessens or removes the need for highly skilled, specialist personnel on-site, thereby reducing the cost and complexity of construction.

It may be that providing integrated blanking portions on the cold aisle services module provides a particularly quick and straightforward method of constructing a data centre having segregated hot and cold aisles. Furthermore, it may be that providing integrated blanking portions on the cold aisle services modules allows the air-tightness of the blanking portions (and the air-tightness on any joints between blanking portions on each cold aisle services module) to be tested and verified prior to installation in the data centre building. Preferably, the integrated blanking portions are made from a light-weight material. Optionally, the integrated blanking portions are made from an insulated material. For example, it may be that the integrated blanking portions are made from polycarbonate sheet, such as multiwall polycarbonate sheet (that is, hollow-bodied polycarbonate sheet). Preferably, the blanking portions comprise a light-weight material having a unit weight of from 1 to 4 $Kg/m^2$, and/or a U-value of from 1 to 4 $W/m^2K$. It will be appreciated that light-weight blanking portions may be particularly useful because they reduce the load placed on the cold aisle services module. It will be appreciated that insulated blanking portions may be particularly useful because they reduce heat transfer between air inside and outside of the aisle defined by the cold aisle services module. It may be that multiple parallel spaced apart cold aisles for entraining and encapsulating the flows of cooling air to the IT equipment in the racks are defined by means of the cold aisle services modules with integrated blanking portions, the IT racks and the floor. This may, for example, provide a particularly efficient method of constructing a data centre. It will be appreciated that by following such a method, as few as only three steps may be required in order to provide a cold aisle suitable for entraining and encapsulating cooling air: 1) providing a building with a floor, walls and a roof, 2) installing the cold aisle services modules, and 3) installing the IT racks. For at least some of the cold aisles it may be the case that no substantive structural parts, other than the floor, IT racks and cold aisle services modules mentioned above, are required in order to provide the entrainment and encapsulation of cooling air along the cold aisle.

As used herein, the term "integrated blanking portion" means a blanking portion that is configured to be supported entirely by a cold aisle services module. It may be that one or more of the integrated blanking portions are detachable from the cold aisle services module. It may be that one or more of the integrated blanking portions are transported to site separately from the cold aisle services module, and only connected to the module during installation of the module in the building.

Preferably, the cold aisle services modules each comprise at least one attachment device, such as a clamp (e.g. a hasp clamp) for attaching the cold aisle services module to an adjacent data centre services module. Additionally or alternatively, it may be that each cold aisle services module is configured to be secured to at least one other cold aisle services module with a bolt. Preferably, the cold aisle services modules each comprise at least one sealing device, such as a gasket (e.g. a rubber gasket) for providing a substantially air-tight seal between the integrated blanking portions of the cold aisle services module and the adjacent data centre services module. Preferably, the cold aisle services modules each comprise at least one locating device, such as a projection or a recess. Preferably, the at least one locating device is arranged to engage with a corresponding locating device on the adjacent data centre services module. Preferably, the locating device of the cold aisle services module and the corresponding locating device of the adjacent data centre services module are in the form of a cone-shaped projection and an inverted cone-shaped recess. Preferably, the method comprises using the locating devices on the cold aisle services module and the adjacent data centre services module to align the modules during installation. For example, the method may comprise engaging one or more locating projections on the cold aisle services module with corresponding locating recesses on the adjacent data centre services module (or vice versa) to align the modules during installation. The step of using the locating devices to align the modules may be carried out before or during attachment of the modules to the building.

Optionally, the data centre services module adjacent to a cold aisle services module is a second cold aisle services module. Preferably, the method comprises clamping together at least two cold aisle services modules using clamps (e.g. hasp clamps) provided on at least one of the cold aisle services modules. Additionally or alternatively, the method comprises bolting together at least two cold aisle services modules using bolts. Preferably, the method comprises securing together, such as clamping and/or bolting together, at least two cold aisle services modules in order to establish a substantially air-tight seal between integrated blanking portions on the at least two cold aisle services modules.

Preferably, the step of installing multiple prefabricated data centre elements includes installing one or more services distribution modules, each services distribution module having one or more data centre services terminating in a connector that is connected to a corresponding connector of a cold aisle services module. It may be that the connectors of the one or more services distribution modules and the corresponding connectors of the cold aisle services module are 'plug-and-play' connectors that require little or no specialist tools or knowledge to connect together. It will be appreciated that the services distribution modules may provide a particularly straightforward way of distributing services to the cold aisle services modules. Optionally, the data centre services module adjacent to a cold aisle services module is a services distribution module. Preferably, each services distribution module has one or more data centre services terminating in a connector that is connected to a corresponding connector on an adjacent services distribution module. Preferably, one or more of the connectors are in the form of 'plug-and-play' connectors. Preferably, the method comprises installing multiple services distribution modules in the data centre building. Preferably, the method comprises connecting each services distribution module to at least one cold aisle services module and to at least one other services distribution module.

It will be appreciated that, as used herein, the term "data centre services module" is a general term that can be used to refer to a "cold aisle services module" and/or a "services distribution module", for example. It will also be appreciated that the term "data centre services distribution module" is used to distinguish from a "cold aisle services module". It may therefore be the case that a "data centre services distribution module" is in the form of a service-carrying module which is provided for the purpose of carrying services in or above a part of the data centre other than a cold aisle.

It will be appreciated that, optionally, one or more additional services may be installed on the data centre services modules (for example on the cold aisle service modules and/or the services distribution modules) during or after installation in the building. Some services may, for example, be installed on-site.

Optionally, the step of installing the multiple cold aisle services modules comprises moving the integrated blanking portions from a first, transport, configuration to a second, deployed, configuration. It may be that the step of moving the integrated blanking portions comprises disconnecting one or more integrated blanking portions from each cold aisle services module and then reconnecting the one or more integrated blanking portions to the cold aisle services module. It will be appreciated that the blanking portions of the cold aisle services modules may be arranged such that the cold aisle services module occupies a smaller volume when the module is in the transport configuration than the volume occupied when the module is in the deployed configuration. It will be appreciated that having a smaller volume transport configuration allows the cold aisle services module to be transported more efficiently, and may also allow the integrated blanking portions to be transported in a manner in which they are protected from damage. For example, it may be that when the integrated blanking portions are in the deployed configuration, one or more of the portions extends from the body of the cold aisle services module. Transporting the cold aisle services module in such a configuration may, for example, risk damage to the extending integrated blanking portion. It may be that in the transport configuration, one or more of the integrated blanking portions that extends from the body of the cold aisle services module in the deployed configuration is detached from the cold aisle services module, is contained within the body of the cold aisle services module, or extends from the body of the cold aisle services module by a lesser amount.

Preferably, the method comprises installing one or more data centre services on the cold aisle services modules and/or the services distribution module prior to installation of the module in the building. It will be appreciated that pre-installing services on the data centre services modules prior to installation in the building may allow the services to be tested 'off-site', for example. Optionally, the method comprises installing on the cold aisle services modules and/or the services distribution module prior to installation of the module in the building at least one service selected from the list consisting of: electrical power services, data-carrying services, lighting services and fire suppression services. Preferably, the method comprises installing on the cold aisle services modules and/or the services distribution module prior to installation of the module in the building at least one item of data centre service-providing equipment selected from the list consisting of: cable trays, electrical cables, electrical power carriers (such as bus-bars or power cables), earth cables, data-carrying/network cables, fire suppression system conduits (for example, fire suppression system conduits for carrying a fire suppressant fluid, such as water or a fire suppressant gas), sensor cables (for example fire detection sensor cables, temperature sensor cables and/or humidity sensor cables), sensors (for example fire detection sensors, temperature sensors and/or humidity sensors), lighting system cables, and lighting systems (for example comprising one or more lights and/or one or more sensors for detecting the presence of a person in the aisle). Optionally, the method comprises installing components of at least one data centre service, such as data-carrying/network cables, on the cold aisle services module after the module is installed in the building. For example, when the cold aisle services module comprises a cable tray for carrying cold aisle service cables, the method optionally comprises laying network cables in the cable tray after the module is installed in the building. It will be appreciated that installing some services on a services distribution module after installation of the module in the building may, for example, allow for a greater flexibility in the provision of services, such as by allowing additional data carrying/network cables to be added if extra capacity is required. It will also be appreciated that, in some cases, not all types of data centre service equipment can be conveniently broken down into lengths corresponding to the length of a cold aisle service cassette.

As used herein, the term "earth cable" also includes earth rod (also referred to as earth tape) or any other component providing a deliberate earthing function. Similarly, "electrical cable" should be considered as encompassing rigid conducting members such as bus-bars or the like.

Preferably, the cold aisle services module is arranged to additionally carry data centre hot aisle services (that is, services that are associated with or otherwise provided for the hot aisle). Thus, the cold aisle services module advantageously functions as both a cold aisle services module and a hot aisle services module. Optionally, the cold aisle services module is arranged to carry data centre hot aisle services such as network cables, electrical cables, earth cables and/or components of a hot aisle lighting system. Preferably, the cold aisle services module comprises at least one integrated hot aisle services portion arranged to extend across and above at least part of at least one hot aisle adjacent to the cold aisle. Preferably, the at least one integrated hot aisle services portion comprises a hot aisle cable tray. Optionally, the hot aisle cable tray is installed on the at least one integrated hot aisle services portion prior to installation of the cold aisle services module in the building. Preferably, the cold aisle services module comprises two or more integrated hot aisle services portions, wherein one integrated hot aisle services portion is arranged to extend across and above at least part of an adjacent hot aisle on one side of the cold aisle, and another integrated hot aisle services portion is arranged to extend across and above at least part of another adjacent hot aisle on the other side of the cold aisle. Preferably, the method comprises moving the at least one integrated hot aisle services portion from a first, transport, configuration to a second, deployed, configuration. It may be that the step of moving the at least one integrated hot aisle services portion comprises disconnecting an integrated hot aisle services portion from the cold aisle services module and then reconnecting the integrated hot aisle services portion to the cold aisle services module. It will be appreciated that the at least one integrated hot aisle services portion of the cold aisle services module may be arranged such that the cold aisle services module occupies a smaller volume when the at least one integrated hot aisle services portion is in the transport configuration than the volume occupied when the at least one integrated hot aisle services portion is in the deployed configuration.

Preferably, the cold aisle services module has a width of from 2 to 5 metres, for example a width of from 2 to 4 metres when in its transport configuration. Preferably, the cold aisle services module has a width of from 3 to 6 metres, for example a width of from 4 to 6 metres when in its deployed configuration. Preferably, the cold aisle services module has a height of from 0.3 metres to 1 metre. Preferably, the cold aisle services module has a height of from 0.3 to 0.8 metres when in its transport configuration and a height of from 0.5 metres to 1 metre when in its deployed configuration, such as a height of about 0.5 metres when in its transport configuration and a height of about 0.7 metres when in its deployed configuration.

As used herein, the "transport configuration" of the cold aisle services module refers to a reduced volume configuration of the cold aisle services module in which at least one integral blanking portion is arranged in a first transport position or is detached from the module and/or in which at least one integral hot aisle services portion is arranged in a first transport position or detached from the module. As used herein, the "deployed configuration" of the cold aisle services module refers to a larger volume configuration of the cold aisle services module in which at least one integral blanking portion is arranged in a second deployed transport position or is attached to the module and/or in which at least one integral hot aisle services portion is arranged in a second deployed position or attached to the module.

It may be that the building so provided additionally comprises two or more floors at different levels, for example a floor at ground level, a floor at basement level and/or a floor at first or second storey level. When the building comprises two or more floors at different levels, it may be that the method comprises installing the prefabricated data centre elements on any one of the levels of the building. Preferably, the method comprises installing the prefabricated data centre elements on a different floor (i.e. different level) of the building after prefabricated data centre components and IT racks have been installed on one of the floors of the building. It will be appreciated that the method allows the data centre to be conveniently increased in size and capacity in line with changing capacity requirements.

Preferably, the method comprises defining an air supply corridor (which may, for example, be referred to as a cold corridor) for transporting cooling air above the floor from the air handling module to the cold aisles. Preferably, the air supply corridor has a height of at least 1.5 m, such as at least 2.5 m, above the floor. Preferably, the air supply corridor is defined at least partially by a wall of the building. Preferably, the method comprises installing one or more services distribution modules in the air supply corridor. Preferably, the air supply corridor and the cold aisles provide personnel access to the IT equipment in the racks. Preferably, the air supply corridor is a personnel corridor allowing human access to an area of the data centre.

Preferably, the method is so performed that the floor, the IT racks, the cold aisle services modules including the associated integrated blanking portions, and optionally the roof, together define multiple parallel spaced apart hot aisles interleaved between the multiple parallel cold aisles, the hot aisles being provided for entraining and encapsulating the flows of warm air from the IT equipment in the racks.

Preferably, the step of installing multiple prefabricated data centre elements includes installing a vented door assembly for each cold aisle. Optionally, each vented door assembly is a prefabricated vented door assembly comprising a frame and a door for providing personnel access from the air supply corridor to the cold aisle. Preferably, the door comprises at least one controllable vent for regulating the flow of cooling air into the cold aisle from the air supply corridor. Optionally, each vent comprises a plurality of adjustable louvres. Preferably, each vented door assembly comprises at least one actuator connected to the adjustable louvres and arranged to adjust the position of the adjustable louvres in order to control the flow of cooling air through the vent. Preferably, each vented door assembly is provided pre-wired and ready for connection to the data centre control system. Optionally, each vented door assembly comprises an aperture for accommodating one or more connectors between a services distribution module located in the cold corridor and a cold aisle services module located in the cold aisle. Optionally, the step of connecting the services of the services distribution module to the corresponding services of the cold aisle services module comprises passing a connector, such as a services distribution module connector, through the aperture of the vented door assembly.

Preferably, the air supply corridor is defined at least partially by the floor and a wall, and optionally the roof, of the building. Preferably, the air supply corridor is also defined at least partially by the multiple vented door assemblies.

Preferably, the method comprises supporting the prefabricated data centre elements on or from the structure of the building. Optionally, the method comprises suspending the multiple cold aisle service modules from the structure of the building, for example from the roof of the building. Additionally or alternatively, the method comprises suspending the services distribution modules from the structure of the building, for example from the roof of the building. Optionally, the method comprises supporting the vented door assembly on the floor of the building. Optionally, the method comprises supporting the one or more damper units on the floor of the building. Optionally, the method comprises supporting the air handling module on the floor of the building.

Optionally, the method comprises a step of installing a first data centre services module in the building prior to the installation of any other data centre services modules, wherein the installation comprises suspending the first data centre services module from the structure of the building. Preferably, the step of installing the first data centre services module comprises specifying a three-dimensional position for the first data centre services module in the building, and locating the first data centre services module at the specified position. Optionally, the step of specifying a three-dimensional position comprises specifying the location of one or more fixing points on the structure of the building. It may be that, for example, the step of locating the first data centre services module in the building comprises providing one or more fixing points on the structure of the building for attaching the module, and/or attaching the module to said fixing points. Optionally, the method comprises specifying a position for one or more other data centre services modules relative to the position of the first data centre services module (for example, specifying positions for a plurality of other data centre services modules relative to the position of the first data centre services module), and locating the one or more other data centre services modules at the specified position relative to the first data centre services module. It may be that when the method comprises specifying a first three-dimensional location for the first data centre services module and then specifying positions for one or more other data centre services modules relative to the position of the first data centre services module, the installation of the modules can be carried out particularly quickly and simply. Optionally, the first data centre services module is a first services distribution module, and the method optionally comprises specifying the location of at least one other services distribution module and/or at least one cold aisle services module relative to the position of the first services distribution module. Additionally or alternatively, it may be that the first data centre services module is a first cold aisle services module, and the method optionally comprises specifying the position of at least one other cold aisle services module and/or at least one services distribution module relative to the position of the first cold aisle services module. Optionally, the specified three dimensional position of the first data centre services module is expressed in x, y and z coordinates along respective x, y and z axes. It will be understood that the x, y and z axes are pairwise perpendicular axes (in other words, the axes form a Cartesian coordinate system). It may be that the z coordinate is the height of the module above the floor of the building. When the first data centre services module is a first services distribution module, the x coordinate may be, for example, the position of the module across the width of the air supply corridor, and the y coordinate may be, for example, the position of the module along the length of the air supply corridor. When the first data centre services module is a first cold aisle services module, the x coordinate may be, for example, the position of the module across the width of the cold aisle, and the y coordinate may be, for example, the position of the module along the length of the cold aisle. Preferably, the step of specifying a three dimensional position for the first data centre services module comprises specifying x, y and z coordinate positions relative to one or more parts of the building structure. For example, it may be that the method comprises specifying a z coordinate relative to the floor of the building (e.g. vertical distance from the floor), specifying an x coordinate relative to a wall or column of the building (e.g. distance from the wall or column in a first direction parallel to the floor), and/or specifying a y coordinate relative to a wall or column of the building (e.g. distance from the wall or column in a second direction parallel to the floor, the second direction being perpendicular to the first direction). Optionally, the step of locating the first data centre services module comprises verifying the x, y and z coordinate positions of the module (i.e. comparing the actual to the specified x, y and z coordinate positions). It may be that, for example, the step of verifying the position of the module comprises verifying the location of the one of more pre-specified fixing points, such as by attaching the module to said fixing points and checking that the module is in the expected location. Preferably, the method comprises connecting (e.g. releasably attaching) at least one laser level device to the first data centre services module and using the laser level device to verify at least one of the x, y and z coordinate positions of the module. Optionally, the laser level device is a cross-line laser level device that projects two laser lines along a pair of perpendicular planes. It may be that such a cross-line laser level allows at least two of the x, y and z coordinate positions of the module to be verified simultaneously. For example, it may be that the method comprises measuring the distance between each laser line and a defined structural element of the building (e.g. the floor and/or the corner or some other part of a wall or column in the building). Preferably, the data centre services module is provided with at least one, for example a plurality of, connection point(s) (e.g. connection points defined during manufacture of the module) for connecting the laser level device to the module, for example in the form of a threaded bore configured for receiving a threaded projection on the laser level. It may be that providing such connection points allows the relative position of the laser level on the module to be specified during manufacture of the module, thus reducing errors in positioning the laser level during installation of the module in the building. Optionally, the method also comprises using the laser level to verify the orientation of the module. Optionally, the at least one laser level is a self-levelling laser level. Preferably, when the at least one laser level is a self-levelling laser level, the method comprises connecting at least two self-levelling laser levels to the module, such as to at least two connection points on the module. It will be appreciated that the relative positions of laser lines of the at least two self-levelling laser levels can be used to check the orientation of the module.

The cold aisle services module may have a mass of at least 100 Kg. The cold aisle services module may have a mass of at least 200 Kg. The services distribution module, if provided, may have a mass of at least 100 Kg. The services distribution module, if provided, may have a mass of at least 200 Kg.

Preferably, the pre-specified criteria for the building include specified fixing locations for fixing the prefabricated data centre elements to the building. Preferably, the pre-specified criteria for the building include specified fixing locations for the cold aisle services modules and/or the data centre services module to the building. Preferably, the method comprises providing a building having pre-specified fixing locations for affixing the cold aisle services modules and/or the data centre services module to the building. Optionally, the fixing locations are in the form of elongate members, for example elongate members having a slot for engaging with engagement means provided on the modules. Preferably, the elongate member fixing locations are horizontally arranged elongate member fixing location, for example arranged substantially parallel to the plane of the floor. It will be appreciated that elongate members may spread the load across the structure of the building. Preferably, the method comprises providing a template for checking that the fixing locations provided on the building are correctly located. Optionally, the method comprises using a template to check that fixing locations are provided on the building in accordance with the pre-specified criteria prior to installation of at least some of, optionally all of, the multiple prefabricated data centre elements. Preferably, the method comprises fixing at least some of, optionally all of, the multiple prefabricated data centre elements to the fixing locations provided on the building. Preferably, the fixing locations are in the form of fixing points, such as suspension points suitable for suspending a load, and/or supporting points suitable for supporting a load. Preferably, when the fixing locations are in the form of fixing points for suspending a load, three or more fixing points are provided for each module. For example, the method optionally comprises at least one of: suspending the multiple cold aisle services modules from fixing points provided on the building, and/or suspending the adjacent data centre services module (such as a services distribution module) from fixing points provided on the building. Preferably, the pre-specified criteria for the building include specified load tolerances for the building, preferably specified load tolerances for the specified fixing locations. For example, the pre-specified criteria optionally include specified hanging load tolerances for the fixing points provided on the building for supporting the cold aisle services modules and/or the data centre services module. It may be that pre-specifying fixing positions and/or fixing point load tolerances provides a more efficient method of constructing a data centre, for example because the building is provided ready for immediate installation of the prefabricated data centre components as soon as they arrive on site. Preferably, the pre-specified criteria for the building include providing a set of fixing locations for suspending each data centre services module from the structure of the building (e.g. the roof), wherein the set of fixing locations provided for each data centre services module has a load capacity of at least 150 Kg, optionally at least 200 Kg, for example at least 250 Kg, and possibly more than 400 Kg. Each fixing location in the set may have a load capacity of at least 50 Kg, optionally at least 100 Kg, for example at least 150 Kg, and possibly more than 200 Kg. Optionally, the pre-specified criteria for the building include providing a set of fixing locations for suspending each cold aisle services module, wherein each set of fixing locations provided for each cold aisle services module has a load capacity of at least 150 Kg, optionally at least 200 Kg, for example at least 250 Kg, and possibly more than 400 Kg. Each fixing location in the set may have a load capacity of at least 50 Kg, optionally at least 100 Kg, for example at least 150 Kg, and possibly more than 200 Kg. Optionally, the pre-specified criteria for the building include providing a set of fixing locations for suspending each services distribution module, wherein each set of fixing locations provided for each services distribution module has a load capacity of at least 150 Kg, optionally at least 200 Kg, for example at least 250 Kg, and possibly more than 400 Kg. Each fixing location in the set may have a load capacity of at least 50 Kg, optionally at least 100 Kg, for example at least 150 Kg, and possibly more than 200 Kg. Preferably, the pre-specified criteria for the building include providing at least one fixing location (for example one or more fixing points) on the floor for supporting and/or affixing the vented door assembly, and providing at least one fixing location for securing the top of the vented door assembly. Preferably, the pre-specified criteria for the building include providing at least one set of fixing locations (for example one or more fixing points) on the floor for supporting and/or affixing the air handling module, for example at least one set of fixing locations having a load capacity of at least 8,000 Kg. Preferably, the pre-specified criteria for the building include providing at least one fixing location on the building for supporting and/or affixing the one or more damper units, for example at least one fixing location having a load capacity of at least 400 Kg.

Preferably, the fixing locations provided for suspending the data centre services modules are in the form of eyelets or rails.

Preferably, the pre-specified criteria for the building include a load-bearing capacity of the floor of the building. Preferably, the method comprises specifying that the floor of the building has a load capacity of at least 8 KN/m$^2$, for example at least 12 KN/m$^2$, in areas of the building arranged to accommodate IT equipment and/or specifying that the floor of the building has a load capacity of at least 3 KN/m$^2$ in areas of the building not arranged to accommodate IT equipment. Preferably, the building is constructed to resist earthquake damage.

It will be appreciated that the buildings of modern data centres, especially data centres that use adiabatic evaporative cooling to provide cooling air to IT equipment, often need to meet uniquely stringent requirements in areas such as the thermal conductivity of the building envelope and the air tightness of the building envelope. Adiabatic evaporative cooling methods typically cool air by evaporating water into a 'warm' air stream (for example using a water sprayer or a wetted matrix) thus providing a 'cool' air stream having a lower temperature and a higher humidity. Data centres having hot and cold area segregation, for example comprising cold aisles and hot aisles, often operate with a positive air pressure in the cold area making cold air available to pass through the servers and into the hot area, and to reducing areas of dead air which can lead to hot spots or to the backward flow of warm air from the hot area to the cold area. A high level of attention to detail in building design is often necessary to correctly handle the pressurised cool humid air in the cold area.

IT equipment manufacturers typically specify minimum and maximum cooling air humidity levels and minimum and maximum temperature levels. If the humidity of the cooling air is too low, the IT equipment may be compromised by static discharge, whereas if the humidity is too high the IT equipment may be compromised by excess moisture coming into contact with the IT equipment. Similarly, cooling air temperatures that are too hot or too cold may compromise IT equipment components.

A typical direct free air cooling data centre may comprise an air handling module having fans that draw in ambient air from outside the data centre building and push it into a cold area within the data centre. The air handling module may, depending on the temperature and humidity of the ambient air, add moisture to the ambient air to cool it (and thus humidify it) before the air is pushed into the cold area. As it passes through the IT equipment, the cold air is typically heated without any substantial change to its moisture content, and then passes into the warm area. Typically, all or some of the hot air is exhausted from the building. Often, such data centres are constructed in relatively cool climates where the ambient air temperature is frequently cold enough to allow the data centre to operate in a free air cooling regime. In many locations, it is likely that there will be times of the year where the ambient air outside the data centre will be too cold for direct use as data centre cooling air. The air may be too cold for the IT equipment, or perhaps too cold to provide a comfortable working environment for personnel in the data centre. In such situations, some data centres are configured so that all or some of the hot air in the warm area is sent back to the air handling module to be mixed with fresh ambient air, and optionally conditioned) before being recirculated to the IT equipment. When operating in such a mode, it may be that the cold air in the cold area of the data centre has a temperature that is higher than ambient air outside the data centre and has a relatively higher humidity (for example higher than ambient air outside the data centre). Since the cooling air is usually heated by the IT equipment without any change in humidity, the hot air in the hot area of the data centre also has a temperature and a relatively high humidity.

The temperature below which moisture in air condenses to form water droplets is known as the dew point. As the humidity of air increases, so does its dew point, meaning that the moisture in more humid air tends to condense at a higher temperature than moisture in less humid air. Approximate dew points for air with varying relative humidity are set out in Table 1, the air being at atmospheric pressure at sea level.

TABLE 1

| Relative Humidity (%) | Dew Point (° C.) |
|---|---|
| ≤25 | <10 |
| 26-30 | 10-12 |
| 31-36 | 13-16 |
| 37-43 | 16-18 |
| 44-51 | 18-21 |
| 52-61 | 21-24 |
| 62-72 | 24-26 |
| ≥73 | >26 |

One source of guidelines for acceptable ranges of cooling air temperature and humidity in data centres is ASHRAE (the American Society of Heating, Refrigerating and Air-Conditioning Engineers). ASHRAE's 2011 publication "Thermal Guidelines for Data Processing Environments—Expanded Data Center Classes and Usage Guidance" provides various acceptable and preferred ranges of data centre cooling air temperature and humidity. That set of guidelines is an update on earlier editions issued in 2004 and 2008. With each new edition, ASHRAE have revised upwards the maximum temperature and maximum humidity acceptable for data centre cooling air. Those revisions result from more relaxed manufacturer guidelines for IT equipment and from a desire to reduce data centre energy consumption. ASHRAE's 2011 guidelines indicate that a cooling air dry bulb temperature range of from 15° C. to 45° C. and a cooling air relative humidity range of from 8% to 90% is allowable for certain types of data centre (depending on the type of IT equipment in the data centre), and that a cooling air dry bulb temperature range of 18° C. to 27° C. and a cooling air relative humidity range of from 20% to 60% is recommended.

It will be appreciated from the data in Table 1 and from the ASHRAE 2011 guidelines that even when a data centre is operating within the recommended ASHRAE cooling air relative humidity range, the dew point of the cooling air in the cold area of the data centre may be significantly higher than the temperature of the air outside the data centre. Therefore, the thermal conductivity of a data centre building may need to be specified more rigorously than for other types of building to avoid internal surfaces in the building having a surface temperature below the dew point of the air inside the data centre. Furthermore, the positive pressurisation of the cold area of the data centre presents further particular consideration in data centre building construction, and it may be that the air tightness of a data centre building is specified more rigorously than for other types of building. For example, some data centres present a unique requirement for the building to contain pressurised cold and relatively humid air in an environment having even colder air outside. In such a situation, ingress of the pressurised humid cooling air into the fabric of the building through even only very small openings or gaps in the walls of the building, for example, can lead to interstitial condensation, for example within a wall cavity. Furthermore, while a data centre wall may have very high levels of insulation when considered as a whole, localised areas of poor insulation can cause localised areas of internal condensation.

A particular consideration in certain embodiments of the present invention, for example relating to a free air cooling data centre with direct or indirect air cooling, is to avoid 'cold bridging'. Cold-bridging is a recognised phenomenon in building construction that can occur if there are thermally conductive elements of the building structure which are not appropriately insulated. Internal surfaces of the building at cold-bridging locations may be at a temperature that is lower than the dew point of the cooling air when the ambient air outside the building is below the dew point, causing water to condense on the surface when cooling air comes into contact with it. By way of an example, the wall of a steel frame building may have cold-bridging locations around the posts of the steel frame or at the fixing points of insulation panels. Furthermore, beams, or other supporting members, or attachment clips may penetrate the insulation provided in the structure of a data centre wall. While the overall insulation of the wall may be very good, those elements that penetrate the insulation can result in localised cold zones on the internal surface of the wall. In some areas, a cold zone may be very narrow but very long, such as where a support post within a wall is not properly insulated. Additional examples of other sources of cold-bridging are lintels, door or window frames, and joins between walls, floors and roofs (especially joins between the ground floor and walls because it can be very difficult to link the floor insulation with the wall insulation).

Although it may be particularly important to carefully consider cold bridging risks in the cold area of a data centre, for certain weather conditions and for certain modes of operation (such as when the IT load in the data centre in low), localised cold-bridging in the hot area of the data centre may also need careful consideration.

As used herein, the "cold area" of the data centre will be understood to mean those sections of the data centre through which cooling air flows from the air handling module to the IT equipment, and may include, for example, an air supply corridor and one or more cold aisles. As used herein, the "hot area" of the data centre will be understood to mean those sections of the data centre through which warm air from the IT equipment flows, and may include, for example, an air exhaust corridor and one or more hot aisles.

The thermal properties of a building element can be expressed in a number of ways. One approach is to refer to a building element's U-value, which is an overall heat transfer coefficient that describes how well a building element conducts heat, or the rate of transfer of heat in Watts through one square metre of a structure divided by the difference in temperature across the structure. The smaller the U-value (expressed in $W/m^2K$) the better the element is at reducing heat transfer. Another approach is to refer to an element's R value, which is a measure of thermal resistance. A material's R value is the ratio of the temperature difference across an insulator and the heat flux (heat transfer per unit area per unit time) under standard conditions. The higher the R value (expressed in $m^2K/W$), the better an element is at reducing heat transfer. An element's R value is the inverse of its U-value.

Preferably, the method comprises providing a building meeting certain pre-specified criteria including thermal conductivity and/or air tightness criteria.

Preferably, the method comprises providing a building in which all elements of the building arranged to define a surface in a cold area and/or hot area of the data centre are sufficiently thermally insulated from the ambient air outside the data centre to prevent condensation of water on any part of said surface when the air inside the data centre has a relative humidity of at least 40%, for example at least 60%, such as at least 80%, and when the temperature of the ambient air outside the data centre is at a certain cold outside temperature. The certain cold outside temperature may for example be the typical average temperature of the coldest month for the location in which the data centre is situated. The certain cold outside temperature may for example be at 5° C. below the typical average temperature of the coldest month for the location in which the data centre is situated. The certain cold outside temperature may for example be at 10° C. below the typical average temperature of the coldest month for the location in which the data centre is situated. The certain cold outside temperature may for example be −5° C. The certain cold outside temperature may for example be −10° C. The certain cold outside temperature may for example be −15° C. The certain cold outside temperature may for example be −20° C. The certain cold outside temperature may for example be −25° C. The certain cold outside temperature may for example be −30° C. It will be appreciated that the design criteria for a given data centre will vary according to the location of the data centre. It will be appreciated that, as used herein, the location of the data centre may be the general geographical area of the data centre rather than its precise location. As used herein, the average month temperature is the mean average taken from the minimum temperature recorded for each 24 hour period in a given month. As used herein, the coldest month is the month of a given year having the lowest average month temperature. As used herein, the typical average temperature of the coldest month is the mean average of the average temperature of the coldest month for each year in the previous 100 years, for example the years 1916 to 2015. It may be that the above criteria additionally specify that condensation need be prevented when the air in the cold area and/or hot area of the data centre is at or above a certain temperature. For example, the above criteria may additionally specify that condensation is prevented when the temperature of the air in the cold area of the data centre is at a certain cold area internal air temperature, for example meeting the ASHRAE criteria. The certain cold area internal air temperature may be 18° C. The certain cold area internal air temperature may be 24° C. The certain cold area internal air temperature may be 28° C. The above criteria may additionally specify that condensation is prevented when the temperature of the air in the hot area of the data centre is at a certain hot area internal air temperature. The certain hot area internal air temperature may be 30° C. The certain hot area internal air temperature may be 35° C. The certain hot area internal air temperature may be 40° C. It will be appreciated that for an element to be "sufficiently thermally insulated" to prevent condensation on any part of the surface defined in a cold area or a hot area, the element should be sufficiently insulated for the surface to stay above the dew point temperature of the air in the cold area or the hot area. It may be that the elements of the building that are arranged to define a surface in the cold area or the hot area are sufficiently thermally insulated to prevent condensation of water if no region greater than 10×10 cm, such as no region greater than 10 cm², for example no region greater than 1 cm², of said surface has a surface temperature at or lower than the dew point of the air in the relevant area of the data centre when the temperature outside the data centre is at or above the relevant temperature.

Preferably, the method comprises providing a building having external walls and a roof, wherein all sections of the external walls and the roof that are arranged to define a surface in a cold area of the data centre have an average U-value of no more than 0.35 W/m²K, for example no more than 0.25 W/m²K, such as no more than 0.15 W/m²K. Preferably, said sections of the external walls and roof are configured such that there is no portion extending from an interior surface in the cold area of the building to the exterior of the building and having a small cross-sectional area (such as 1 cm², or 10 cm² or alternatively 10×10 cm) with a U-value greater than 2.0 W/m²K, for example greater than 1.0 W/m²K, such as greater than 0.5 W/m²K. Preferably, the method comprises providing a building having a floor, wherein all sections of the floor that are arranged to define a surface in a cold area of the data centre have a U-value of no more than 0.30 W/m²K, for example no more than 0.20 W/m²K, such as no more than 0.10 W/m²K. Preferably, said sections of the floor have no portion extending from the interior surface of the floor to the exterior and having a small cross-sectional area (such as 1 cm², or 10 cm², or alternatively 10×10 cm) in the cold area with a U-value greater than 1.5 W/m²K, for example greater than 0.75 W/m²K, such as greater than 0.5 W/m²K.

Preferably, the method comprises providing a building having external walls and a roof, wherein all sections of the external walls and the roof that are arranged to define a surface in a hot area of the data centre have a U-value of no more than 0.5 W/m²K, for example no more than 0.4 W/m²K, such as no more than 0.2 W/m²K. Preferably, said sections of the external walls and roof are configured such that there is no portion extending from an interior surface in the hot area of the building to the exterior of the building and having a small cross-sectional area (such as 1 cm², or 10 cm², or alternatively 10×10 cm) with a U-value greater than 2.5 W/m²K, for example greater than 1.5 W/m²K, such as greater than 1.0 W/m²K. Preferably, the method comprises providing a building having a floor, wherein all sections of the floor that are arranged to define a surface in a hot area of the data centre have a U-value of no more than 0.4 W/m²K, for example no more than 0.3 W/m²K, such as no more than 0.1 W/m²K. Preferably, said sections of the floor have no portion extending from the interior surface of the floor to the exterior and having a small cross-sectional area (such as 1 cm², or 10 cm², or alternatively 10×10 cm) in the hot area with a U-value greater than 2.0 W/m²K, for example greater than 1.0 W/m²K, such as greater than 0.5 W/m²K.

It will be appreciated that air tightness of the cold area of the data centre, and also the hot area in some cases, is an important issue for efficient data centre operation. In addition to the potential problems of interstitial condensation that can arise if humid air inside the data centre is able to penetrate the building's insulation, air leakage out of the cold area of the data centre in particular can result in the data centre's air-moving devices having to run at a higher than necessary load. For example, where the air handling module comprises one or more fans for transporting cooling air from the air handling module to the IT equipment, excessive air leakage from the cold area of the data centre either to other parts of the building or even to outside the building can result in degradation of the fan's air-transporting ability. One method of expressing air tightness is to refer to fan power degradation. As used herein, a fan power degradation of 10% in the cold area of the data centre, for example, means that the fans of the air handling module need to operate at a power setting 10% higher than they would have to work if there was zero air leakage in the cold area of the data centre in order to transport the same amount of air to the IT equipment. Another method of expressing air tightness is to refer to air permeability, which is typically expressed in m³/m²h at a pressure of 50 Pa.

Preferably, the method comprises providing a building wherein all elements of the building arranged to define a surface in a cold area and/or hot area of the data centre are sufficiently air-tight to provide a fan power degradation of no more than 5%, such as no more than 2%, for example no more than 1%.

Preferably, the method comprises providing a building having external walls and a roof, wherein all sections of the external walls and the roof that are arranged to define a surface in a cold area of the data centre have an average air permeability of no more than 3 m³/m²h at 50 Pa, for example no more than 1 m³/m²h at 50 Pa, such as no more than 0.1 m³/m²h at 50 Pa. Preferably, said sections of the external walls and roof have no region arranged to define a 10×10 cm part, optionally a 10 cm² part, preferably a 1 cm² part, of a surface in the cold area with and air permeability of greater than 5 m³/m²h at 50 Pa, such as greater than 3 m³/m²h at 50 Pa, for example greater than 0.5 m³/m²h at 50 Pa. Preferably, the method comprises providing a building having a floor, wherein all sections of the floor that are arranged to define a surface in a cold area of the data centre have an air permeability of no more than 1 m³/m²h at 50 Pa, for example no more than 0.5 m³/m²h at 50 Pa, such as no more than 0.1 m³/m²h at 50 Pa. Preferably, said sections of the floor have no region arranged to define a 10×10 cm part, optionally a 10 cm² part, preferably a 1 cm² part, of a surface in the cold area with and air permeability of greater than 3 m³/m²h at 50 Pa, such as greater than 0.5 m³/m²h at 50 Pa, for example greater than 0.2 m³/m²h at 50 Pa.

Preferably, the method comprises providing a building having external walls and a roof, wherein all sections of the external walls and the roof that are arranged to define a surface in a hot area of the data centre have an average air permeability of no more than 5 m³/m²h at 50 Pa, for example no more than 3 m³/m²h at 50 Pa, such as no more than 0.5 m³/m²h at 50 Pa. Preferably, said sections of the external walls and roof have no region arranged to define a 10×10 cm part, optionally a 10 cm² part, preferably a 1 cm² part, of a surface in the hot area with an air permeability of greater than 10 m³/m²h at 50 Pa, such as greater than 5 m³/m²h at 50 Pa, for example greater than 1 m³/m²h at 50 Pa. Preferably, the method comprises providing a building having a floor, wherein all sections of the floor that are arranged to define a surface in a hot area of the data centre have an air permeability of no more than 3 m³/m²h at 50 Pa, for example no more than 1 m³/m²h at 50 Pa, such as no more than 0.5 m³/m²h at 50 Pa. Preferably, said sections of the floor have no region arranged to define a 10×10 cm part, optionally a 10 cm² part, preferably a 1 cm² part, of a surface in the hot area with and air permeability of greater than 5 m³/m²h at 50 Pa, such as greater than 1 m³/m²h at 50 Pa, for example greater than 0.5 m³/m²h at 50 Pa.

It will be appreciated that the term "all sections of the external walls and the roof of a building that are arranged to define a surface" includes, for example, any joins between walls and between walls and the roof that define a surface. It will be appreciated that the term "all elements of the building arranged to define a surface" includes, for example, any joins between walls, between walls and floors and between walls and the roof that define a surface.

As used herein, "a section" of an external wall of a building that is arranged to define a surface in a cold area or hot area in the data centre includes that entire section of wall, including any window or door provided in the wall. For example, if one side of a (cold) air supply corridor is defined by an external wall of the data centre building, and if windows and a door are provided in the external wall along the side of the air supply corridor, the section of the external wall that defines that side of the air supply corridor includes the windows and the door. In other words, any element of an external wall that defines a surface in the cold or hot area of the data centre is included in the term "section of an external wall" as used herein. If it is necessary to provide a door in an external wall that defines a surface in a cold or hot area of the data centre building, it may be that an appropriate U-value for the door is obtained by using an air-lock system. In such cases, the U-value of the whole air lock system may be used in determining the U-value of the relevant section of the external wall.

The surface defined by the elements of the building preferably comprises all of the interior surface that is in contact with air in the cold area and which has a corresponding exterior surface which is in contact with the ambient air outside the building. Said elements of the building are thus ones which define the separation between outside and inside the building. The surface defined by the elements of the building preferably comprises all of the interior surface that is in contact with air in the hot area and which has a corresponding exterior surface which is in contact with the ambient air outside the building. The elements of the building defining the interior surface may for example comprise all those parts that form the skin of the building, the interior of which skin forming the interior surface and the exterior of which skin forming an exterior surface of the building. Said elements of the building may collectively have a thickness, at any given location, which extends from the interior surface to the exterior surface of the building. Said elements of the building may comprise exterior walls, ceilings and/or roofs of the building.

Preferably, the pre-specified criteria for the building include a minimum weatherproofing level for the floors, walls and roof of the building.

Preferably, the pre-specified criteria for the building include providing an obstruction-free space for the air handling module. It will be appreciated that an obstruction-free space is a space free from any obstruction such as structural pillars or beams of the building. Preferably, the space provided for the air handling module has a length of at least 5 metres, such as at least 6 metres. Preferably, the space provided for the air handling module has a width of at least 3 metres, such as at least 4 metres. Preferably, the space provided for the air handling module has a height of at least 1.5 metres, such as a height of at least 2.5 metres.

Preferably, the pre-specified criteria for the building include providing an internal space having a length and a width of at least 10 metres, such as a width of at least 10 metres and a length of at least 15 metres. Preferably, the criteria include a building having an open space of at least 10 metres×10 metres as measured across the floor of the space. It may be that the internal space, such as the open space, is occupied in part by parts of the structure of the building, such as pillars. Preferably, the pre-specified criteria for the building include providing an internal space, such as an open space, having a ceiling height of at least 2.5 metres above the floor, such as at least 3 metres above the floor. It will be appreciated that in certain parts of the internal space, the ceiling may be lower than 2.5 metres above the floor. Preferably, the criteria include providing an open space having a ceiling height of at least 2.5 metres, such as at least 3 metres, above the floor for at least 70%, such as at least 90%, of the area of the open space.

Preferably, the method comprises defining an air exhaust corridor for transporting warm air from the IT equipment in the racks, the air exhaust corridor being defined at least partially by the floor, and optionally the roof, of the building. Preferably, the air exhaust corridor is defined at least partially by a wall of the building. Preferably, the wall of the building defining at least part of the air exhaust corridor comprises an air outlet for allowing warm air from the IT equipment in the racks to exit the building. Preferably, the method comprises a step of forming an aperture in the wall defining at least part of the air exhaust corridor, the aperture being an aperture for forming an air outlet. Preferably, the method comprises installing one of the one or more damper units in the building aperture for forming an air outlet. Preferably, the damper unit installed in the air outlet building aperture comprises a controllable vent, wherein the controllable vent is configured for regulating the flow of warm air out of the building. Optionally, the pre-specified criteria include minimum and maximum dimensions for the air outlet aperture that correspond to the dimensions of the one or more damper units to be installed in the aperture. Optionally, the, or each, damper unit is a prefabricated damper unit comprising a frame, a plurality of adjustable louvres mounted on the frame, and at least one actuator connected to the adjustable louvres and arranged to adjust the position of the adjustable louvres in order to control the flow of warm air through the aperture. Preferably, the controllable vent is substantially continuously adjustable between fully open and fully closed positions. Preferably, the, or each, damper unit is provided pre-wired and ready for connection to the data centre control system. Optionally, the, or each, damper unit is provided with one or more temperature and/or humidity sensors for measuring the temperature and/or humidity of warm air exiting the data centre prior to installation in the air outlet aperture. It will be appreciated that using a prefabricated damper unit may allow the damper unit to be commissioned and tested off-site, for example in a controlled environment such as a factory. Preferably, the, or each, damper unit comprises connectors, such as 'plug-and-play' connectors, for connecting the at least one louvre actuator, and the one or more sensors if present, to the data centre control system. Preferably, the method comprises connecting the louvre actuator, and the one or more sensors if present, to a data centre services module.

Preferably, the step of installing the one or more damper units in the building comprises installing one or more prefabricated damper units in the aperture for forming an air inlet. Preferably, the damper unit installed in the air inlet building aperture comprises a controllable vent, wherein the controllable vent is configured for regulating the flow of outside air into the building. Preferably, the controllable vent is substantially continuously adjustable between fully open and fully closed positions. Optionally, the method comprises specifying minimum and maximum dimensions for the air inlet aperture that correspond to the dimensions of the one or more damper units to be installed in the aperture. Optionally, the, or each, damper unit is a prefabricated damper unit comprising a frame, a plurality of adjustable louvres mounted on the frame, and at least one actuator connected to the adjustable louvres and arranged to adjust the position of the adjustable louvres in order to control the flow of outside air through the aperture. Preferably, the, or each, damper unit is provided pre-wired and ready for connection to the data centre control system. Optionally, the, or each, damper unit is provided with at least one sensor, such as one or more temperature and/or humidity sensors for measuring the temperature and/or humidity of outside air entering the building, and/or one or more smoke detection sensors, wherein the at least one sensor is provided on the damper unit prior to installation of the unit in the air inlet aperture. It will be appreciated that using a prefabricated damper unit may allow the damper unit to be commissioned and tested off-site, for example in a controlled environment such as a factory. Preferably, the, or each, damper unit comprises connectors, such as 'plug-and-play' connectors, for connecting the at least one louvre actuator, and the one or more sensors if present, to the data centre control system. Preferably, the method comprises connecting the louvre actuator, and the one or more sensors if present, to a data centre services module.

Preferably, the air inlet aperture and the air outlet aperture are separate apertures. Optionally, the, or each, air inlet aperture, if provided in the same wall of the building as the air outlet aperture, is spaced apart from the, or each, air outlet aperture by at least 8 metres, for example at least 10 metres. Preferably, the pre-specified criteria include specifying that the air inlet aperture and the air outlet aperture are separated by at least 8 metres, such as at least 10 metres.

Preferably, the air handling module comprises an external air intake for receiving external air from outside the building. Preferably, the air handling module comprises a recirculated air inlet for receiving recirculated warm air from the items of IT equipment in the racks. Preferably, the method comprises connecting the recirculated air inlet to the hot aisles, optionally via the air exhaust corridor if present. Optionally, the air handling module comprises an air inlet that is arranged for receiving both external air from outside the building and recirculated warm air from the items of IT equipment in the racks. Optionally, the method comprises connecting the external air intake of the air handling module to the air inlet aperture of the building. Optionally, at least one of the one or more damper units for controlling the flow of air between the interior and the exterior of the building is an integral part of the air handling module. For example, it may be that the method comprises connecting the air handling module to an air inlet aperture of the building, wherein the air handling module comprises an integral damper unit for controlling the flow of air into the building. Optionally, the one or more damper units for controlling the flow of air into the building are separate from the air handling module. For example, it may be that the method comprises connecting one or more damper units for controlling the flow of air into the building to an air inlet aperture of the building, and arranging the air handling module to receive said air flowing into the building.

Preferably, the air handling module comprises a cooling air outlet arranged to allow IT equipment cooling air to exit the air handling module. Preferably, the method comprises connecting the cooling air outlet of the air handling module to the cold aisles. Preferably, the method comprises connecting the cooling air outlet of the air handling module to the air supply corridor, and thus to the cold aisles.

Preferably, the method comprises supporting the air handling module on the structure of the building, for example supporting the air handling module on the floor of the building. Preferably, the method comprises specifying a position for the air handling module in the building. Preferably, the pre-specified criteria include specified positions for internal openings in the building to allow air to be transported around the data centre above the floor. Preferably, the pre-specified criteria include specified internal openings in the building to allow cooling air to be transported from the air handling module to the items of electronic equipment entirely above the floor. It will be appreciated that transporting air entirely above the floor means that the method preferably comprises defining an air flow path from the air handling module to the items of electronic equipment such that the air flow path is above the floor of the building for the entire length of the air flow path.

Preferably, the method comprises defining an air mixing chamber for mixing warm recirculated air from the IT equipment with air from outside the building. Preferably, the pre-specified criteria include providing internal walls and openings in the internal walls to define and air mixing chamber. Preferably, the method comprises providing one or more damper units for regulating the flow of recirculated warm air from the items of IT equipment in the racks into the mixing chamber. Optionally, the, or each, damper unit is a prefabricated damper unit comprising a frame, a plurality of adjustable louvres mounted on the frame, and at least one actuator connected to the adjustable louvres and arranged to adjust the position of the adjustable louvres in order to control the flow of recirculated warm air through the aperture. Preferably, the controllable vent is substantially continuously adjustable between fully open and fully closed positions. Preferably, the, or each, damper unit is provided pre-wired and ready for connection to the data centre control system. Optionally, the, or each, damper unit is provided with one or more temperature and/or humidity sensors for measuring the temperature and/or humidity of recirculated warm air entering the mixing chamber prior to installation in the building. It will be appreciated that using a prefabricated damper unit may allow the damper unit to be commissioned and tested off-site, for example in a controlled environment such as a factory. Preferably, the, or each, damper unit comprises connectors, such as 'plug-and-play' connectors, for connecting the at least one louvre actuator, and the one or more sensors if present, to the data centre control system. Preferably, the method comprises connecting the louvre actuator, and the one or more sensors if present, to a data centre services module.

Preferably, the air handling module is arranged for 'free air cooling' meaning that the air handling module makes use of cool ambient air from outside of the data centre to meet some or all of the cooling requirements of the IT equipment in the data centre. The air handling module may, for example, be arranged for direct free air cooling (also referred to herein as direct air cooling) or indirect free air cooling (also referred to herein as indirect air cooling).

Optionally, the air handling module is arranged for direct air cooling. As used herein, the term "direct air cooling" means using, optionally conditioned, external air from outside the building to directly cool the items of electronic equipment in the racks. Optionally, the air handling module is arranged for indirect air cooling. As used herein, the term "indirect air cooling" means using a device such as a heat exchanger to transfer heat from warm recirculated air that has been used to cool the items of IT equipment in the racks to external air from outside the data centre building wherein the recirculated air, once its heat has been absorbed by the external air, is used to cool the items of IT equipment in the racks. Preferably, when using indirect air cooling, the external air from outside the data centre building is kept separate from the internal air inside the data centre building. It will be appreciated that there may be occasions when some or all of the internal air inside the data centre building is refreshed with new air, that may originate from outside the data centre building, but that nevertheless the internal air inside the data centre used for indirect air cooling is considered as being kept separate from the external air from outside the data centre building. When the air handling module is arranged for indirect air cooling, the air handling module preferably comprises an external air outlet arranged to allow external air that has been used to absorb heat from the internal air to exit the air handling module. Preferably, the method comprises connecting the external air outlet of the air handling module to an air outlet aperture of the building. Optionally, the method comprises connecting the air handling module to an air outlet aperture of the building, wherein the air handling module comprises an integral damper unit for controlling the flow of air out of the building. Optionally, the method comprises connecting one or more damper units for controlling the flow of air out of the building to an air outlet aperture of the building, and arranging the air handling module such that the air outlet receives warm external air flowing out of the air handling module.

It will be appreciated that the apertures provided in the building for forming the air inlet and/or the air outlet may not be in fluid communication with the cold aisles and/or the hot aisles in the data centre, for example when the air handling unit is arranged for indirect air cooling.

Optionally, the step of forming the air inlet and the air outlet may be performed after the building meeting other pre-specified criteria has been provided. For example, it may be that the method comprises converting a pre-existing building into a data centre, wherein the method additionally comprises modifying the pre-existing building to provide the air inlet and the air outlet.

Preferably, the building is arranged such that cooling air and/or recirculated warm air flows along a path inside the building that is bounded by (defined in part by) an external wall of the building. Optionally, the method comprises providing an external wall to at least partially define an air flow path inside the building. Preferably, the pre-specified criteria include specifying that the external wall so used is sufficiently insulated to prevent condensation of water from the humid air on a surface in the air flow path, for example when the temperature outside the data centre is lower than the temperature inside the data centre.

Preferably, the method additionally comprises fabricating at least one of the prefabricated data centre elements at one or more sites remote from the building. Preferably, the method comprises arranging the prefabricated data centre elements in a transport configuration in which the elements occupy a first sum volume, transporting the prefabricated data centre elements so arranged, for example from the one or more remote sites to the building, and installing the prefabricated data centre elements in the building, wherein when the elements are installed in the building, they collectively define a second sum volume that is larger than the first sum volume. It will be appreciated that the prefabricated data centre elements may not necessarily be transported together in a single consignment. For example, the prefabricated data centre elements may be transported in a plurality of discrete packages, each package containing one or more of the prefabricated data centre elements. It will appreciated that the first sum volume occupied by the prefabricated data centre elements in the transport configuration is the total volume of the packages containing one or more elements, and that that second sum volume occupied by the prefabricated data centre elements when installed in the building is the single volume that encompasses all of those prefabricated data centre elements in their installed positions. For example, it may be that the second sum volume is the volume of the space in the building above the floor that is occupied by the prefabricated data centre elements in their installed positions. It will be appreciated that much of the space occupied by the prefabricated data centre elements in their installed positions may be 'empty space' in the form of hot and cold aisles and air supply and exhaust corridors. It will be appreciated that the second sum volume includes the air entrainment space, that is, the second sum volume includes the volumes of the hot and cold aisles and the air supply and exhaust corridors (when present).

Preferably, the method comprises providing a secondary supporting frame, such as a stillage, for supporting one or more of the prefabricated data centre elements during transportation and/or installation. It may be that providing a secondary supporting frame allows the prefabricated data centre element to be handled and manipulated without the element itself coming into direct contact with the handling and manipulating means. Preferably, the frame both supports and protects the element during transportation and/or installation. Preferably, the supporting frame is provided with wheels (e.g. trolley wheels), optionally detachable wheels, to allow the frame and its prefabricated data centre element to be conveniently manoeuvred. It will be appreciated that providing a supporting frame with wheels may allow the elements to be moved around inside the building without using heavy machinery such as forklift trucks. Optionally, the supporting frame is provided as a supporting frame assembly according to the seventh aspect of the invention. Preferably, the method comprises supporting each of the cold aisle services modules on a secondary support frame during transportation and/or during installation in the building. Preferably, the method comprises supporting a data centre services module (such as a services distribution module) on a secondary support frame during its transportation and/or during its installation in the building. Preferably, the method comprises supporting a vented door assembly on a secondary support frame during transportation and/or installation in the building. Preferably, the method comprises supporting a damper assembly on a secondary support frame during transportation and/or installation in the building.

Preferably, the method comprises using at least one of the secondary supporting frames as a jig to aid construction of one or more of the prefabricated data centre elements. For example, the method may comprise using a secondary supporting frame as a jig during fabrication of a prefabricated data centre element selected from the list consisting of: a data centre services module (such as a cold aisle services module or a services distribution module), a vented door assembly and a damper assembly; especially the list consisting of: a vented door assembly and a damper assembly; and optionally then using that same secondary supporting structure to support the prefabricated data centre element during transportation and/or installation. Preferably, the method comprises supporting a prefabricated data centre element (e.g. a vented door assembly or a damper assembly) on a secondary supporting structure and rotating the secondary support structure and thus also the prefabricated data centre element from a first, transport orientation to a second, deployed orientation. It may be that rotating the prefabricated data centre element allows it to be packaged more economically for transport, and that supporting the element on a secondary support frame as it is rotated reduces the risk of damage to the element. Preferably, the secondary support frame is provided with engaging elements for engagement with a lifting device, such as a forklift truck, for example. It may be that rotating a prefabricated data centre element allows an element having a height that is too large to fit into a conventional shipping container (e.g. an element that is taller than a conventional shipping container) to be placed on its side or on its face such that it can be conveniently inserted into such a conventional shipping container. Preferably, one or more of the secondary support frames are re-usable secondary support frames. There may be a step of retrieving and retaining a secondary support frame, which has been used in the transportation and/or installation of one of the prefabricated data centre elements, for re-use in subsequently transporting and/or installing a different prefabricated data centre element. There may be a step of so reusing the secondary support frame. Preferably, at least one supporting frame is configured to support a plurality of prefabricated data centre elements at once. It may be that supporting a plurality of elements on the same supporting frame provides a particularly efficient way of transporting the elements. Preferably, the method comprises supporting a plurality of data centre services modules (such as cold aisle services modules) on a single supporting frame. Preferably, the method comprises supporting a plurality of damper assemblies on a single supporting frame. Optionally, the supporting frame is provided as a supporting frame assembly according to the seventh aspect of the invention.

According to a second aspect, the invention provides a method of building a data centre using a data centre building envelope suitable for accommodating a plurality of IT equipment racks and subsequent steps which, when IT equipment racks are installed in the envelope, cause an aisle to be defined. The method may comprise an initial step of providing such a data centre building envelope. It may be that the building in which the envelope is provided is a building that pre-exists before the method of the present invention is performed. The step of providing the data centre building envelope may thus consist of establishing that a particular building or space in a building is suitable for use in the method. The data centre building envelope provided comprises a floor, a ceiling and at least one wall. The at least one wall and/or the ceiling have one or more air supply openings for admitting cooling air into the envelope. The data centre building envelope is provided with an electrical power source. The data centre building envelope provided is preferably configured to accommodate on the floor a plurality of IT equipment racks arranged in a plurality of rows separated by alternating hot and cold aisles. The data centre building envelope preferably defines at least part of a cold area in the data centre and/or at least part of a hot area in the data centre. Preferably, the data centre envelope excluding the one or more outside air openings is sufficiently insulated to prevent condensation of water in the cold area and/or the hot area of the data centre during normal operation of the data centre, for example as described with reference to the first aspect of the invention. It will be appreciated that 'normal operation' of the data centre means when the data centre is operating as designed (e.g. having not suffered any significant damage or malfunction), the temperature and humidity of the air inside the data centre is within design limits, and the temperature of the air outside the data centre is not lower than the typical average temperature of the coldest month of the year in the location of the data centre, preferably not lower than 10° C. below the typical average temperature of the coldest month of the year in the location of the data centre. The data centre building envelope excluding the one or more outside air openings preferably has a sufficient air tightness to provide a fan power degradation of no more than 5%, for example as described with reference to the first aspect of the invention. The subsequent steps preferably include connecting to the one or more air supply openings at least one air handling unit for supplying cooling air to the IT equipment racks when the IT equipment racks are installed in the envelope.

The subsequent steps preferably include connecting the at least one air handling unit to the electrical power source of the envelope.

The subsequent steps preferably include supporting on the underside of the ceiling a plurality of service-carrying frames, each service carrying frame comprising a plurality of air entrainment panels, the air entrainment panels being arranged to cooperate with two rows of IT equipment racks to entrain air in the aisle between the rows. Rows of IT equipment racks may thus be installed in the envelope so that an aisle having a length is defined and enclosed along its length by the floor, the two rows of IT equipment racks and the air entrainment panels of the service-carrying frame. Each service-carrying frame preferably additionally comprises at least one electrical supply bus for supplying electricity to the two rows of IT equipment racks, at least one cable tray, and optionally a lighting system for illuminating the aisle. It is preferred that the plurality of air entrainment panels, the at least one electrical supply bus, the at least one cable tray and the lighting system (if present) of each service-carrying frame is fitted to the service carrying frame before it is supported on the underside of the ceiling. The electrical supply bus may be in the form of a cable or bus-bar.

As used herein, the term "ceiling" is a notional term used to describe an internal part of the structure of the building envelope. For example, the "ceiling" may be in the form of the underside of the floor of an upper level of the building, or a roof. Alternatively, the ceiling may be in the form of a framework, for example a framework having a plurality of openings.

It will be appreciated that the method of the second aspect of the invention may include any feature disclosed in relation to the first aspect of the invention and vice versa. The service-carrying frame of the second aspect of the invention may incorporate any of the features of the cold aisle services module of the first aspect of the invention and vice versa.

Optionally, the data centre building envelope is a pre-existing building. It will be appreciated that the data centre building envelope may be any structure that is suitable for housing a data centre. For example, the data centre building envelope may be a basement of a building, or a natural or man-made cavern.

Preferably, when IT equipment racks are installed in the envelope, an aisle having a length is defined and/or enclosed along at least 80% of its length (for example substantially all, or all, of its length) by the floor, the two rows of IT equipment racks and the air entrainment panels of the service-carrying frame. Preferably, the upper part of the aisle, that is the part of the aisle above the racks, is defined and/or enclosed only by the service-carrying frame and its air entrainment panels.

Preferably, the method additionally comprises the steps of: supporting on the underside of the ceiling at least one services distribution frame comprising at least one cable tray and at least one electrical distribution bus for distributing electricity to one or more service carrying frames; and optionally connecting the electrical distribution bus of each services distribution frame to the electrical power source of the envelope and to the electrical supply bus of at least one of the service-carrying frames; wherein the electrical distribution bus and the at least one cable tray of each services distribution frame is fitted to the services distribution frame before it is supported on the underside of the ceiling. The services distribution frame of the second aspect of the invention may incorporate any of the features of the services distribution module of the first aspect of the invention, and vice versa.

Preferably, the at least one air handling unit is positioned in the interior of the envelope. Optionally, the air handling unit is a part of an air handling system having one or more other parts positioned separately to the air handling unit. For example, it may be that the air handling system comprises one or more mechanical cooling devices located outside of the envelope in addition to the air handling unit located inside the envelope. It may be that the air handling system comprises one or more such mechanical cooling devices for supplying cooling fluid to the air handling unit located inside the envelope. Preferably, the at least one air handling unit is connected to the inside of the one or more air supply openings. Preferably, the at least one air handling unit comprises an adiabatic cooling system.

Preferably, each aisle defined by the air entrainment panels of the service-carrying frame, the floor of the envelope and the two rows of IT equipment racks, when the IT equipment racks are installed in the building, is a cold aisle. It may be that there are rows of IT equipment racks, which define enclosed cold aisles interleaved with hot aisles which are open and in direct fluid communication with the space vertically above the air entrainment panels of the adjacent service-carrying frame(s). The hot aisles may be in direct fluid communication with the roof-space above the IT equipment racks, whereas the cold aisles are separated from the roof-space by means of the air entrainment panels.

Preferably, the method comprises supporting on the floor of the envelope one or more personnel doorway assemblies, each personnel doorway assembly comprising a door frame and a personnel door, the assembly comprising a vent for allowing cooling air to pass through the assembly, wherein each personnel doorway assembly is located at a position that will be at one end of a cold aisle when the rows of IT equipment racks are installed in the envelope. The personnel doorway assembly of the second aspect of the invention may incorporate any feature of the vented door assembly of the first aspect of the invention, and vice versa. Preferably, the vent is provided in the personnel door. Preferably, the vent is a controllable vent for regulating the flow of air into the cold aisle.

Preferably, the method additionally comprises installing a plurality of IT racks in a plurality of rows separated by alternating hot and cold aisles.

According to a third aspect, the invention provides a data centre comprising a building having a floor, walls and a roof, at least some of which define a load-bearing structure from which are suspended at least two cold aisle services modules. Each cold aisle services module is located above and spaced apart from the floor and has a length and a width. Each cold aisle services module has one or more integrated blanking portions including at least one ceiling member. Each cold aisle services module includes one or more data centre services extending along the length of the cold aisle services module, preferably terminating in a connector that is connected to a corresponding connector of an adjacent data centre services module. There may be multiple rows of IT racks arranged in parallel rows. There may be multiple cold aisles, for example defined between pairs of adjacent rows of IT racks. Preferably, the floor, the IT racks, and the cold aisle services modules including the associated integrated blanking portions together define the cold aisles.

It will be appreciated that the building of the data centre, having a floor, walls and a roof, can be constructed from any suitable material. For example, it may be that the building primarily comprises metal (such as steel), concrete, and/or wood. Additionally or alternatively, it may be that the building comprises a metal (such as steel), concrete, and/or wood frame. All that is required is that the building is suitable for housing data centre components, and that the building has a load-bearing structure that is suitable for suspending the cold aisle services modules. It will be appreciated that the building can be constructed from any suitable material, such as any preferred, locally available material. Using a preferred, locally available material for construction of the building may allow for more efficient construction, for example because local building contractors are familiar with the material. Furthermore, it may be that using different materials for construction in different locations makes it more straightforward to meet local building regulations.

Preferably, the data centre has a floor space of at least 20,000 $ft^2$, such as at least 40,000 $ft^2$. It will be appreciated that the floor space of the data centre is the total footprint of the space occupied by the various elements of the data centre including, for example, the air handling unit(s), the air supply corridor(s) and the hot and cold aisles.

Preferably, the data centre services module is suspended from the load-bearing structure of the building. Preferably, the data centre services module is located above and spaced apart from the floor.

It may be that the cold aisle services module is separated from the adjacent data centre services module by a partition, wherein the partition comprises an opening through which a connector of the cold aisle services module and/or a connector of the adjacent data centre services module passes.

Preferably, the cold aisle services module is arranged to additionally carry data centre hot aisle services, for example on an integrated hot aisle service portion. Thus, the cold aisle services module advantageously functions as both a cold aisle services module and a hot aisle services module. Optionally, the cold aisle services module comprises at least one data centre hot aisle service selected from the list consisting of: data carrying/network cables, electrical cables, earth cables and components of a hot aisle lighting system. Preferably, the cold aisle services module comprises at least one integrated hot aisle services portion that extends across and above at least part of at least one hot aisle adjacent to the cold aisle. Preferably, the at least one integrated hot aisle services portion comprises a hot aisle cable tray. Preferably, the cold aisle services module comprises two or more integrated hot aisle services portions, wherein one integrated hot aisle services portion extends across and above at least part of an adjacent hot aisle on one side of the cold aisle, and another integrated hot aisle services portion extends across and above at least part of another adjacent hot aisle on the other side of the cold aisle. Preferably, at least one of the integrated blanking portions of the cold aisle services module comprises an aperture for accommodating any data centre services passing between the hot and cold aisles. Preferably, the integrated blanking portion additionally comprises a closure device (e.g. a gasket, a grommet or a brush) for closing off the aperture around the data centre service passing between the hot and cold aisles through the aperture.

Optionally, the cold aisle services module has a length that corresponds to a multiple of the width of a conventional IT equipment rack (i.e. an integer multiple). It will be appreciated that having a module length that corresponds to a multiple of the width of a conventional IT equipment rack allows the straightforward construction of cold aisles with varying lengths from standardised parts. Preferably, the cold aisle services module has a length that corresponds to a multiple of the width of a standard IT equipment rack, such as an IT equipment rack having a width of 600 mm, for example corresponding to the width of any one of from 2 to 5 racks. It will be appreciated that the IT equipment may be provided in cabinets, such as cabinets having a width of 800 mm. The terms "IT equipment rack" and "IT equipment cabinet" are used interchangeably herein. Optionally, the cold aisle services module has a length of from 2 to 6 metres, such as about 2.4 metres. Preferably, the cold aisle services module has a width of from 1.5 to 6 metres, for example a width of from 3 to 6 metres. Preferably, the cold aisle services module has a height of from 0.3 metres to 1 metre, such as a height of about 0.5 metres. Preferably, the cold aisle services modules each comprise at least one attachment device, such as a clamp (e.g. a hasp clamp) for attaching the cold aisle services module to the adjacent data centre services module. Preferably, the cold aisle services modules each comprise at least one sealing devise, such as a gasket (e.g. a rubber gasket) for providing a substantially air-tight seal between the integrated blanking portions of the cold aisle services module and the adjacent data centre services module. Optionally, the adjacent data centre services module is a cold aisle services module. Preferably, at least one of the cold aisle services modules terminates in a first connection portion at one end of the module and a second connection portion at the other end of the module. Preferably, the first connection portion is connected to a corresponding connection portion of a first adjacent data centre services unit and the second connection portion is connected to a corresponding connection portion of a second adjacent data services module. Optionally, the first and/or the second data centre services module is a cold aisle services module. Preferably, at least one of the cold aisle services modules is connected to two other data centre services modules, for example two other cold aisle services modules. Preferably, at least one of the connection portions of the cold aisle services module comprises a clamping device for attaching the cold aisle services module to the adjacent data centre services module and/or a gasket (e.g. a rubber gasket) for providing a seal between the cold aisle services module and the adjacent data centre services module. Preferably, at least one of the connection portions of the cold aisle services module comprises a locating device for aligning the cold aisle services module with the adjacent data centre services module. Preferably, the adjacent data centre services module comprises a complementary locating device for engaging with the locating device of the connection portion of the cold aisle services module. Optionally, the locating devices of the connection portion of the cold aisle services module and the adjacent data centre services module are in the form of a projection and a recess, for example a cone-shaped projection and an inverted cone-shaped recess. It may be that having locating devices on the cold aisle services module and the adjacent data centre services module facilitates rapid and reliable alignment of the modules during installation in the data centre building.

Preferably, the one or more data centre services extending along the length of the cold aisle services modules includes at least one service selected from the list consisting of: electrical power services, data-carrying services, lighting services and fire suppression services. Preferably, each cold aisle services module comprises at least one item of data centre service-providing equipment selected from the list consisting of: cable trays, electrical cables, earth cables, data carrying/network cables, fire suppression system conduits (for example, fire suppression system conduits for carrying a fire suppressant fluid, such as water or a fire suppressant gas, such as an inert gas or mixtures of inert gases e.g. nitrogen and/or argon), sensor cables (for example fire detection sensor cables, temperature sensor cables and/or humidity sensor cables), sensors (for example fire detection sensors, temperature sensors and/or humidity sensors), lighting system cables, lighting systems (for example comprising one or more lights and/or one or more sensors for detecting the presence of a person in the aisle).

Optionally, the adjacent data centre services module is a services distribution module located above and spaced apart from the floor, wherein the services distribution module is suspended from the load-bearing structure of the building. Preferably, the services distribution module comprises a connector that is connected to a corresponding connector on at least one adjacent cold aisle services module. Additionally or alternatively, the services distribution module comprises a connector that is connected to a corresponding connector on at least one adjacent second services distribution module. Preferably, the services distribution module comprises one or more services selected from the list consisting of: electrical power services, data-carrying services and fire suppression services. Preferably, the services distribution module comprises at least one item of data centre service-providing equipment selected from the list consisting of: electrical cables, earth cables, network cables, fire suppression system conduits (for example, fire suppression system conduits for carrying a fire suppressant fluid, such as water, or a fire suppressant gas, such as an inert gas or mixtures of inert gases e.g. nitrogen and/or argon), sensor cables (for example fire detection sensor cables, temperature sensor cables and/or humidity sensor cables), sensors (for example fire detection sensors, temperature sensors and/or humidity sensors), lighting system cables, lighting systems (for example comprising one or more lights and/or one or more sensors for detecting the presence of a person in the corridor).

Preferably, one or more, such as all, of the services distribution modules comprise data centre services connected to data centre services on one or more adjacent cold aisle services modules and data centre services connected to data centre services on one or more adjacent services distribution modules.

Preferably, the services distribution module has a length of from 2 to 8 metres, such as from 4 to 5 metres. Preferably, the services distribution module has a width of from 1 to 3 metres, such as from 1 to 2 metres. Preferably, the services distribution module has a height of from 0.3 metres to 1 metre, such as about 0.5 metres.

Preferably, the data centre comprises an air handling unit for supplying cooling air to the IT racks via the cold aisles. Preferably, the air handling unit comprises a plurality of fans for effecting transport of the cooling air from the air handling unit to the IT racks. Preferably, the data centre is arranged such that the cooling air is transported from the air handling unit to the IT racks entirely above the floor of the building. Preferably, the data centre is arranged such that the cooling air flows along a cooling air path extending from the air handling unit to the IT racks, wherein the cooling air path is located above the floor for its entire length. Preferably, the data centre comprises an air supply corridor for transporting cooling air above the floor from the air handling unit to the cold aisles. Preferably, the air supply corridor has a height of at least 1.5 m, such as at least 2.5 m, above the floor. Preferably, the air supply corridor is a personnel corridor providing personnel access to the IT racks via the cold aisles. Preferably, the air handling unit comprises an adiabatic cooling unit for adiabatically cooling external air entering the building. Preferably, the adiabatic cooling unit comprises a wetted matrix adiabatic cooler. As used herein, the term "wetted matrix adiabatic cooler" refers to an apparatus comprising a wettable air-permeable medium supplied with a controllable amount of fluid, such as water, and arranged such that external air entering the building can bed passed through the wetted air-permeable medium and cooled by evaporation of the fluid into the external air stream.

Preferably, the, or each, services distribution module is located in the air supply corridor.

Preferably, the building comprises a plurality of templated fixing locations for fixing the cold aisle service units and the data centre services module to the load-bearing structure.

Preferably, the cold aisle services modules and the data centre services module are supported directly and entirely by the load bearing structure of the building. It will be appreciated that "supported directly and entirely by the load bearing structure of the building" means that the cold aisle services modules and the data centre services module are not supported by the IT racks, for example. Preferably the services distribution modules are supported directly and entirely by the load bearing structure of the building. Preferably, the vented door assembly, the damper assembly and/or the air handling unit is supported directly and entirely by the load bearing structure of the building.

According to a fourth aspect, the invention provides a data centre comprising a data centre building envelope, at least one air handling unit, and a plurality of service-carrying frames supported on the underside of a ceiling in the building envelope, each service carrying frame comprising a plurality of air entrainment panels, which are arranged to entrain air, from the air handling unit, in an aisle defined between two rows of IT equipment racks. The envelope comprises a floor, a ceiling and at least one wall. The at least one wall and/or the ceiling have one or more air supply openings for admitting cooling air into the envelope. The data centre building envelope excluding the one or more outside air openings is preferably sufficiently insulated to prevent condensation of water on surfaces in the cold areas and/or hot areas of the data centre, for example as described with reference to the first aspect of the invention. The data centre building envelope excluding the one or more outside air openings preferably has a sufficient air tightness to provide a fan power degradation of no more than 5%, for example as described with reference to the first aspect of the invention. The envelope is preferably configured for accommodating on the floor a plurality of IT equipment racks arranged in a plurality of rows separated by alternating hot and cold aisles. The envelope is provided with an electrical power source. The at least one air handling unit for supplying cooling air to the IT equipment racks when the IT equipment racks are installed in the envelope, is connected to the one or more air supply openings and is also connected to the electrical power source of the envelope. The data centre is preferably so arranged that, when IT equipment racks are installed in the envelope, the air entrainment panels of the service carrying frames cooperate with two rows of IT equipment racks to define an aisle between the rows, the aisle being enclosed along its length by the floor, the two rows of IT equipment racks and the air entrainment panels of the service carrying frame. Alternatively, the data centre is preferably so arranged that, when IT equipment racks are installed in the envelope, the air entrainment panels of a first set of service carrying frames cooperate with a first row of IT equipment racks, and the air entrainment panels of a second set of service carrying frames cooperate with a second row of IT equipment racks, the air entrainment panels on the first and second sets of service carrying frames, the two rows of IT equipment racks and a floor of the envelope together defining and enclosing along its length an aisle between the two rows of IT equipment racks.

Each service carrying frame preferably additionally comprises at least one electrical supply bus for supplying electricity to the two rows of IT equipment racks, at least one cable tray, and optionally a lighting system for illuminating the aisle.

It will be appreciated that the data centre of the fourth aspect of the invention may include any feature disclosed in relation to the third aspect of the invention and vice versa. The service-carrying frame of the fourth aspect of the invention may incorporate any of the features of the cold aisle services module of the third aspect of the invention, and vice versa.

Preferably, the data centre comprises at least one services distribution frame supported on the underside of the ceiling, each services distribution frame comprising at least one cable tray and at least one electrical distribution bus for distributing electricity to one or more service carrying frames. The services distribution frame of the fourth aspect of the invention may incorporate any of the features of the services distribution module of the third aspect of the invention, and vice versa.

Preferably, the data centre comprises an air supply corridor for transporting cooling air from the air handling unit to cold aisles and thus to the IT equipment racks, the air supply corridor also providing personnel access to the cold aisles and thus to the IT equipment racks. Preferably, the at least one services distribution frame is located in the air supply corridor.

Preferably, the data centre comprises a personnel doorway assembly located at one end of at least one of, optionally all of, the cold aisles, the personnel doorway assembly providing personnel access to the cold aisle from the air supply corridor, wherein the assembly comprises a frame, a door and a vent for allowing cooling air to flow into the cold aisle from the air supply corridor. Preferably the vent is a controllable vent for regulating the flow of cooling air into the cold aisle from the air supply corridor. Preferably the vent is provided in the door.

Preferably the data centre comprises a plurality of racks of items IT equipment arranged in a plurality of rows separated by alternating hot and cold aisles.

According to a fifth aspect, the invention provides a service-carrying frame for suspending from a ceiling of a building above a floor, the service-carrying frame comprising a plurality of air entrainment panels, the air entrainment panels being arranged to cooperate with at least one row of IT equipment racks mounted on the floor in order to entrain air in a space between the row of IT equipment racks and an adjacent spaced apart parallel row of IT equipment racks and above the floor, wherein each service-carrying frame additionally comprises at least one electrical supply bus for supplying electricity to the two rows of IT equipment racks, at least one cable tray, and a lighting system for illuminating the space between the rows of IT equipment racks. Preferably, the air entrainment panels of the service-carrying frame are arranged to cooperate with two rows of IT equipment racks mounted on the floor in order to entrain air in the space between the rows and above the floor. The service-carrying frame of the fifth aspect of the invention may incorporate any feature of the cold aisle services module of the third aspect of the invention or the service-carrying frame of the fourth aspect of the invention, and vice versa.

According to a sixth aspect, the invention provides a cold aisle services module for suspending from a load bearing structure of a building above and spaced apart from a floor of a building, the cold aisle services module having a length and a width, one or more integrated blanking portions including at least one ceiling member, and one or more data centre services extending along the length of the cold aisle services module and terminating in a connector suitable for connection to a corresponding connector of a separate data centre services module.

According to a seventh aspect, the invention provides a supporting frame assembly configured to support one or more of (and preferably a plurality of) prefabricated data centre elements at once. It may be that supporting a plurality of elements on the same supporting frame provides a particularly efficient way of transporting the elements. Preferably, the supporting frame comprises a plurality of wheels (e.g. trolley wheels), optionally detachable wheels, to allow the frame and its prefabricated data centre element to be conveniently manoeuvred. It will be appreciated that providing a supporting frame with wheels may allow the elements to be moved around inside the building without using heavy machinery such as forklift trucks. Optionally, the supporting frame comprises a brake for preventing unwanted movement of the supporting frame. The brake may, for example, be in the form of a jacking device configured to lift at least one wheel of the supporting frame off the floor, and/or in the form of a friction pad configured to engage with the wheel to prevent its rotation and/or the floor to prevent movement of the frame across the floor. Optionally, the supporting frame is provided with guide wheels on at least two opposing sides to allow the frame to be conveniently manoeuvred along a wall. Optionally, the supporting frame is sized and configured to fit inside a standard sized ISO shipping container, for example the supporting frame is sized and configured to have a length or a width (including the guide wheels, if present) substantially equal to the internal width of a standard size ISO shipping container (for example having an internal width of about 2.0 to about 2.6 m, such as about 2.1 to about 2.3 m, e.g. about 2.2 m). It will be appreciated that when the supporting frame comprises guide wheels on at least two opposing sides, it may be particularly easy to manoeuvre the supporting frame into such a shipping container. A single shipping container may contain two or more, three or more and possibly at least four supporting frames with their associated prefabricated data centre elements supported thereon, the supporting frames being arranged end-to-end along the length of the container. Preferably, the supporting frame assembly comprises a supporting frame and a plurality of detachable support posts for connecting prefabricated data centre elements to the supporting frame. Optionally, when a supporting frame assembly is configured to support a plurality of prefabricated data centre elements, the posts are configured to transmit the weight of each prefabricated data centre element to the frame independently of all of the other prefabricated data centre elements. In other words, the lower prefabricated data centre element(s) preferably does not support the weight of any of the other prefabricated data centre elements. Optionally, a set of support posts is provided for each prefabricated data centre element, wherein each support post is configured to engage with either the supporting frame or another support post, e.g. to transfer the weight of each prefabricated data centre element to the supporting frame directly or only via one or more other support posts. Alternatively, or additionally, a set of support posts may be provided so as to support, and preferably hold in position, each prefabricated data centre element in position one above the other in a stack of such prefabricated data centre elements. There may be three or more (preferably four or more) separate support posts between each pair of adjacent prefabricated data centre elements in the stack. Preferably, the supporting frame assembly is movable between a first, assembled, configuration in which the support posts are connected to the supporting frame (optionally via another support post) and to a prefabricated data centre element, and a second, return, configuration in which the support posts are connected to the supporting frame, wherein the volume of the supporting frame assembly in the second, return, configuration is smaller than the volume of the supporting frame assembly in the first, assembled configuration. For example, it may be that the supporting frame is provided with a plurality of connection points, wherein each connection point is configured to connect to a support post. It may be that such a configuration provides a particularly convenient way of keeping the parts of the supporting frame assembly together when returning it to the factory for re-use. There may be six or more, preferably twelve or more, support posts connected to the supporting frame when in the second, return, configuration.

According to an eighth aspect, the present invention provides a services distribution frame comprising at least one cable tray, at least one electrical distribution bus, and at least one electrical distribution bus connector for connecting each electrical distribution bus to a corresponding connector on a service carrying frame, wherein the electrical distribution bus connector comprises a flexible section allowing the electrical distribution bus connector to be movable from a transport configuration in which the distal end of the electrical distribution bus connector can be releasably secured adjacent to the body of the services distribution frame to a deployed configuration in which the electrical distribution bus connector can be secured to the corresponding connector on the service carrying frame. Optionally, the services distribution frame comprises a bracket for securing the distal end of the electrical distribution bus connector in the transport configuration. Preferably, the services distribution frame has rotational symmetry about a vertical axis, such as two-fold rotational symmetry. It will be appreciated that a vertical axis is an axis that is vertical when the services distribution frame is in its installed orientation (i.e. its orientation when installed in the building). It may be that having rotational symmetry allows the frame to be used in an air supply corridor at either end of the cold aisle.

According to a ninth aspect, the present invention provides a damper unit comprising: a frame, at least one set of adjustable louvres mounted on the frame; a shroud mounted on the frame around the at least one set of adjustable louvres, the shroud projecting outwards from the frame; at least one actuator connected to the at least on set of adjustable louvres and arranged to adjust the position of the louvres in order to control the flow of air through the damper unit; and, an electronic control unit for communicating with a data centre control system and controlling operation of the actuator; wherein, the electronic control system is positioned such that it does not extend beyond an outer edge of the outwardly projecting shroud. In other words, for example when the control unit is mounted on the frame (directly or indirectly), the control unit is positioned behind an edge of the shroud that extends away from the frame. It may be that such positioning of the control system shields the control system from the air (and thus from moisture in the air) flowing through the damper unit. Optionally, the damper unit comprises at least one sensor for measuring a characteristic of air flowing through the damper unit, such as one or more temperature and/or humidity sensor for measuring the temperature and/or humidity of air flowing through the damper unit, and/or one or more air sampling devices for monitoring air quality. Preferably, the damper unit comprises connectors, such as 'plug-and-play' connectors, for connecting the control system, and the one or more sensors, if present, to the data centre control system. Optionally, each set of adjustable louvres is provided with a detachable fly screen, for example mounted (directly or indirectly) to the frame with clip connectors, e.g. to allow the screen to be conveniently removed for maintenance. Optionally, the fly screen is mounted to the frame via an edge of the shroud.

Further aspects of the invention are described below in the following clauses:

Clause A. A method of building a data centre comprising: a first step of:

providing a data centre building envelope, the envelope comprising a floor, a ceiling and at least one wall, the at least one wall and/or the ceiling having one or more air supply openings for admitting cooling air into the envelope, wherein the envelope is suitable for accommodating on the floor a plurality of IT equipment racks arranged in a plurality of rows separated by alternating hot and cold aisles and wherein the envelope is provided with an electrical power source;

and subsequent steps of:

connecting to the one or more air supply openings at least one air handling unit for supplying cooling air to the IT equipment racks when the IT equipment racks are installed in the envelope;

connecting the at least one air handling unit to the electrical power source of the envelope;

supporting on the underside of the ceiling a plurality of service-carrying frames, each service carrying frame comprising a plurality of air entrainment panels, the air entrainment panels being arranged to cooperate with two rows of IT equipment racks to entrain air in the aisle between the rows, wherein when IT equipment racks are installed in the envelope an aisle having a length is defined and enclosed along its length by the floor, the two rows of IT equipment racks and the air entrainment panels of the service-carrying frame, and wherein each service-carrying frame additionally comprises at least one electrical supply bus for supplying electricity to the two rows of IT equipment racks, at least one cable tray, and a lighting system for illuminating the aisle;

wherein, the plurality of air entrainment panels, at least one electrical supply bus, at least one cable tray and the lighting system of each service-carrying frame is fitted to the service carrying frame before it is supported on the underside of the ceiling.

Clause B. A method according to Clause A, wherein the method additionally comprises the steps of:

supporting on the underside of the ceiling at least one services distribution frame comprising at least one cable tray and at least one electrical distribution bus for distributing electricity to one or more service carrying frames; and connecting the electrical distribution bus of each services distribution frame to the electrical power source of the envelope and to the electrical supply bus of at least one of the service-carrying frames;

wherein the electrical distribution bus and the at least one cable tray of each services distribution frame is fitted to the services distribution frame before it is supported on the underside of the ceiling.

Clause C. A method according to Clause A or Clause B, wherein the method additionally comprises installing a plurality of IT racks in a plurality of plurality of rows separated by alternating hot and cold aisles.

Clause D. A method according to any of Clauses A to C, wherein the data centre building envelope defines at least part of a cold area in the data centre, and wherein the data centre building envelope excluding the one or more outside air openings is sufficiently insulated to prevent condensation of water in the cold area during normal operation of the data centre.

Clause E. A method according to any of Clauses A to D, wherein the data centre building envelope defines at least part of a cold area in the data centre, and wherein the data centre building envelope excluding the one or more outside air openings is sufficiently air tight to provide a fan power degradation of not more than 5%.

Clause F. A data centre comprising:

a data centre building envelope, the envelope comprising a floor, a ceiling and at least one wall, the at least one wall and/or the ceiling having one or more air supply openings for admitting cooling air into the envelope, wherein the envelope is suitable for accommodating on the floor a plurality of IT equipment racks arranged in a plurality of rows separated by alternating hot and cold aisles and wherein the envelope is provided with an electrical power source;

at least one air handling unit for supplying cooling air to the IT equipment racks when the IT equipment racks are installed in the envelope, the at least one air handling unit being connected to the one or more air supply opening, and the air handling unit being connected to the electrical power source of the envelope;

a plurality of service-carrying frames supported on the underside of the ceiling, each service carrying frame comprising a plurality of air entrainment panels, the air entrainment panels being arranged to cooperate with two rows of IT equipment racks to entrain air in the aisle between the rows, wherein when IT equipment racks are installed in the envelope an aisle is defined and enclosed along its length by the floor, the two rows of IT equipment racks and the air entrainment panels of the service carrying frame, and wherein each service carrying frame additionally comprises at least one electrical supply bus for supplying electricity to the two rows of IT equipment racks, at least one cable tray, and a lighting system for illuminating the aisle.

Clause G. A data centre according to Clause F, wherein the data centre comprises at least one services distribution frame supported on the underside of the ceiling, each services distribution frame comprising at least one cable tray and at least one electrical distribution bus for distributing electricity to one or more service carrying frames.

Clause H. A data centre according to Clause F or Clause G, wherein the data centre comprises an air supply corridor for transporting cooling air from the air handling unit to cold aisles and thus to the IT equipment racks, the air supply corridor also providing personnel access to the cold aisles and thus to the IT equipment racks, and wherein the at least one services distribution frame is located in the air supply corridor.

Clause I. A data centre according to Clause H, wherein the data centre comprises a personnel doorway assembly located at one end of at least one of the cold aisles, the personnel doorway assembly providing personnel access to the cold aisle from the air supply corridor, wherein the assembly comprises a frame, a door and a vent for allowing cooling air to flow into the cold aisle from the air supply corridor.

Clause J. A data centre according to any one of Clauses F to I, wherein the data centre comprises a plurality of racks of items IT equipment arranged in a plurality of rows separated by alternating hot and cold aisles.

Clause K. A data centre according to any one of Clauses F to J, wherein the data centre building envelope defines at least part of a cold area in the data centre, and wherein the data centre building envelope excluding the one or more air supply openings is sufficiently insulated to prevent condensation of water in the cold area during normal operation of the data centre.

Clause L. A method according to any one of Clauses F to K, wherein the data centre building envelope defines at least part of a cold area in the data centre, and wherein the data centre building envelope excluding the one or more air supply openings is sufficiently air tight to provide a fan power degradation of not more than 5%.

It will of course be appreciated that features described in relation to one aspect of the present invention may be incorporated into other aspects of the present invention. For example, any methods of the invention may incorporate any of the features described with reference to any apparatus of the invention, and vice versa.

DESCRIPTION OF THE DRAWINGS

Embodiments of the present invention will now be described by way of example only with reference to the accompanying schematic drawings of which:

FIG. 7 shows a rear perspective view of a warm air recirculation damper unit;

FIG. 8 shows a front perspective view of the warm air recirculation damper unit of FIG. 7;

DETAILED DESCRIPTION

The embodiments illustrated by the accompanying Figures together relate to a method of constructing a data centre. The method of construction divides out the technical requirements of the building that accommodates the various functional parts of the interior of the data centre, and the technical requirements of those internal functional data centre parts. The internal functional data centre parts are provided in the form of different prefabricated data centre elements. The number of different types of prefabricated data centre elements is relatively low, meaning that each prefabricated data centre element is a relatively technically complicated piece of kit. The technical requirements of the data centre building envelope may be dealt with locally on-site by a local work-force, having appropriate skills and expertise. The manufacture of the relatively complicated and technically demanding prefabricated data centre elements may be dealt with remotely (off-site) by a specialist work-force working in a dedicated facility. By separating out the technical requirements of the building envelope from the technical requirements of the (prefabricated) data centre elements it is possible to utilise remote manufacturing, to enable construction of a data centre using a relatively low-skilled workforce locally on-site, and to increase efficiency. Furthermore, by providing high levels of functionality in many of the (prefabricated) data centre elements, it is possible to reduce both the number of different elements required to fit out a data centre and also the packaged volume of those elements during transport. For example, cold aisle services modules may provide the triple functionality of accommodating cold aisle services, accommodating hot aisle services and providing entrainment of cold air in the cold aisles; vented door assemblies may provide the triple functionality of defining parts of a cold aisle and of an air supply corridor, regulating sir flow into a cold aisle and housing sensors for the data centre control system.

Figure 1:
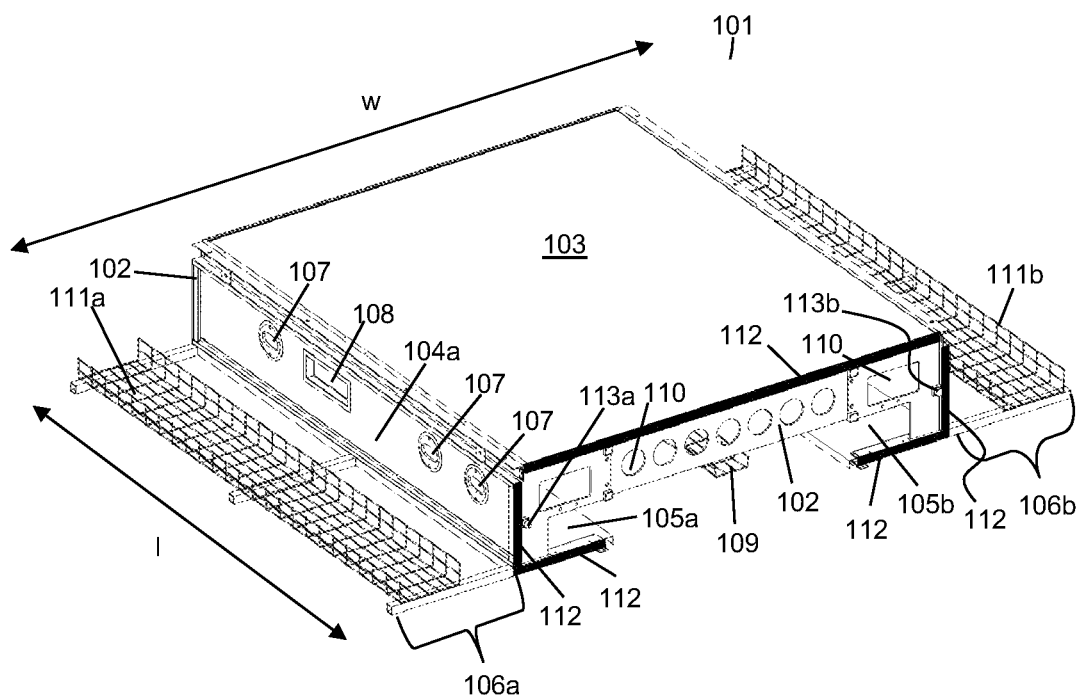
FIG. 1 shows a top perspective view of a cold aisle services module.

FIG. 1 shows a top perspective view of a cold aisle services module 101, which forms one of the prefabricated data centre elements of an embodiment of the invention. The cold aisle services module 101 has a length 1 and a width w. The cold aisle services module 101 comprises a steel frame 102 which supports a top integral blanking portion 103 that extends horizontally across the width of an upper part of the cold aisle services module 101, two side integral blanking portions 104a and 104b (104b is not shown in FIG. 1) that extend downwards at the sides of the top integral blanking portion 103, and lower integral blanking portions 105a and 105b that extend horizontally inwards from the bottom edges of the side integral blanking portions 104a and 104b, respectively. The cold aisle services module 101 is also provided with two integrated hot aisle services portions 106a and 106b extending horizontally outwards from the bottom edges of the side integral blanking portions 104a and 104b, respectively. The hot aisle services portions 106a and 106b are detachable from the frame 102 of the cold aisle services module 101. The integral side blanking portions 104a and 104b are provided with four apertures 107 and 108 to accommodate data centre services passing between the hot and cold aisles of the data centre (only the apertures of side integral blanking portion 104a are shown in FIG. 1). Apertures 107 comprise grommets for closing off the aperture around the data centre services passing through the apertures when installed. Aperture 108 is provided with a brush (not shown) to close off the aperture around the data centre services passing through the aperture when installed. Suspended from the frame 102 of the cold aisle services module 101 is a cable tray 109 for accommodating cold aisle services, such as cables (not shown). Openings 110 are provided in the frame 102 for accommodating further data centre services. Optionally, further data centre services (not shown in FIG. 1) can be installed above the lower integral blanking portions 105a and 105b. The hot aisle services portions 106a and 106b are provided with cable trays 111a and 111b for accommodating hot aisle services, such as cables (not shown). Each end of the cold aisle services module 101 is provided with a rubber gasket 112 that extends along the edge of the frame 102. The gasket 112 is provided in four pieces that extend along the edge of the frame 102 at the ends of the integral blanking portions 103, 104a, 104b, 105a and 105b. Location devices in the form of cone-shaped protrusions 113a and 113b are provided at one end of the cold aisle services module 101 on the frame 102. Location devices in the form of inverted cone-shaped protrusions (not shown in FIG. 1) are provided at the other end of the cold aisle services module 101. The cold aisle services module 101 is also provided with hasp clamps (not shown in FIG. 1) at one end for securing the cold aisle services module 101 to an adjacent cold aisle services module (not shown in FIG. 1).

Figure 2:
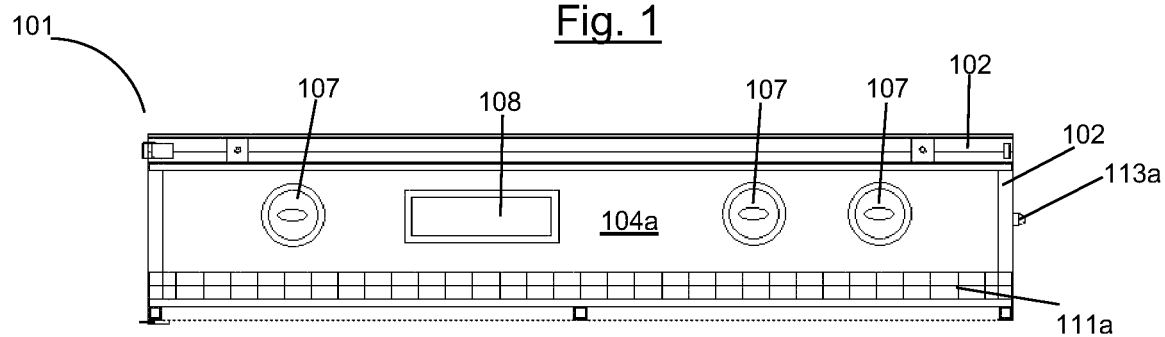
FIG. 2 shows a side elevation view of the cold aisle services module of FIG. 1.

FIG. 2 shows a side elevation view of the cold aisle services module 101 of FIG. 1. The parts of the cold aisle services module 101 visible in FIG. 2 are labelled with the same reference numerals used in FIG. 1. The gasket 112 is not shown in FIG. 2.

Figure 3:
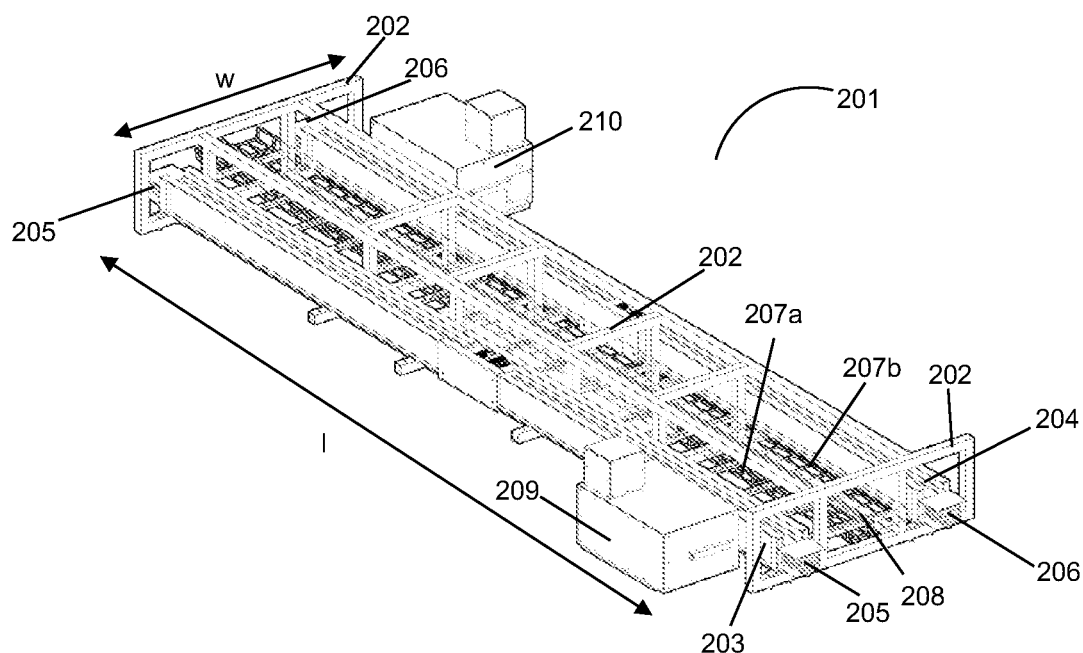
FIG. 3 shows a top perspective view of a services distribution module.

FIG. 3 shows a top perspective view of a services distribution module 201, which forms one of the prefabricated data centre elements of an embodiment of the invention and which is arranged in the data centre for carrying services outside the cold aisles (for example in the cold corridor—or cold zone—that supplies cooling air to the cold aisles in the completed data centre). The services distribution module 201 comprises a steel frame 202 and has a length 1 and a width w. Extending along the length of the services distribution module 201 are a main electrical power bus 203 and a backup electrical power bus 204. The ends of the main and backup electrical power buses 203 and 204 are provided with slot-fitting plug and play connectors 205 and 206, respectively. Even though the power buses 203 and 204 are provided with plug and play connectors, it may be that a qualified electrician makes or checks the connection, for example because of the relatively high power rating of the power buses 203 and 204. The connectors 205 and 206 engage with corresponding connectors on an adjacent services distribution module (not shown in FIG. 3). The services distribution module 201 is also provided with cable trays 207a and 207b for accommodating data centre services, such as cables, and with an earth rod 208. Connection housings 209 and 210 are provided for housing flexible connectors (not shown in FIG. 3) that are deployable to connect the main and backup electrical power buses to an adjacent cold aisle services module (not shown in FIG. 3).

Figure 4:
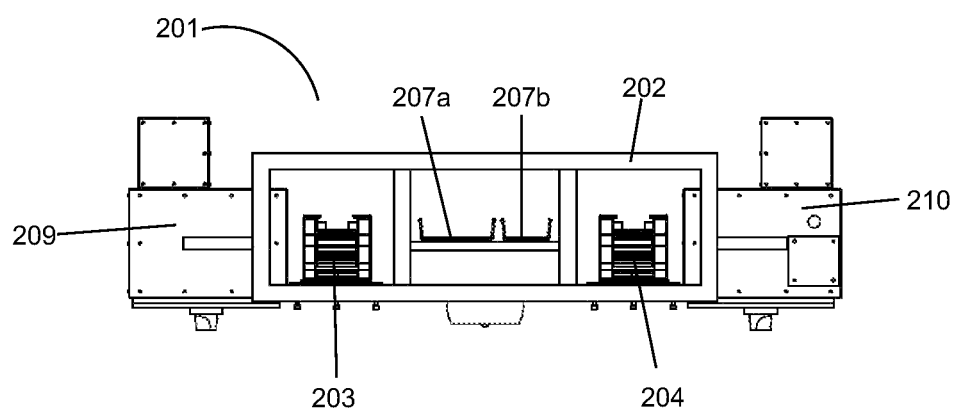
FIG. 4 shows an end elevation view of the services distribution module of FIG. 3.

FIG. 4 shows an end elevation view of the services distribution module 201 of FIG. 3. Those parts of the services distribution module 201 of FIG. 3 visible in FIG. 4 are labelled with the same reference numerals used in FIG. 3.

Figure 5:
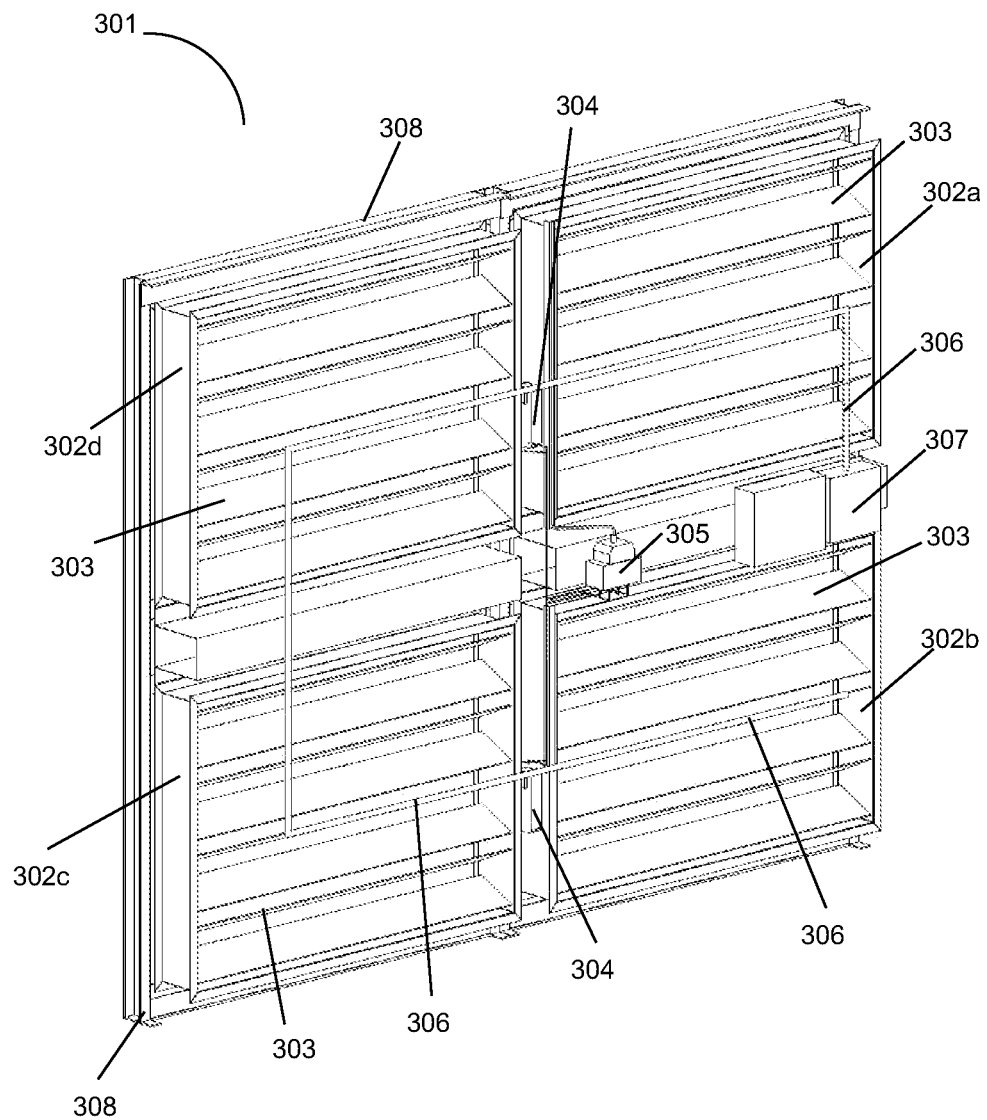
FIG. 5 shows a rear perspective view of an air intake damper unit.

FIG. 5 shows a rear perspective view of an air intake damper unit 301 (that is, the view of the air intake damper unit 301 as seen from inside the data centre when installed), which forms one of the prefabricated data centre elements of an embodiment of the invention. The air intake damper unit 301 comprises four controllable vents 302a to 302d each including multiple controllable louvres 303. The louvres 303 are continuously adjustable between fully closed and fully open positions, and are shown in a partially open position in FIG. 5. The louvres are adjusted by actuators 304 provided for each of the vents 302a to 302d (only the actuators 304 of vents 302a and 302b are shown in FIG. 5). The actuators 304 are controlled by a pre-wired vent control system 305 provided with plug-and-play connectors (not shown in FIG. 5) for connecting the vent control system to the main data centre control system. The air intake damper unit 301 is also provided with a pre-wired temperature and humidity sensor (not shown in FIG. 5) for measuring the temperature and humidity of air entering the data centre through the vents 302a to 302d. The sensor is provided with a plug-and-play connector (not shown in FIG. 5) ready for connection to the data centre control system. A smoke detection system comprising a sampling pipe 306 and a sensor unit 307 is provided on the air intake damper unit 301. The smoke detection system sensor unit 307 is pre-wired and provided with a plug-and-play connector (not shown in FIG. 5) for connection to the data centre control system. The air intake damper unit 301 also comprises a frame 308 that supports its various components. The air intake damper unit 301 could alternatively be used as an air exhaust damper unit.

Figure 6:
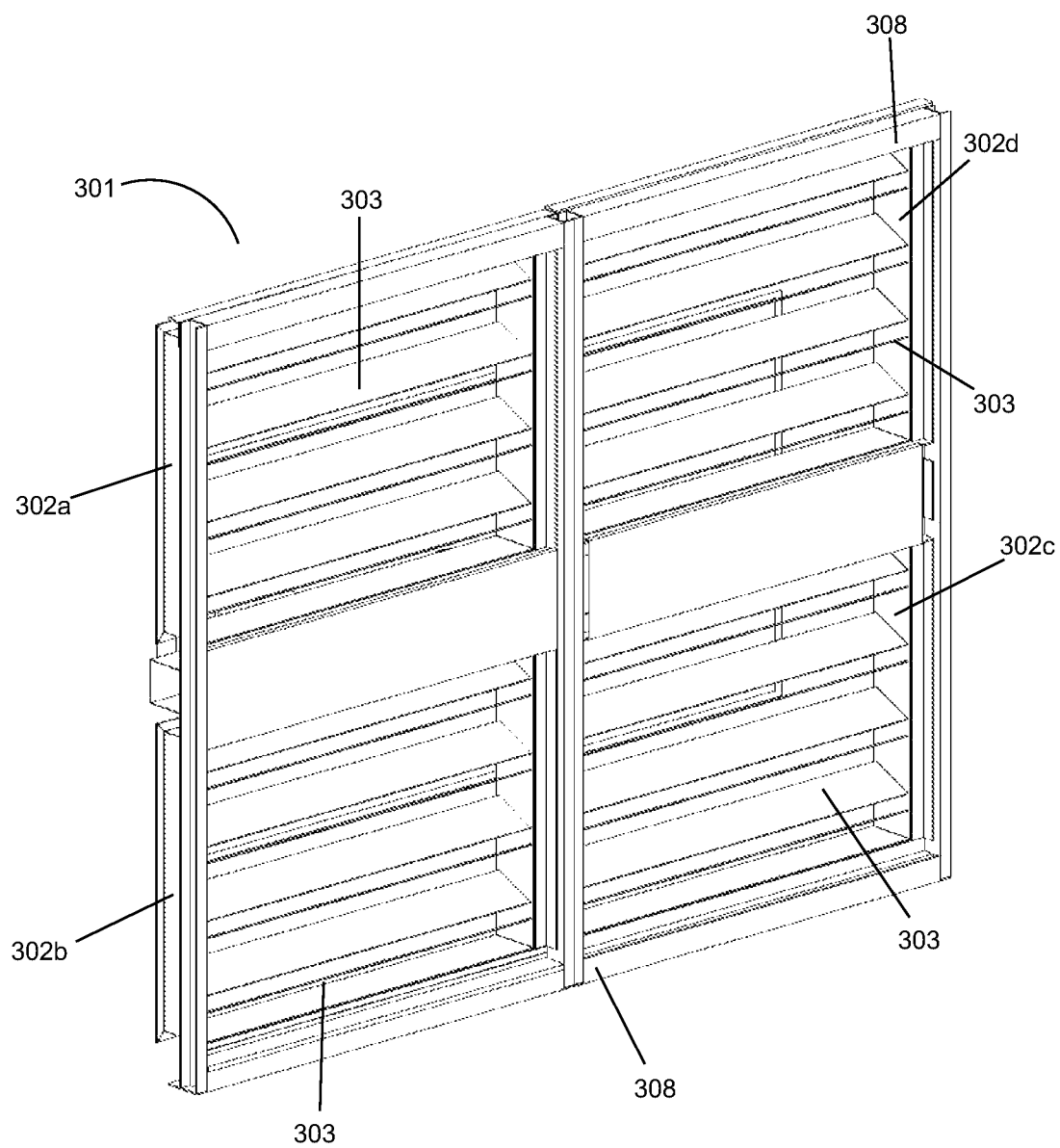
FIG. 6 shows a front perspective view of the air intake damper unit of FIG. 5.

FIG. 6 shows a front perspective view of the air intake damper unit 301 of FIG. 5 (that is, the view of the air intake damper unit 301 as seen from outside the data centre when installed). Those parts of the air intake damper unit 301 of FIG. 5 visible in FIG. 6 are labelled with the same reference numerals as used in FIG. 5.

FIG. 7 shows a rear perspective view of a warm air recirculation damper unit 401, which forms one of the prefabricated data centre elements of an embodiment of the invention. The warm air recirculation damper unit 401 comprises two controllable vents 402*a* and 402*b* each including multiple controllable louvres 403. The louvres 403 are continuously adjustable between fully closed and fully open positions, and are shown in a partially open position in FIG. 7. The louvres are adjusted by actuators 404 provided for each of the vents 402*a* and 402*b* (see FIG. 8). The actuators 404 are controlled by a pre-wired control system provided with plug-and-play connectors (not shown in FIG. 7) for connecting the control system to the main data centre control system. The warm air recirculation damper unit 401 is also provided with a pre-wired temperature and humidity sensors (sensors not shown in FIG. 7, by sensor mounting points 405 are shown) for measuring the temperature and humidity of warm air recirculating through the vents 402*a* and 402*b*. The sensors are provided with a plug-and-play connectors (not shown in FIG. 7) ready for connection to the data centre control system. A smoke detection system comprising a sampling pipe 406 and a sensor unit 407 is provided on the warm air recirculation damper unit 401. The smoke detection system sensor unit 407 is pre-wired and provided with a plug-and-play connector (not shown in FIG. 7) for connection to the data centre control system. The warm air recirculation damper unit 401 also comprises a frame 408 that supports its various components.

FIG. 8 shows a front perspective view of the warm air recirculation damper unit 401 of FIG. 7. Those parts of the warm air recirculation damper unit 401 of FIG. 7 visible in FIG. 8 are labelled with the same reference numerals as used in FIG. 7.

Figure 9:
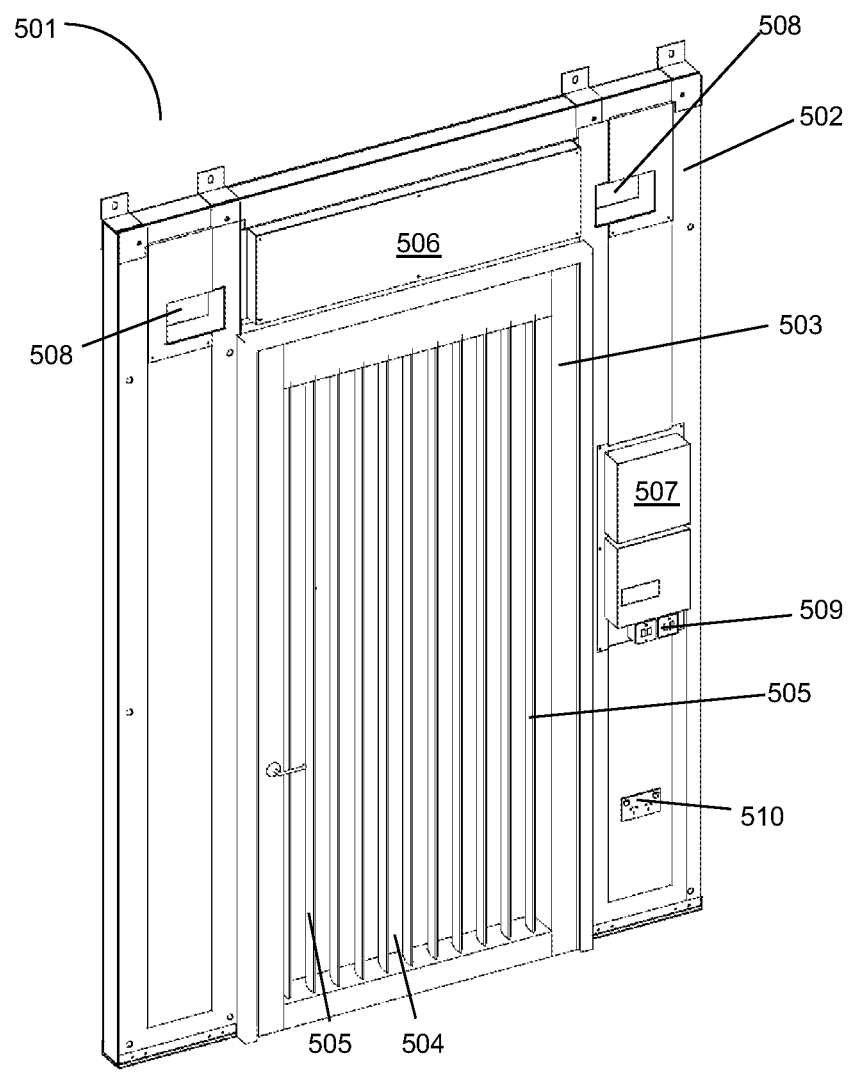
FIG. 9 shows a front perspective view of a vented door assembly.

FIG. 9 shows a front perspective view of a vented door assembly 501, which forms one of the prefabricated data centre elements of an embodiment of the invention. The vented door assembly 501 comprises a frame 502 and a door 503, the door 503 having a vent 504 comprising a plurality of adjustable louvres 505. The adjustable louvres 505 are controlled by an actuator system provided in housing 506. The vented door assembly 501 is pre-wired and ready for connection to the data centre control system, the vented door assembly 501 having sensors for measuring the temperature and humidity in the air supply corridor and/or the cold aisle, the sensors being connected to sensor system provided in housings 506 and 507. The actuator system and sensor system are provided with plug-and-play connectors to allow fast and straightforward connection of the vented door assembly 501 to the data centre control system. Apertures 508 are provided in the frame 502 to accommodate the connector linking a services distribution module to its adjacent cold aisle services module (not shown in FIG. 9). The vented door assembly 501 is also provided with pre-wired switches 509 and electrical sockets 510.

Figure 10:
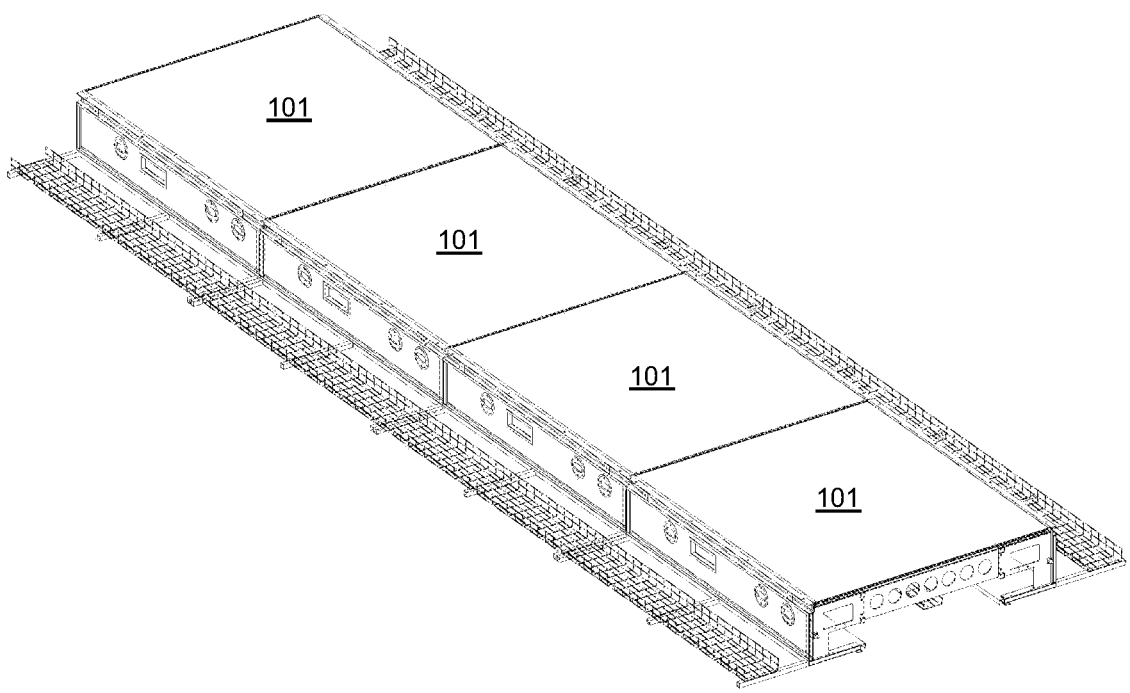
FIG. 10 shows a top perspective view of four of the cold aisle services modules of FIG. 1 assembled together.

FIG. 10 shows a top perspective view of four of the cold aisle services modules 101 of FIG. 1 assembled together. In this embodiment, the cold aisle services modules 101 are held together by means of clamps (not shown in FIG. 10).

Figure 11:
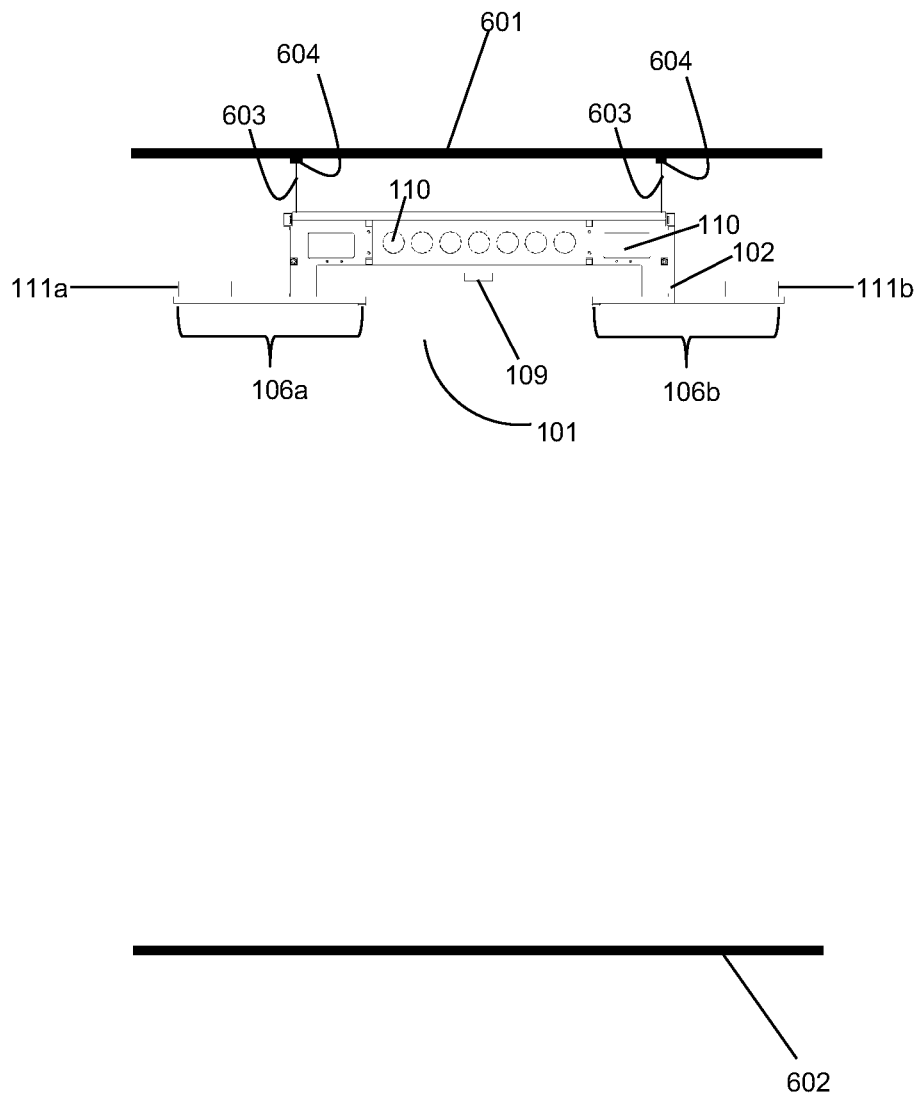
FIG. 11 shows an end elevation view of the cold aisle services module of FIG. 1 installed in a building.

FIG. 11 shows an end elevation view of the cold aisle services module 101 of FIG. 1 installed in a building having a roof 601 and a floor 602. Selected parts of the cold aisle services module 101 visible in FIG. 11 are labelled with the same reference numerals used in FIG. 1. The cold aisle services module 101 is suspended from the roof 601 of the building by means of hanging rods 603. The hanging rods 603 are fixed to fixing locations 604 provided on the roof 601 of the roof the building.

Figure 12:
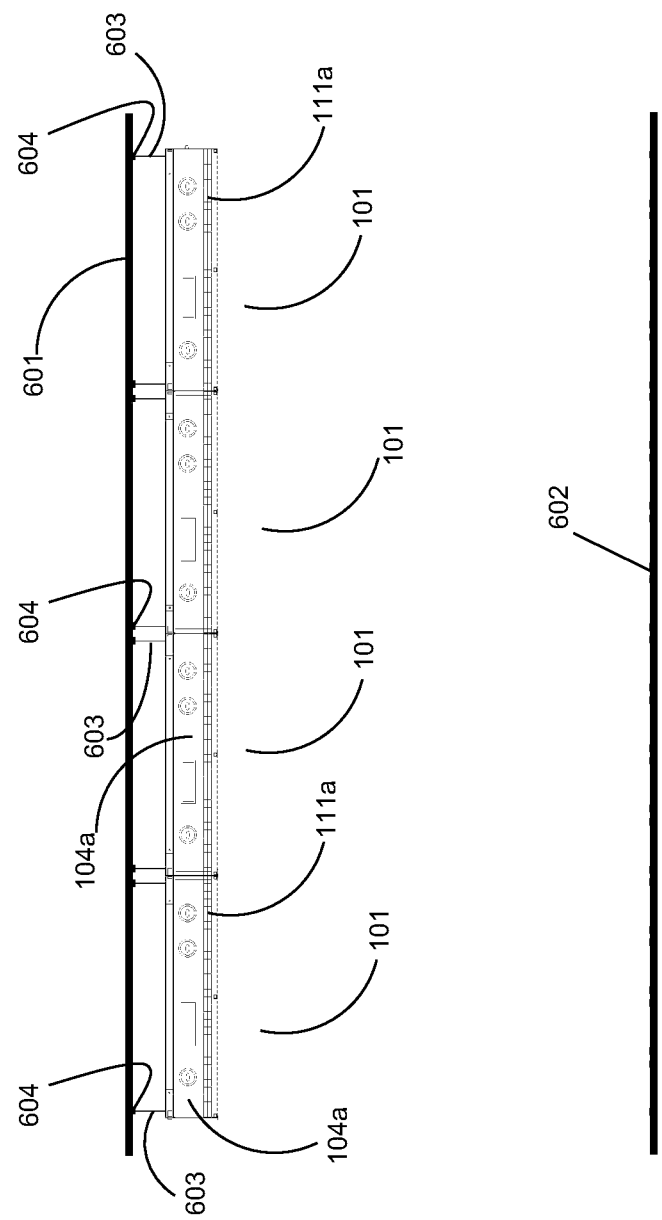
FIG. 12 shows a side elevation view of an embodiment of the installation of FIG. 11.

FIG. 12 shows a side elevation view of the installation of FIG. 11. Selected parts of the installation that are the same as shown in FIGS. 1 and 11 are labelled with the same reference numerals used in FIGS. 1 and 11. In the view shown in FIG. 12, four cold aisle services modules 101 are joined together. The cold aisle services modules 101 are held together by clamps (not shown in FIG. 12).

Figure 13:
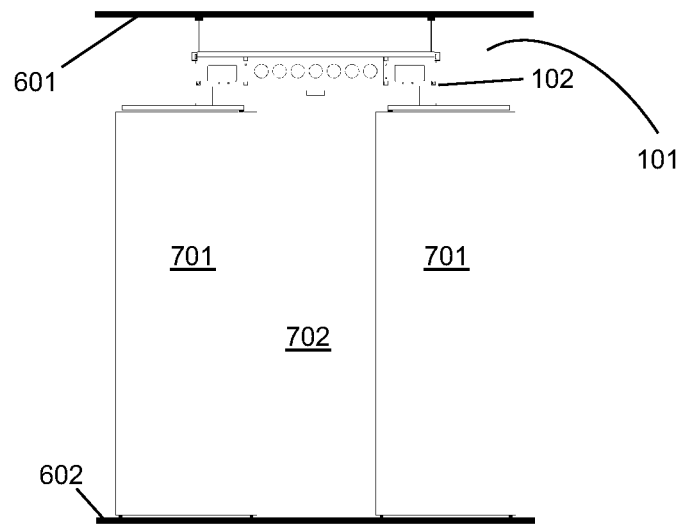
FIG. 13 shows an end elevation view of another embodiment of the installation of FIG. 11.

FIG. 13 shows an end elevation view of an embodiment of the installation of FIG. 11 with racks 701 positioned under the cold aisle services module 101. Selected parts of the installation of FIG. 11 visible in FIG. 13 are labelled with the same reference numerals used in FIG. 11. In the embodiment shown in FIG. 13, the gap between the frame 102 of the cold aisle services module 101 and the floor 602 of the building corresponds to the height of the racks 701. The floor 602, the racks 701 and the cold aisle services module 101 (including the integrated blanking portions of the cold aisle services module 101) together define a cold aisle 702.

Figure 14:
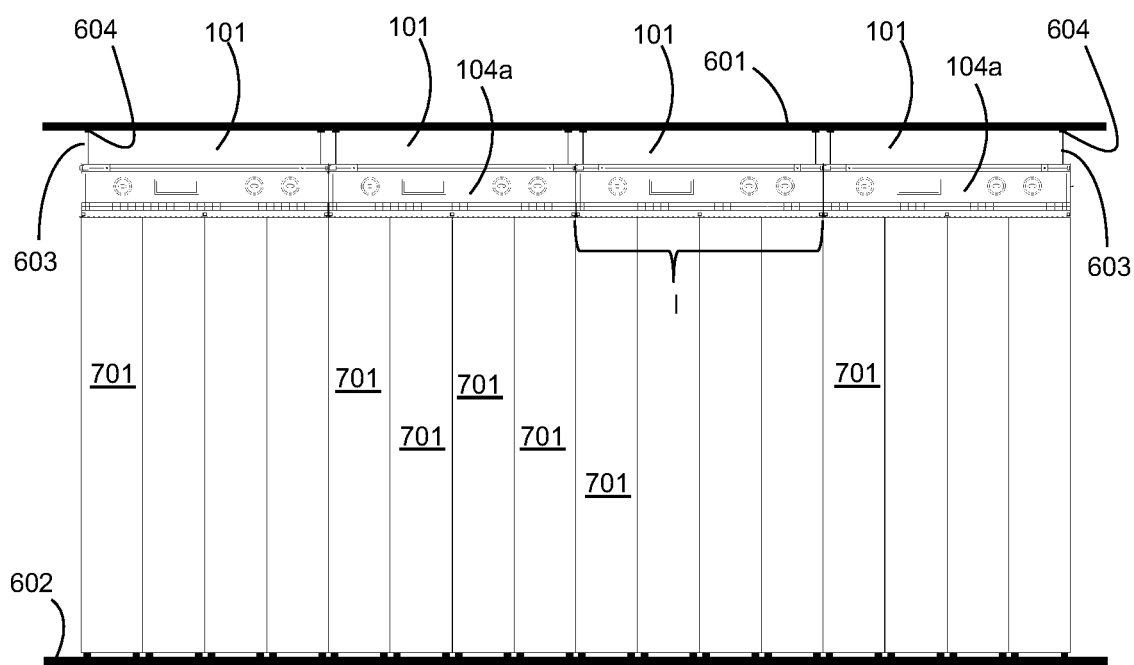
FIG. 14 shows a side elevation view of the installation embodiment of FIG. 13.

FIG. 14 shows a side elevation view of the installation embodiment of FIG. 13. Selected parts of the embodiment that are the same as shown in FIGS. 1 and 13 are labelled with the same reference numerals used in FIGS. 1 and 13. In the view shown in FIG. 15, four cold aisle services modules 101 are joined together. The cold aisle services modules 101 are held together by clamps (not shown in FIG. 14). Each cold aisle services module has a length l that corresponds to the width of four IT racks 701.

Figure 15:
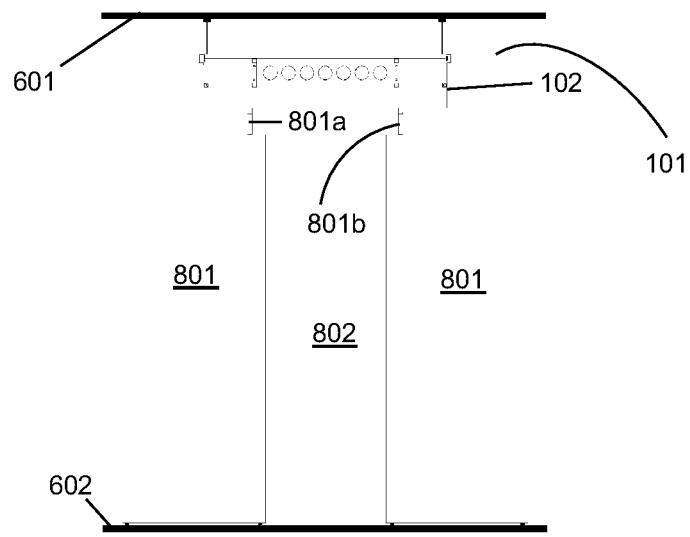
FIG. 15 shows an end elevation view of another embodiment of the installation of FIG. 11.

FIG. 15 shows an end elevation view of another embodiment of the installation of FIG. 11 with racks 801 positioned under the cold aisle services module 101. Selected parts of the installation of FIG. 11 visible in FIG. 15 are labelled with the same reference numerals used in FIG. 11. In the embodiment shown in FIG. 12, the gap between the frame 102 of the cold aisle services module 101 and the floor 602 of the building is larger than corresponds to the height of the racks 801. In the embodiment shown in FIG. 15, the cold aisle services module 101 additionally comprises bottom integrated blanking portions 801*a* and 801*b* extending downwards from the frame 102 of the cold aisle services module 101. The floor 602, the racks 801 and the cold aisle services module 101 (including the integrated blanking portions of the cold aisle services module 101) together define a cold aisle 802.

Figure 16:
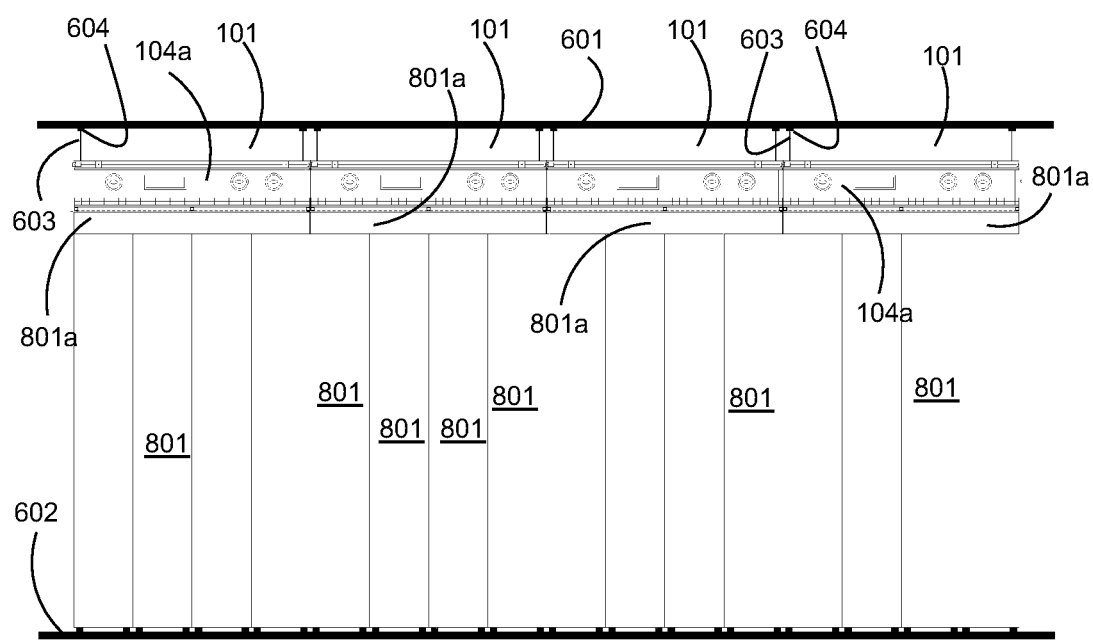
FIG. 16 shows a side elevation view of the installation embodiment of FIG. 15.

FIG. 16 shows a side elevation view of the installation embodiment of FIG. 15. Selected parts of the embodiment that are the same as shown in FIGS. 1 and 15 are labelled with the same reference numerals used in FIGS. 1 and 15. In the view shown in FIG. 16, four cold aisle services modules 101 are joined together. The cold aisle services modules 101 are held together by clamps (not shown in FIG. 16). Each cold aisle services module has a length l that corresponds to the width of four IT racks 801.

Figure 17:
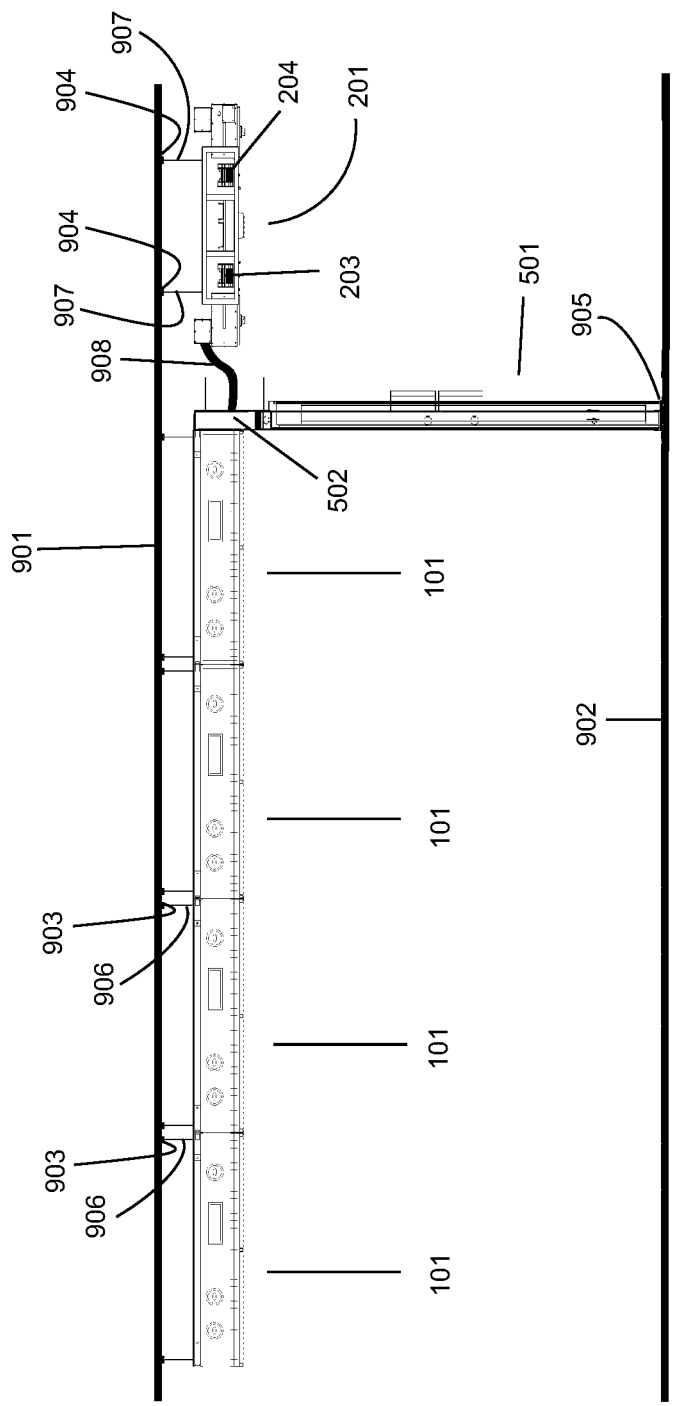
FIG. 17 shows a side elevation view of an installation of four of the cold aisle services modules of FIG. 1 in a building.

FIG. 17 shows a side elevation view of an installation of four of the cold aisle services modules 101 of FIG. 1 in a building having a roof 901 and a floor 902. Also shown in FIG. 17 is the services distribution module 201 of FIG. 3 and the vented door assembly 501 of FIG. 9. The roof 901 is provided with fixing locations 903 for the cold aisle services modules, fixing locations 904 for the services distribution module 201, and fixing location 905 for the vented door assembly 501. The cold aisle services modules 101 are suspended from the fixing locations 903 by hanging rods 906. The services distribution module 201 is suspended from the fixing locations 904 by hanging rods 907. The vented door assembly 201 is secured to the fixing location 905 by bolts (not shown). The electrical main and backup power buses 203 and 204 of the services distribution module 201 are connected to electrical power buses (not shown) on the cold aisle services modules 101 by flexible connector 908. The flexible connector 908 passes through an aperture (not shown in FIG. 17) in the frame 502 of the vented door assembly 501.

Figure 18:
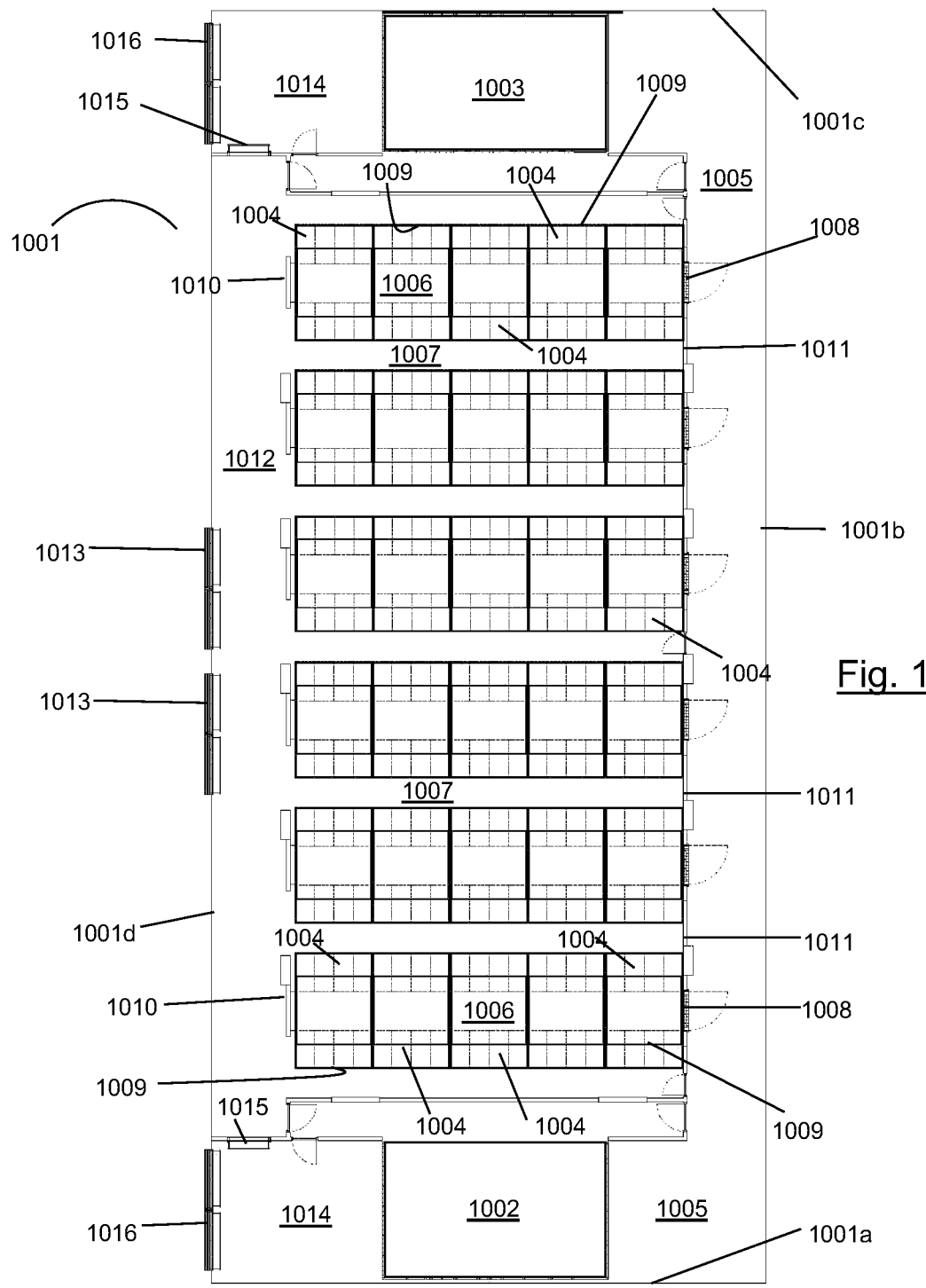
FIG. 18 shows a top plan view of a data centre.

FIG. 18 shows a top plan view of a data centre 1001. The data centre 1001 comprises a building having external walls 1001a, 1001b, 1001c and 1001d. The data centre 1001 comprises air handling units 1002 and 1003 which provide cooling air to IT equipment housed in IT racks 1004 via an air supply corridor 1005 and cold aisles 1006. The air handling units are also examples of one of the prefabricated data centre elements that form the completed data centre. The cold aisles are arranged in parallel rows separated by interleaved hot aisles 1007. Vented door assemblies 1008 are provided at the ends of each cold aisle 1006 and provide personnel access to the cold aisles 1006 from the air supply corridor, the vented door assemblies 1008 having a controllable vent (not shown in FIG. 18) for regulating the flow of cooling air into each cold aisle 1006 from the air supply corridor 1005. Each cold aisle 1006 is enclosed at the top by five cold aisle services modules 1009. Each cold aisle 1006 comprises 40 IT racks 1004 arranged in two parallel rows. The cold aisles are defined by the floor of the building of the data centre 1001, the five cold aisle services modules 1009 and the two rows of 20 IT racks 1004. A wall 1010 is provided to close off the end of each cold aisle 1006 opposite the vented door assembly 1008 of the cold aisle 1006. A wall 1011 is provided at the end of each hot aisle 1007 to separate the hot aisles 1007 from the air supply corridor 1005. At the end of each hot aisle 1007 opposite to the wall 1011, the hot aisles 1007 open out into an air exhaust corridor 1012. Air exhaust damper units 1013 are provided in the wall of the air exhaust corridor 1012 for controlling the flow of air out of the data centre 1001. The data centre 1001 also comprise an air mixing chamber 1014 connected to each of the air handling units 1002 and 1003. The air mixing chambers 1014 are separated from the air exhaust corridor 1012 by walls, in which walls are provided air recirculation damper units 1015 for controlling the flow of warm air from the air exhaust corridor 1012 into the air mixing chamber 1014. An air intake damper unit 1016 is provided in another wall of each of the two air mixing chambers for controlling the flow of outside air into the data centre 1001. In an embodiment of the data centre 1001 of FIG. 18, each of the cold aisle services modules 1009 is the cold aisle services module 101 of FIG. 1, each of the vented door assemblies 1008 is the vented door assembly 501 of FIG. 9, each of the air intake damper units 1016 and the air exhaust damper units 1013 is the air inlet/exhaust damper unit 301 of FIG. 5, and each of the air recirculation damper units 1015 is the air recirculation damper unit 401 of FIG. 7. The air supply corridor 1005 is defined in part by walls 1001a, 1001b, 1001c and 1011 of the building, as well as by the vented door assemblies 1008. The air exhaust corridor 1012 is defined in part by the walls 1001d and 1010 of the building. The air mixing chambers 1014 are defined in part by walls 1001a and 1001c of the building. Other walls of the building are shown more clearly in FIG. 18. In an embodiment of the data centre 1001 of FIG. 18, walls 1001a, 1001b, 1001c and 1001d are external walls of the building. Walls 1001a, 1001b and 1001c, which define on their interior a surface in the cold area of the data centre 1001 (the cold area being made up of the air supply corridor 1005 and the cold aisles 1006), have an average U-value of 0.15 W/m²K and have no portion extending from the exterior of the data centre 1001 to an interior surface of the cold area having a cross-sectional area of 1 cm² with a U-value greater than 0.5 W/m²K. Walls 1001a, 1001b and 1001c also have an average air permeability of 0.1 m³/m²h at 50 Pa, and have no region arranged to define a 1 cm² part of a surface in the cold area with an air permeability of greater than 0.5 m³/m²h at 50 Pa. Wall 1001d, which defines on its interior a surface in the hot area of the data centre 1001 (the hot area being made up of air exhaust corridor 1012 and the hot aisles 1007), has an average U-value of 0.2 W/m²K and has no portion extending from the exterior of the data centre 1001 to an interior surface of the hot area having a cross-sectional area of 1 cm² with a U-value greater than 1.0 W/m²K. Wall 1001d also has an average air permeability of 0.5 m³/m²h at 50 Pa, and has no region arranged to define a 1 cm² part of a surface in the hot area with an air permeability of greater than 1 m³/m²h at 50 Pa.

Figure 19:
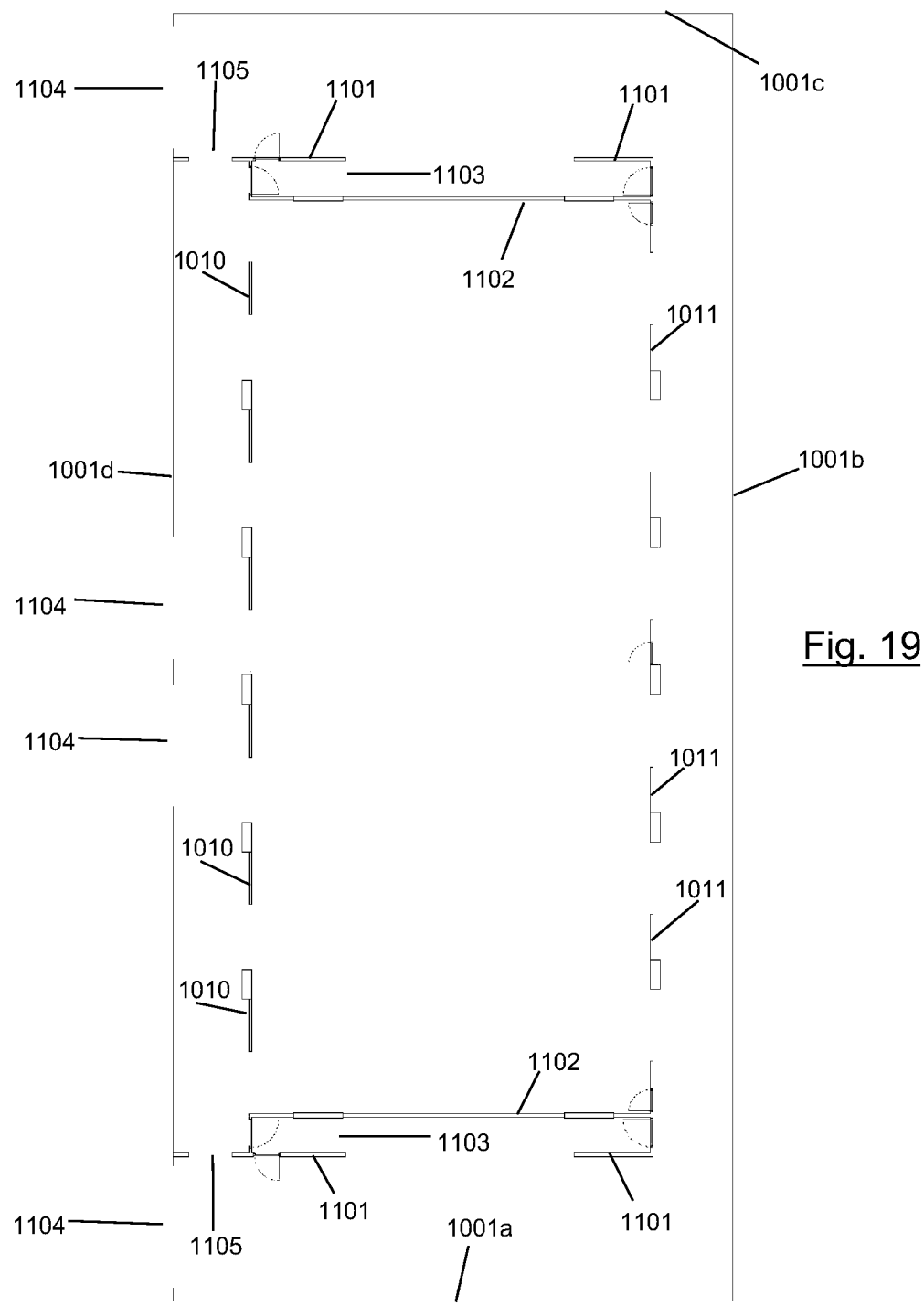
FIG. 19 shows a top plan view of the building of the data centre of FIG. 18 prior to installation of the prefabricated data centre elements.

FIG. 19 shows a top plan view of the building of the data centre 1001 of FIG. 18 prior to installation of the prefabricated data centre elements. The parts of the building of FIG. 18 shown in FIG. 19 are labelled with the same reference numerals used in FIG. 18. The building comprises various internal walls that are set out to cooperate with the prefabricated data centre elements to define the various parts of the data centre when those elements are installed. In particular, the building is provided with various internal walls 1010 and 1011 that cooperate with the vented door assemblies, the cold aisle services modules and the IT racks to define the air supply corridor, the hot and cold aisles and the air exhaust corridor when those elements are installed. The building also comprises internal walls 1101 that are positioned to cooperate with the air handling units to define the air mixing chambers and the air supply corridor. The building further comprises internal walls 1102 that are positioned to cooperate with the internal walls 1101 and the air handling units to define data centre control rooms 1103. Internal walls 1102 are also positioned to cooperate with the IT racks to define hot aisles. Apertures 1104 are provided in wall 1001d to accommodate the air intake damper units and the air exhaust damper units. Apertures 1105 are provided in internal wall 1101 to accommodate the air recirculation damper units.

Figure 20:
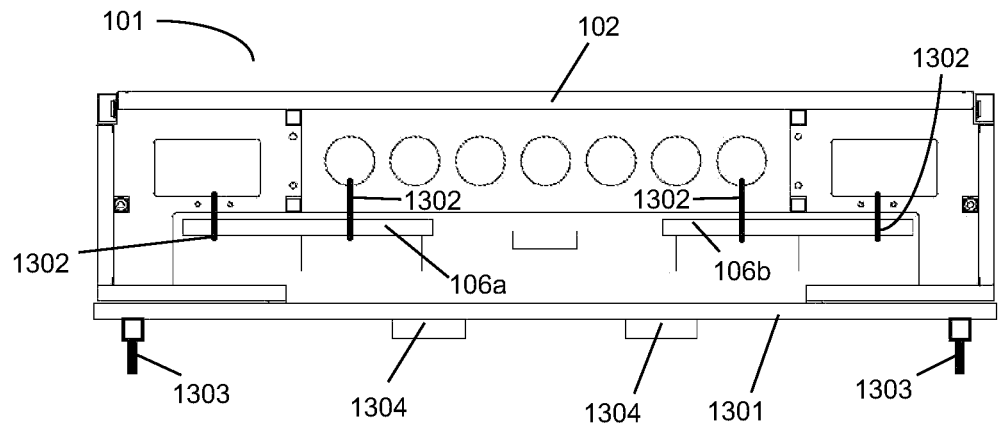
FIG. 20 shows an end elevation view of the cold aisle services module of FIG. 1 in a transport configuration and mounted on a secondary steel frame.

FIG. 20 shows an end elevation view of the cold aisle services module 101 of FIG. 1 in a transport configuration and mounted on a secondary steel frame 1301. In the transport configuration shown in FIG. 20, the hot aisle service portions 106a and 106b have been detached from the frame 102 of the cold aisle services module 101 and temporarily secured within the body of the cold aisle services module 101 using cable ties 1302. The secondary steel frame 1301 comprises detachable wheels 1303 allowing the frame 1301 and the module 101 to be conveniently moved around on a floor. The secondary steel frame 1301 also comprises forklift slots 1304 to allow the frame 1301 and the module 101 to be conveniently picked up using a vehicle with a forklift attachment.

Figure 21:
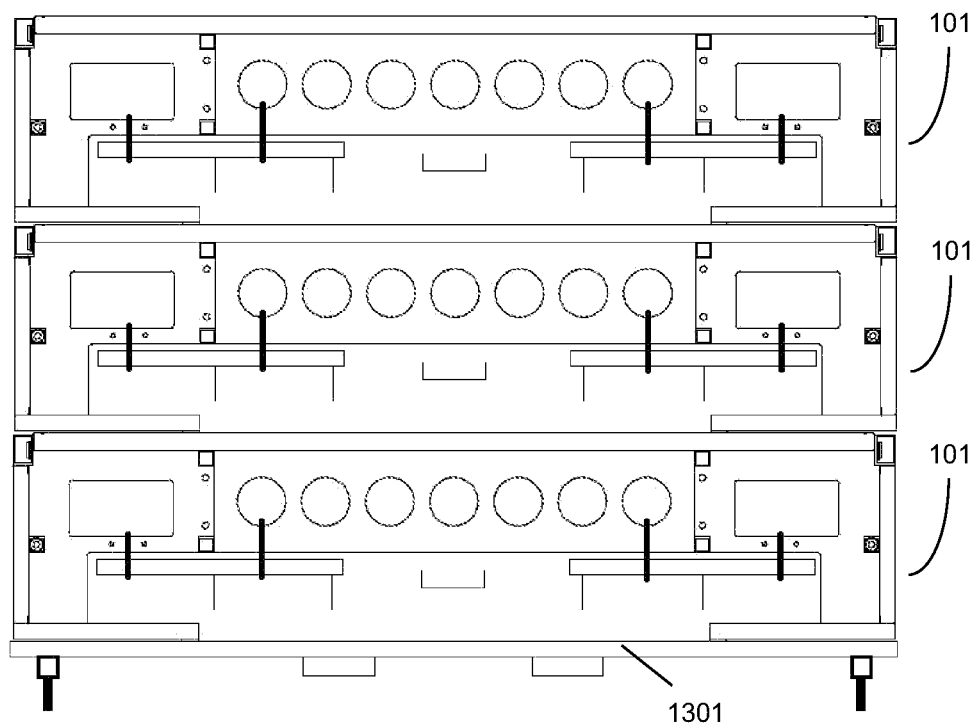
FIG. 21 shows an end elevation view of three of the cold aisle services modules of FIG. 1 stacked on top of each other on the secondary steel frame of FIG. 20.

FIG. 21 shows an end elevation view of three of the cold aisle services modules 101 of FIG. 1 stacked on top of each other on the secondary steel frame 1301 of FIG. 20. Using the stacked arrangement shown in FIG. 21, three cold aisle services modules can be conveniently and safely transported and manipulated at once. Alternatively, four or more cold aisle services modules could be stacked on top of each other on the secondary steel frame 1301.

Figure 22:
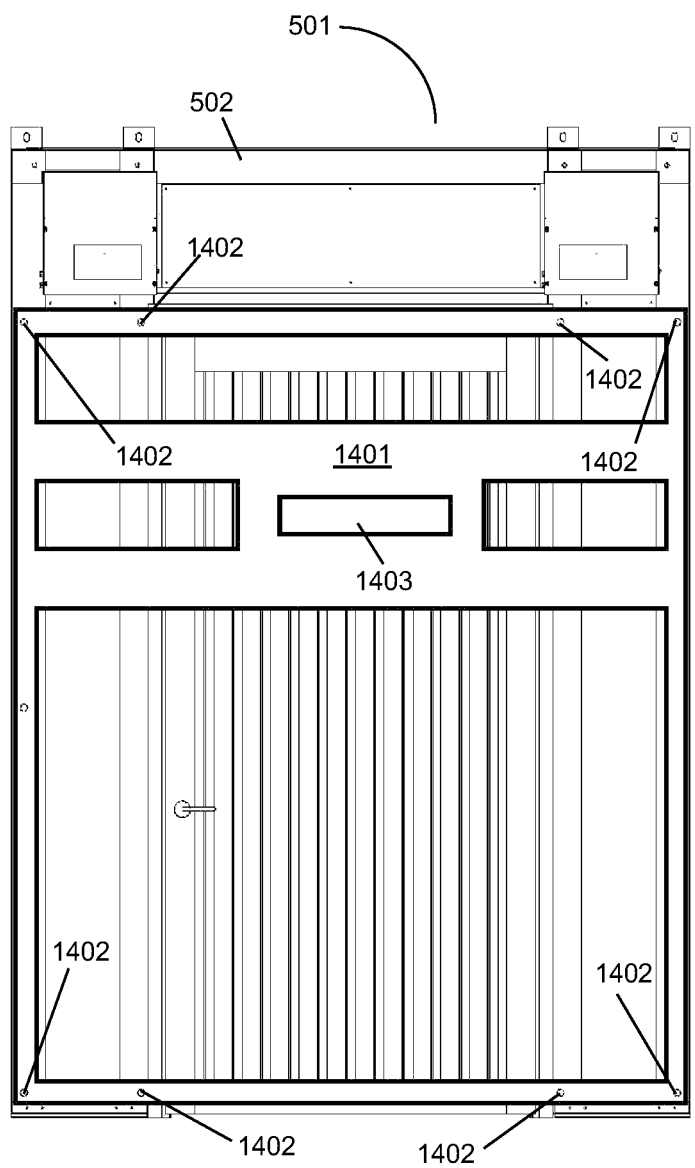
FIG. 22 shows a rear elevation view of the vented door assembly of FIG. 9 mounted on a secondary steel frame.

FIG. 22 shows a rear elevation view of the vented door assembly 501 of FIG. 9 mounted on a secondary steel frame

1401. The vented door assembly 501 is secured to the secondary steel frame 1401 by means of bolts 1402. The secondary steel frame 1401 supports the vented door assembly 501 during transport, and the secure joining of the frame 1401 to the door assembly 501 by means of the bolts 1402 allows the door assembly 501 to be rotated from an upright to a flat position without the door assembly distorting. The secondary steel frame 1401 also acts as a jig. For example, various parts of the frame 502 of the vented door assembly 501 may be bolted to the secondary steel frame 1402 during construction of the vented door assembly 501. The secondary steel frame 1401 comprises a fastening means 1403 allowing the frame 1401 to be fasted to a lifting and tilting device (not shown in FIG. 22). In order to rotate the secondary steel frame 1401 with the vented door assembly 501 attached, the lifting and tilting device is fastened to the frame 1401 using the fastening means, then lifted and tilted. The secondary steel frame 1401 also comprises forklift slots 1404 (see FIG. 22) to allow the frame 1401 and the vented door assembly 501 to be conveniently picked up using a vehicle with a forklift attachment when the frame 1401 and the vented door assembly 501 has been rotated to a horizontal position.

Figure 23:
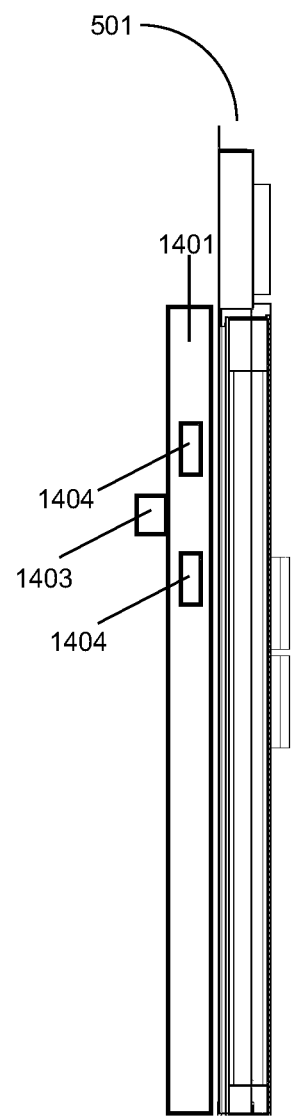
FIG. 23 shows a side elevation view of the vented door assembly and secondary steel frame of FIG. 22.

FIG. 23 shows a side elevation view of the vented door assembly 501 and secondary steel frame 1401 of FIG. 22. Certain parts of the vented door assembly 501 and the secondary steel frame 1401 are labelled using the same referenced numerals used in FIG. 22.

Figure 24:
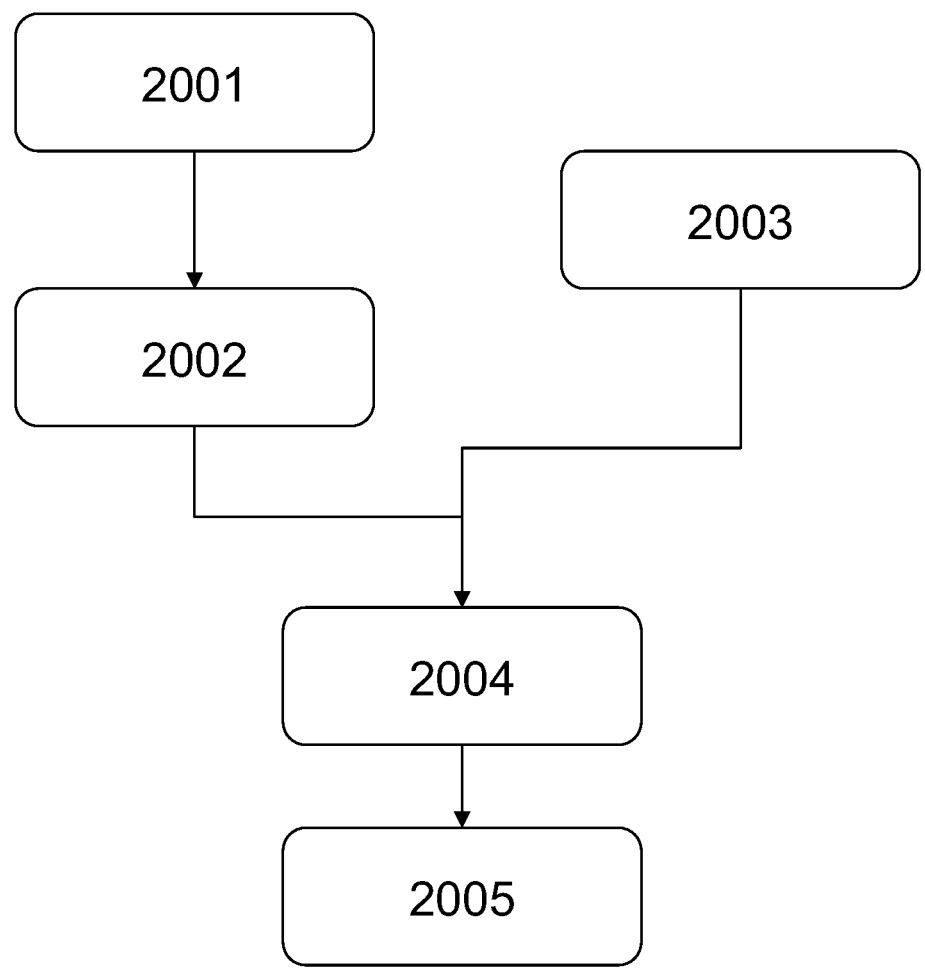
FIG. 24 shows a flow chart illustrating an embodiment of a method of constructing a data centre according to the invention.

FIG. 24 shows a flow chart illustrating an embodiment of a method of constructing a data centre according to the invention. The method shown in the flow chart of FIG. 24 comprises a step 2001 of providing a building having a floor, walls and a roof, followed by a step 2002 of checking that the building meets certain pre-specified criteria, including requiring an aperture for forming an air inlet and an aperture for forming an air outlet. Simultaneously to the performance of steps 2001 and 2002, the method comprises a step 2003 of providing multiple prefabricated data centre elements including an air handling unit, multiple cold aisle services modules, one or more services distribution modules and one or more damper units. The method of the embodiment illustrated in FIG. 24 thus efficiently allows the manufacture of the prefabricated data centre elements to be completed while building construction is ongoing. The embodiment of FIG. 24 further comprises a step 2004 of installing in the interior of the building provided by steps 2001 and 2002 the prefabricated data centre elements provided by step 2003 to provide a data centre, followed by a step 2005 of installing IT equipment in the data centre.

According to a further embodiment of the method of the invention, the step 2002 of checking that the building meets certain pre-specified criteria includes using a template to check that the building is provided with correctly positioned fixing locations for fixing the prefabricated data centre elements to the building. The template comprises an elongate steel member marked with the correct spacing for at least two separate fixing locations, the steel being high-quality steel that has an acceptable low variation of size when exposed to variations in temperature. According to a further embodiment of the method of the invention, the step 2002 of checking that the building meets certain pre-specified criteria includes checking that the walls, floor and ceiling of the building have appropriate levels of insulation to avoid condensation of water in the data centre when the temperature outside the building is at expected winter temperature lows. According to a further embodiment of the method of the invention, the step 2002 comprises checking that the walls, floor and roof of the building have a sufficient air tightness to provide a fan power degradation of no more than 5%. According to a further embodiment of the method of the invention, the step 2002 of checking that the building meets certain pre-specified criteria includes checking that the fixing locations provided for the prefabricated data centre elements have appropriate load-bearing capacities, checking that the building is provided with an appropriate power source, checking that the building is adequately weatherproof, checking that the building includes a suitable amount of open space, and checking that the building includes a suitably large obstruction-free space to accommodate an air handling unit.

Figure 25:
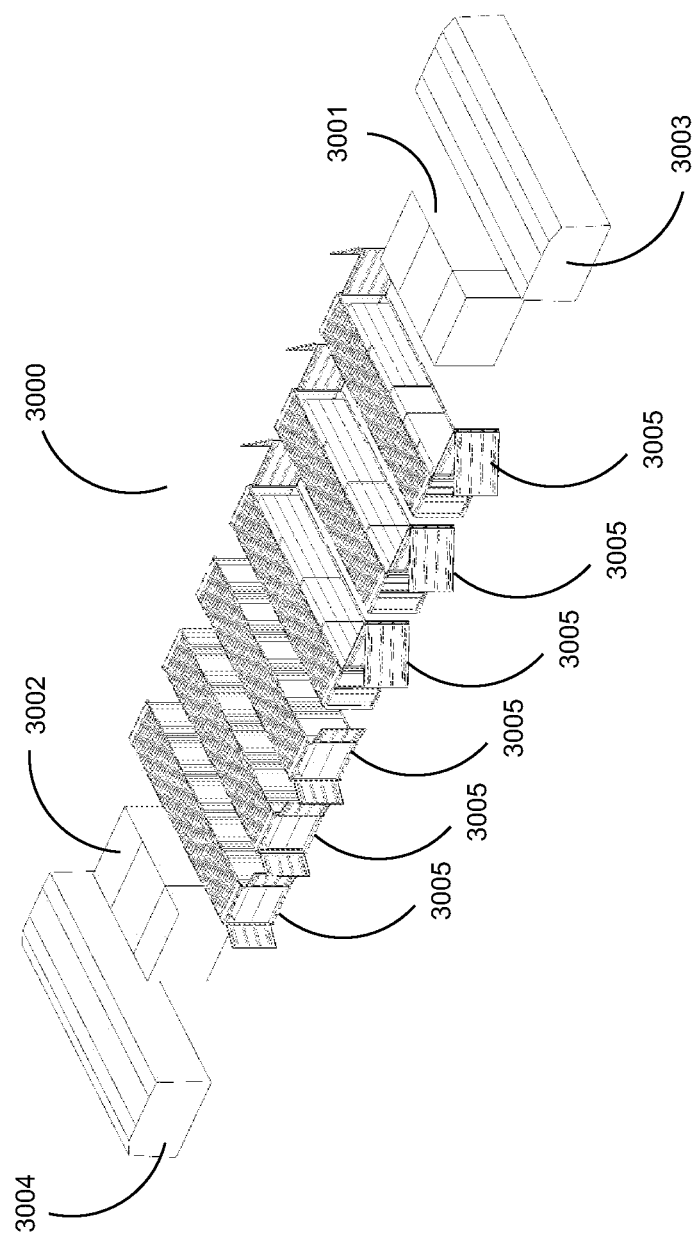
FIG. 25 shows a top perspective view of a set of prefabricated data centre elements packaged up into a transport configuration.

FIG. 25 shows a top perspective view of a set 3000 of prefabricated data centre elements packaged up into a transport configuration. The set 3000 of data centre elements comprises two air handling units 3001 and 3002 which are wrapped up as oversize consignments, two external plant decks 3003 and 3004 accommodating mechanical cooling equipment, the external plant decks 3003 and 3004 also being wrapped up as oversize consignments, and six standard size (40 ft. long) shipping containers 3005 packed with prefabricated data centre elements including: thirty cold aisle services modules, six vented door assemblies, six services distribution modules, two air intake damper units, two air exhaust damper units and two air recirculation damper units. The mechanical cooling equipment of the external plant decks 3003 and 3004 provides cooling fluid to the air handling units of the data centre for use when 'free air cooling' does not meet the cooling requirements of the IT equipment in the data centre, or on occasions when the ambient air outside the data centre is unsuitable for use as cooling air, for example in the event of excess smoke and/or particulate levels in the ambient air. The air intake/exhaust/recirculation damper units and the vented door assemblies are rotated into a horizontal orientation for packing into the shipping containers 3005 because the height of those elements is too large to fit into a standard shipping container when in the vertical working orientation. In the transport configuration shown in FIG. 25, the set 3000 of prefabricated data centre elements occupies a significantly smaller volume that those elements occupy when in the deployed configuration of the set 3000 (shown in FIG. 26). Each shipping container 3005 occupies a volume of about 77 m$^3$, and each of the two air handling units 3001 and 3002 occupies a volume of about 92 m$^3$ when packaged, giving a total consignment volume (excluding the external plant decks 3003 and 3004) of about 646 m$^3$.

Figure 26:
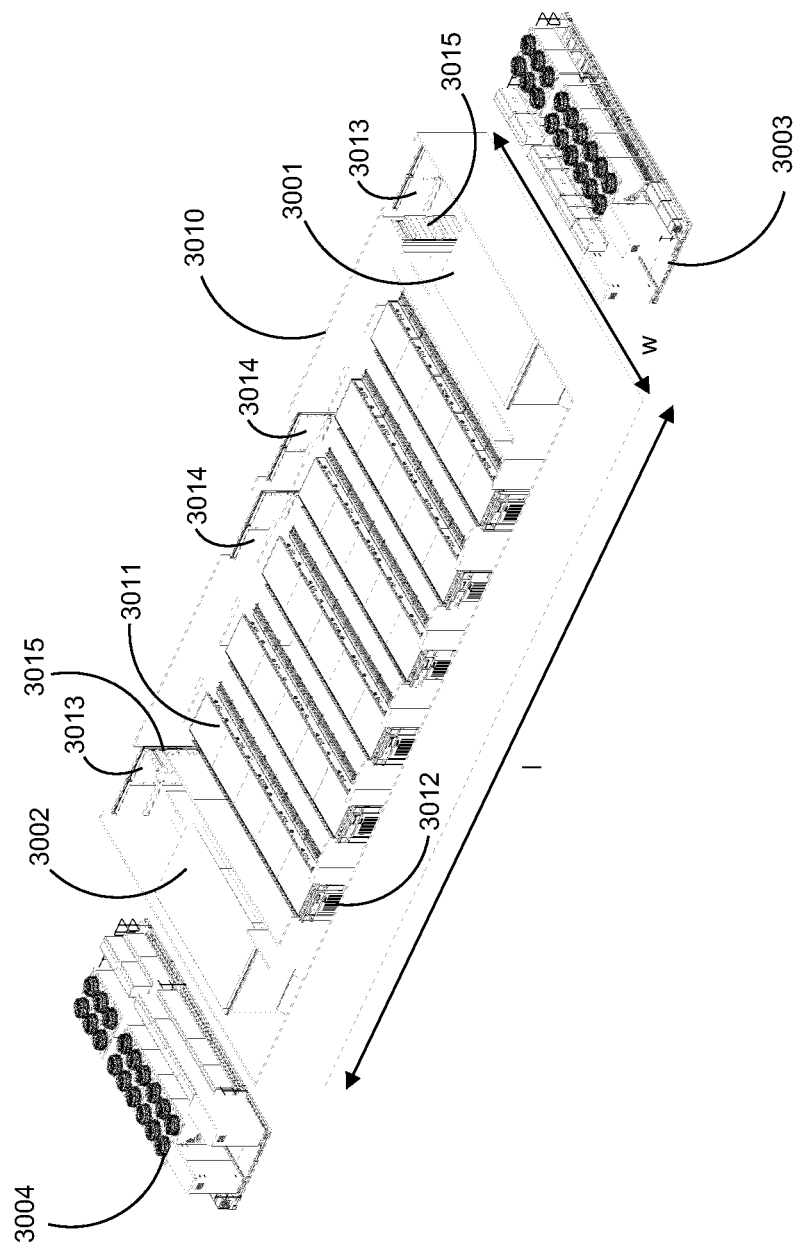
FIG. 26 shows a top perspective view of the set of prefabricated data centre elements of FIG. 25 in their deployed configuration in a data centre building envelope.

FIG. 26 shows a top perspective view of the set of prefabricated data centre elements of FIG. 25 in their deployed configuration in a data centre building envelope 3010. The two external plant decks 3003 and 3004 are installed on site outside of the data centre building envelope 3010. The two air handling units 3001 and 3002, thirty cold aisle services modules 3011, six vented door assemblies 3012, six services distribution modules (not shown in FIG. 28), two air intake damper units 3013, two air exhaust damper units 3014 and two air recirculation damper units 3015 are installed inside the data centre building envelope 3010. The six services distribution modules (not shown in FIG. 26) are suspended in an air supply corridor running along the side of the data centre building envelope 3010 adjacent to the vented door assemblies 3012. The data centre building envelope occupied by the prefabricated data centre elements (excluding the two external plant decks 3003 and 3004) has a length l of around 40 m, a width w of around 15 m, a height of around 3 m. It will be understood that the volume occupied by the prefabricated data centre elements in their deployed position is thus 1,800 m³ (giving a transport volume to deployed volume ratio of about 1:3. The deployed configuration volume of the thirty cold aisle services modules 3011, six vented door assemblies 3012, six services distribution modules (not shown in FIG. 28), two air exhaust damper units 3014 and two air recirculation damper units 3015 (which, as shown in FIG. 25, are packed into six shipping containers having a total volume of 462 m³) is around 1,500 m³ (giving a transport volume to deployed volume ratio of around 1:3). Whilst the present invention has been described and illustrated with reference to particular embodiments, it will be appreciated by those of ordinary skill in the art that the invention lends itself to many different variations not specifically illustrated herein. In particular, it will be appreciated that the integrated blanking portions of the cold aisle services module may be secured to the module by any means, for example using clips or rivets, by slotting into slots provided in the frame of the module, but using an adhesive or by means of screws and/or bolts, for example. The frame of the data centre services modules may be made by any suitable material, such as a plastic material, provided that the material provides an adequate level of rigidity and strength to support the weight of the data centre services and the integrated blanking portions. The data centre services modules (including the cold aisle services modules and the services distribution modules) may be secured to the structure of the building by any suitable means. For example the modules may be hung from a ceiling or from beams/joists using hanging rods or cables. Additionally or alternatively, the modules may be secured into slots provided on the building using slot-engaging portions provided on the modules, and vice versa. Additionally or alternatively, the modules may be attached to the building by bolting them directly to the ceiling and/or beams/joists of the building. It will be appreciated that the modules may be separated from ceiling and/or beams/joists of the building by any or no distance. For example, where the modules are installed in a space within a building having a ceiling height of 4 metres or greater, the modules may be separated from the ceiling by a distance of 1 metre or greater, whereas if the ceiling height is only 3 metres, the modules may be secured in direct contact with the ceiling.

Figure 27:
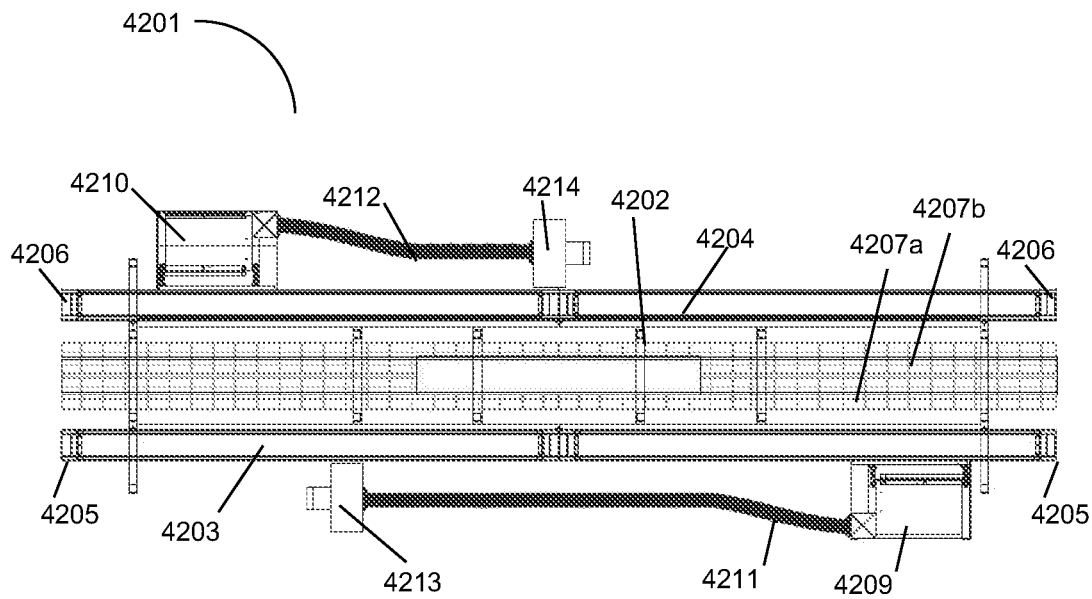
FIG. 27 shows a top plan view of an embodiment of a services distribution module according to the eighth aspect of the invention.

FIG. 27 shows a top plan view of an embodiment of the services distribution module 4201 of the eighth aspect of the invention. The services distribution module 4201 comprises a steel frame 4202. Extending along the length of the services distribution module 4201 are a main electrical power bus 4203 and a backup electrical power bus 4204. The ends of the main and backup electrical power buses 4203 and 4204 are provided with slot-fitting plug and play connectors 4205 and 4206, respectively. The connectors 4205 and 4206 engage with corresponding connectors on an adjacent services distribution module via busway joint connectors (not shown in FIG. 27). The services distribution module 4201 is also provided with cable trays 4207a and 4207b for accommodating data centre services, such as cables, and with an earth rod or earth tape (not shown in FIG. 27). Connection housings 4209 and 4210 are provided for housing one end of flexible connectors 4211 and 4212. The flexible connectors 4211 and 4212 are shown in the transport configuration in FIG. 27, with the distal ends 4213 and 4214 of the connectors releasably connected to the frame 4202 with brackets (not shown in FIG. 27).

Figure 28:
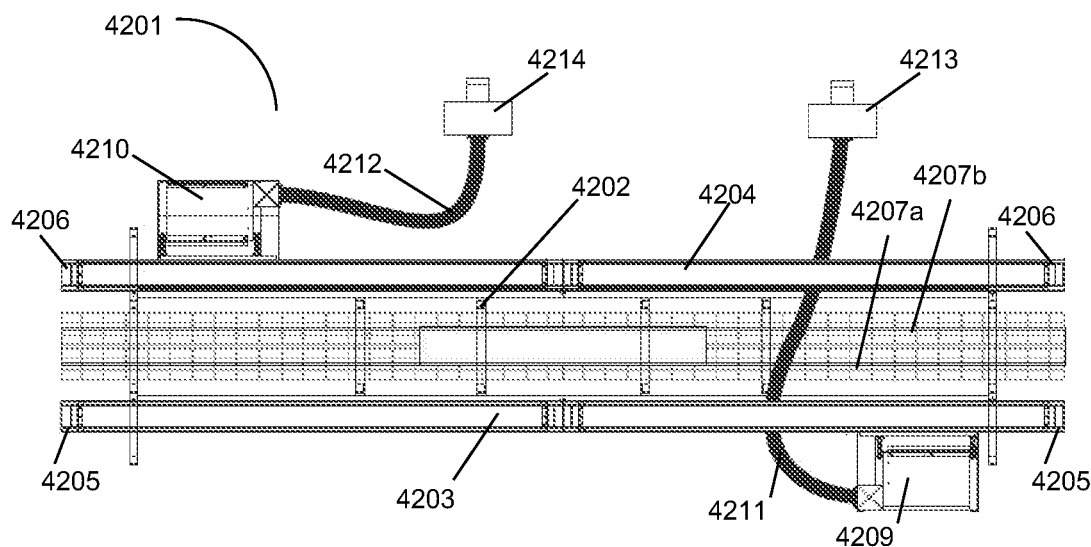
FIG. 28 shows another top plan view of the services distribution module of FIG. 27.

FIG. 28 shows a top plan view of the services distribution module 4201 of FIG. 27 with the flexible connectors 4211 and 4212 shown in the deployed configuration. In the deployed configuration, the distal ends 4213 and 4214 of the flexible connectors 4211 and 4212 are connected to a cold aisle services module (not shown in FIG. 28). The remaining parts of the services distribution module 4201 of FIG. 28 are labelled with the same numerals used in FIG. 27.

Figure 29:
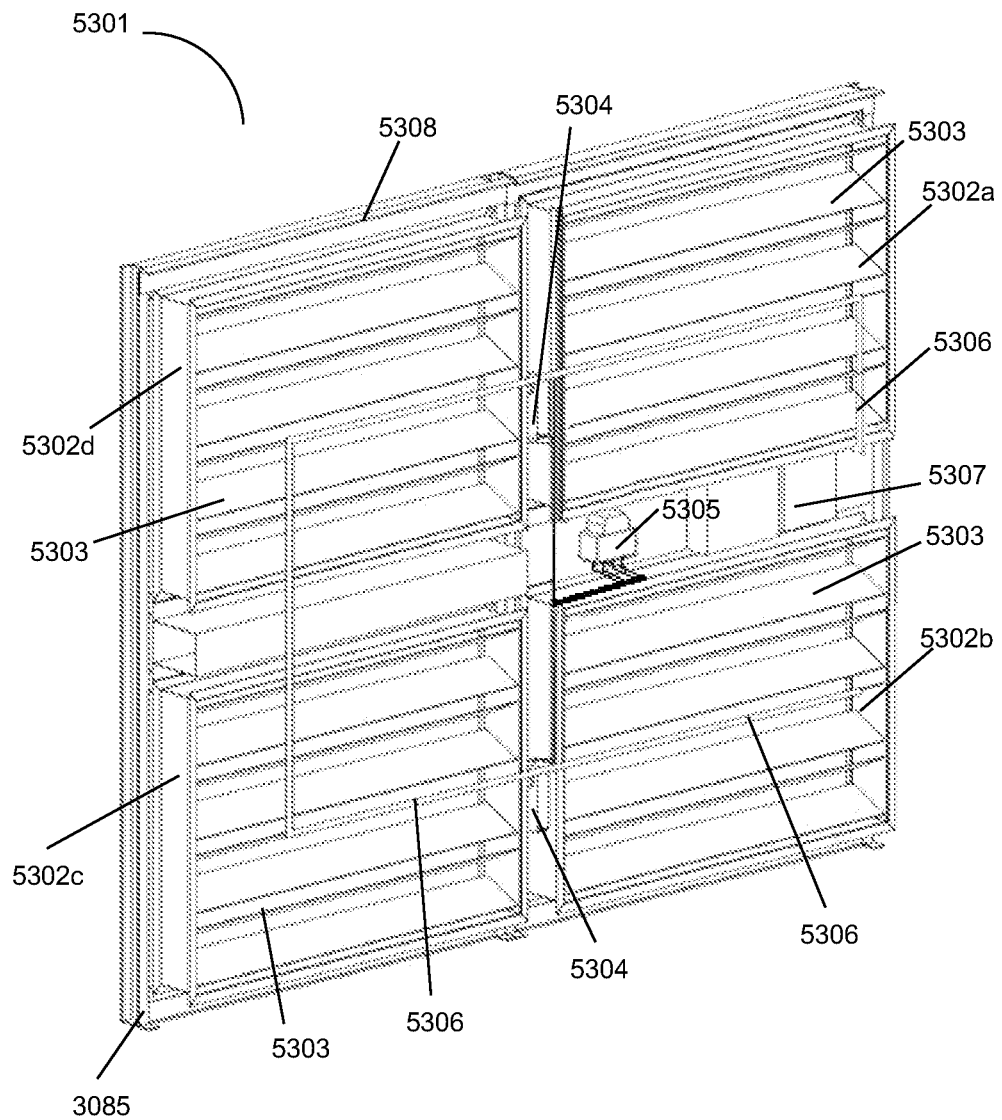
FIG. 29 shows a perspective view of an embodiment of a damper unit according to the ninth aspect of the invention; and, FIG. 30 shows an end elevation view of an embodiment of a supporting frame assembly according to the seventh aspect of the invention.

FIG. 29 shows a perspective view of an embodiment of a damper unit 5301 according to the ninth aspect of the invention. The damper unit 5301 comprises four controllable vents 5302a to 5302d each including a set of controllable louvres 5303. Each controllable vent is in the form of a shroud around each set of louvres. The louvres 5303 are continuously adjustable between fully closed and fully open positions, and are shown in a partially open position in FIG. 29. The louvres are adjusted by actuators 5304 provided for each of the vents 5302a to 5302d (only the actuators 5304 of vents 5302a and 5302b are shown in FIG. 5). The actuators 5304 are controlled by a pre-wired vent control system 5305 provided with plug-and-play connectors (not shown in FIG. 29) for connecting the vent control system to the main data centre control system. The air intake damper unit 5301 is also provided with a pre-wired temperature and humidity sensor (not shown in FIG. 29) for measuring the temperature and humidity of air entering the data centre through the vents 5302a to 5302d. The sensor is provided with a plug-and-play connector (not shown in FIG. 29) ready for connection to the data centre control system. A smoke detection system comprising a sampling pipe 5306 and a sensor unit 5307 is provided on the air intake damper unit 5301. The damper unit 5301 also comprises a frame 5308 that supports its various components. The damper unit 5301 could be used as an air exhaust intake damper unit or as an air exhaust damper unit, for example. The vent control system 5305 and the sensor unit 5307 are each located on the frame 5308 behind the outwardly extending edges of the shrouds of the controllable vents 5302a to 5302d. The shrouds help to shield the vent control system 5305 and the sensor unit 5307 from moisture entrained in air flowing through the damper unit.

Figure 30:
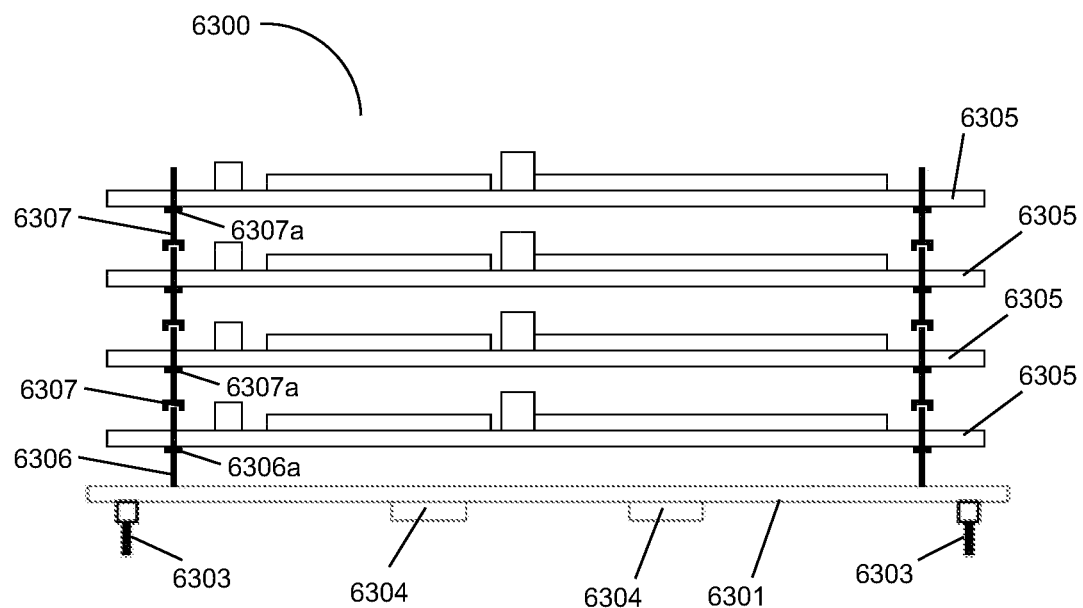

FIG. 30 shows an end elevation view of an embodiment of a supporting frame assembly 6300 according to the seventh aspect of the invention. The frame assembly 6300 is shown supporting four prefabricated data centre elements 6305 in FIG. 30. The supporting frame assembly 6300 comprises a steel frame 6301, wheels 6303 and a brake in the form of a jack for lifting two of the wheels off of the floor (the jack is not shown in FIG. 30). The supporting frame assembly 6300 also comprises forklift slots 6304 to allow the frame 6301 to be conveniently picked up using a vehicle with a forklift attachment. The supporting frame assembly further comprises support posts 6307 for supporting a prefabricated data centre element 6305 on the frame 6301. The posts 6307 pass through holes in the prefabricated data centre element 6305 and are provided with a flange 6306a on which the element 6305 rests. The prefabricated data centre elements 6305 are not suitable for stacking directly on top of each other, and so further support posts 6307 connectable to the tops of lower support posts 6306 are provided for carrying further prefabricated data centre elements 6305. The further support post 6307 also pass through holes in the further elements 6305 and having a flanges 6307a for supporting the further elements 6305. The frame 6301 is provided with brackets (not shown in FIG. 30) for securing the support posts 6306 and the further support posts 6307 when the posts are not in use.

It will be appreciated that the vented door assemblies are not an essential requirement for forming a data centre. For example, it may be that no regulation of air flow is required between the air supply corridor and the cold aisles.

It will be appreciated that the warm air produced by the IT equipment may or may not be encapsulated. For example, it may be that the hot aisles are in free fluid communication with all internal areas of the building other than the air supply corridor and the cold aisles. Alternatively, it may be that the warm air is entrained by additional blanking portions provided to encapsulate the warm air in the hot aisles and in the air exhaust corridor.

It will be appreciated that the method of the present invention may be used to construct any size of data centre. In particular, it will be appreciated that the method of the invention is fully scalable from relatively small data centres comprising 20 racks of IT equipment or fewer, up to large data centres comprising 500 racks of IT equipment or more. It will be appreciated that the method of the present invention may be used to add capacity to an existing data centre, and or complete an initial or intermediate phase of part of a larger data centre installation.

It will be appreciated that the particular pre-specified criteria may differ as between different data centre installations. For example, in certain countries (such as countries with warmer climates), cold-bridging may not be of concern. Furthermore, it may be that for certain classifications of data centre, such as for Tier 3 data centres, more stringent pre-specified criteria are required than for other classifications of data centre, such as Tier 2 or Tier 1 data centres.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

The invention claimed is:

1. A method of making a data centre in an existing building, the building having a structure comprising a floor, walls and a roof, an air inlet for supply of air into the building, and an air outlet for removal of air from the building, wherein the method includes the following steps:
 installing multiple prefabricated data centre elements by:
 connecting to the air inlet an air handling module that is arranged to provide cooling capacity for the data centre; and
 installing in the interior of the building multiple cold aisle services modules by suspending each of said cold aisle services modules from the structure of the building above and spaced apart from the floor, each of said cold aisle services modules having:
 a length and a width,
 one or more integrated blanking portions including at least one ceiling member configured to enclose a top portion of a cold aisle, and
 one or more data centre services extending along the length of the cold aisle services module and terminating in a connector that is connected to a corresponding connector of an adjacent data centre services module;
 wherein said installing the multiple cold aisle services modules comprises fastening each respective module of said cold aisle services modules to an adjacent cold aisle services module, and forming a seal between associated integrated blanking portions on adjacent cold aisle services modules;
 wherein the method additionally comprises installing in an interior of the building multiple racks of IT equipment, the racks being arranged in multiple parallel rows;
 the method being performed so that the floor, the racks, and the cold aisle services modules including the associated integrated blanking portions together define multiple parallel spaced apart cold aisles for entraining and encapsulating the flows of cooling air to the IT equipment arranged in the racks.

2. The method according to claim 1, wherein at least some of the data centre services on each of said cold aisle services modules terminates in a connector facilitating connection to a corresponding connector on an adjacent data centre services module.

3. The method according to claim 1, wherein the step of installing multiple prefabricated data centre elements includes installing one or more services distribution modules, each services distribution module having one or more data centre services terminating in a connector that is connected to a corresponding connector of a cold aisle services module.

4. The method according to claim 3, wherein each services distribution module has one or more data centre services terminating in a connector that is connected to a corresponding connector on an adjacent services distribution module.

5. The method according to claim 3, wherein the method comprises connecting each services distribution module to at least one cold aisle services module and to at least one other services distribution module.

6. The method according to claim 1, wherein the step of installing the multiple cold aisle services modules comprises moving the integrated blanking portions from a first, transport, configuration to a second, deployed, configuration.

7. The method according to claim 1, wherein the method comprises installing one or more data centre services on the cold aisle services modules and/or the data centre services module prior to installation of the module in the building.

8. The method according to claim 7, wherein the method comprises installing on the cold aisle services modules and/or the data centre services module prior to installation of the module in the building at least one item of data centre service—providing equipment selected from the list consisting of: cable trays, electrical cables, earth cables, data-carrying/network cables, fire suppression system conduits, sensor cables, sensors, lighting system cables, and lighting systems.

9. The method according to claim 1, wherein the cold aisle services module comprises at least one integrated hot aisle services portion arranged to extend across and above at least part of at least one hot aisle adjacent to the cold aisle, the integrated hot aisle services portion comprises at least one data centre hot aisle service selected from the list consisting of: data carrying/network cables, electrical cables, earth cables and components of a hot aisle lighting system.

10. The method according to claim 9, wherein the method comprises moving the at least one integrated hot aisle services portion from a first, transport, configuration to a second, deployed, configuration.

11. The method of claim 9 wherein each of said cold aisle services modules comprises two or more integrated hot aisle services portions, wherein one integrated hot aisle services portion is arranged to extend across and above at least part of an adjacent hot aisle on one side of the cold aisle, and another integrated hot aisle services portion is arranged to extend across and above at least part of another adjacent hot aisle on the other side of the cold aisle.

12. The method according to claim 1, wherein the method comprises defining an air supply corridor for transporting cooling air above the floor from the air handling module to the cold aisles.

13. The method according to claim 12, wherein the step of installing multiple prefabricated data centre elements includes installing a vented door assembly for each cold aisle, the assembly comprising a frame and a door for providing personnel access to the cold aisle from the air supply corridor, the door comprising at least one controllable vent for regulating the flow of cooling air into the cold aisle from the air supply corridor.

14. The method according to claim 1, wherein the method comprises suspending said multiple cold aisle service modules and said services distribution modules from the roof of the building.

15. The method according to claim 1, wherein method includes steps ensuring that the building meets certain pre-specified criteria, and wherein the pre-specified criteria for the building include:
specified fixing locations for fixing the prefabricated data centre elements to the building wherein the method comprises using a template to check that fixing locations are provided on the building in accordance with the pre-specified criteria prior to installation of at least some of the multiple prefabricated data centre elements, and/or wherein the pre-specified criteria for the building include providing a set of fixing points for suspending each data centre services module from the roof of the building, wherein the set of fixing points provided for each data centre services module has a load capacity of at least 150 Kg.

16. The method according to claim 15, wherein the data centre comprises a cold area, and wherein the pre-specified criteria for the building include requiring that the floor, walls and roof of the building are sufficiently insulated to prevent condensation of water on any surface in the cold area of the data centre when ambient air temperature outside of the data centre is at the typical average temperature for the coldest month at the data centre's location and when the relative humidity of the air in the cold area of the data centre is 40%.

17. The method according to claim 1, wherein the method includes a step of installing one or more prefabricated damper units in an aperture for forming an air inlet and/or a step of installing one or more prefabricated damper units in the aperture for forming an air outlet, wherein the damper unit is a prefabricated damper unit comprising: a frame, a plurality of adjustable louvres mounted on the frame, at least one actuator connected to the adjustable louvres and arranged to adjust the position of the adjustable louvres in order to control the flow of air through the aperture, and at least one sensor selected from the list consisting of temperature/humidity sensors and smoke detection sensors.

18. The method according to claim 1, wherein the method comprises installing a first data centre services module in the building prior to the installation of any other data centre services modules, and subsequently installing at least one other data centre services module, wherein installing the first data centre services module comprises specifying a three-dimensional position for the first data centre services module in the building, and locating the first data centre services module at the specified position, and wherein installing the at least one other data centre services module comprises specifying a position for the at least one other data centre services module relative to the position of the first data centre services module, and locating the at least one other data centre services module at the specified position relative to the first data centre services module.

19. The method according to claim 1, wherein the method comprises arranging the prefabricated data centre elements in a transport configuration in which the elements occupy a first sum volume, transporting the prefabricated data centre elements so arranged, and installing the prefabricated data centre elements in the building, wherein when the elements are installed in the building, they collectively define a second sum volume that is larger than the first sum volume.

20. The method according to claim 1, wherein the method comprises providing a secondary supporting frame for supporting one or more of the prefabricated data centre elements during transportation and/or installation, wherein the method additionally comprises using the secondary supporting frame as a jig to aid construction of the one or more prefabricated data centre elements.

21. The method according to claim 1, wherein each row of racks of IT equipment comprises at least 15 racks.

22. The method of claim 21, wherein the cold aisle services modules each have a length that corresponds to the width of any of from 2 to 5 IT equipment racks.

23. The method of claim 21 wherein the cold aisle services modules each have a length of from 2 to 6 metres.

24. The method of claim 1, wherein at least one cold aisle services module is connected to two other cold aisle services modules.

25. A method of making a data centre in an existing building, the building having a structure comprising a floor, walls and a roof, an air inlet for supply of air into the building, and an air outlet for removal of air from the building, wherein the method includes the following steps:
installing multiple prefabricated data centre elements by:
connecting to the air inlet an air handling module that is arranged to provide cooling capacity for the data centre; and
installing in the interior of the building multiple cold aisle services modules by suspending each of said cold aisle services modules from the structure of the building above and spaced apart from the floor, each of said cold aisle services modules having:
a length and a width,
one or more integrated blanking portions including at least one ceiling member configured to enclose a top portion of a cold aisle,
at least one clamp that attaches said cold aisle services module to an adjacent cold aisle services module,
at least one gasket that seals one or more of the one or more integrated blanking portions of said cold aisle services module and one or more of the one or more integrated blanking portions of an adjacent cold aisle services module, and
one or more data centre services extending along the length of the cold aisle services module and terminating in a connector that is connected to a corresponding connector of an adjacent data centre services module;
wherein said installing the multiple cold aisle services modules comprises fastening each respective module of said cold aisle services modules to an adjacent cold aisle services module, thereby forming a seal between associated integrated blanking portions on adjacent cold aisle services modules;

wherein the method additionally comprises installing in an interior of the building multiple racks of IT equipment, the racks being arranged in multiple parallel rows;

the method being performed so that the floor, the racks, and the cold aisle services modules including the associated integrated blanking portions together define multiple parallel spaced apart cold aisles for entraining and encapsulating the flows of cooling air to the IT equipment arranged in the racks.

* * * * *